(12) United States Patent
Bruheim et al.

(10) Patent No.: US 9,730,966 B2
(45) Date of Patent: Aug. 15, 2017

(54) METHOD OF REDUCING APPETITE IN A HUMAN SUBJECT COMPRISING ADMINISTERING KRILL OIL COMPOSITION

(71) Applicant: AKER BIOMARINE ANTARCTIC AS, Stamsund (NO)

(72) Inventors: Inge Bruheim, Volda (NO); Snorre Tilseth, Bergen (NO); Jeffery Cohn, Sydney (AU); Mikko Griinari, Espoo (FI); Sebastiano Banni, Calgliari (IT); Daniele Mancinelli, Orsta (NO); Nils Hoem, Oslo (NO); Hogne Vik, Eiksmarka (NO)

(73) Assignee: AKER BIOMARINE ANTARTIC AS, Stamsund (NO)

( * ) Notice: Subject to any disclaimer, the term of this patent is extended or adjusted under 35 U.S.C. 154(b) by 0 days.

(21) Appl. No.: 14/968,183

(22) Filed: Dec. 14, 2015

(65) Prior Publication Data
US 2016/0095888 A1   Apr. 7, 2016

Related U.S. Application Data

(60) Division of application No. 14/244,532, filed on Apr. 3, 2014, now Pat. No. 9,220,735, which is a division of application No. 12/790,575, filed on May 28, 2010, now Pat. No. 8,697,138, which is a continuation-in-part of application No. 12/057,775, filed on Mar. 28, 2008, now Pat. No. 9,034,388.

(60) Provisional application No. 60/975,058, filed on Sep. 25, 2007, provisional application No. 60/983,446, filed on Oct. 29, 2007, provisional application No. 61/024,072, filed on Jan. 28, 2008, provisional application No. 61/181,743, filed on May 28, 2009, provisional application No. 60/920,483, filed on Mar. 28, 2007.

(51) Int. Cl.
*A61K 35/612* (2015.01)
*A61K 31/202* (2006.01)
*A61K 31/215* (2006.01)
*A61K 31/683* (2006.01)

(52) U.S. Cl.
CPC .......... *A61K 35/612* (2013.01); *A61K 31/202* (2013.01); *A61K 31/215* (2013.01); *A61K 31/683* (2013.01)

(58) Field of Classification Search
CPC .............. A61K 2300/00; A61K 31/122; A61K 31/202; A61K 31/355; A61K 31/683; A61K 31/05; A61K 31/352; A61K 31/685; A61K 31/07; A61K 31/201; A61K 31/59; A61K 36/324; A61K 36/82; A61K 35/612; A61K 45/06; A61K 31/20
See application file for complete search history.

(56) References Cited

U.S. PATENT DOCUMENTS

| | | |
|---|---|---|
| 2,652,235 A | 9/1953 | Samuelsen |
| 4,036,993 A | 7/1977 | Ikeda |
| 4,038,722 A | 8/1977 | Terase et al. |
| 4,119,619 A | 10/1978 | Rogozhin et al. |
| 4,133,077 A | 1/1979 | Jasniewicz |
| 4,251,557 A | 2/1981 | Shimose et al. |
| 4,505,936 A | 3/1985 | Meyers et al. |
| 4,714,571 A | 12/1987 | Kearns et al. |
| 4,749,522 A | 6/1988 | Kamarei |
| 4,814,111 A | 3/1989 | Kearns et al. |
| 5,006,281 A | 4/1991 | Rubin et al. |
| 5,266,564 A | 11/1993 | Modolell |
| 5,434,183 A | 7/1995 | Larsson-Backstrom |
| 6,214,396 B1 | 4/2001 | Barrier |
| 6,346,276 B1 | 2/2002 | Tanouchi et al. |
| 6,537,787 B1 | 3/2003 | Breton |
| 6,800,299 B1 | 10/2004 | Beaudoin |
| 7,488,503 B1 | 2/2009 | Porzio et al. |
| 7,666,447 B2 | 2/2010 | Rockway |
| 8,030,348 B2 | 10/2011 | Sampalis |

(Continued)

FOREIGN PATENT DOCUMENTS

| | | |
|---|---|---|
| AU | 2002322233 | 2/2003 |
| BR | 8701265 | 3/1987 |

(Continued)

OTHER PUBLICATIONS

Ando and Hatano, 1988, "Isolation of apolipoproteins from carotenoid-carrying lipoprotein in the serum of chum salmon, Oncorhynchus keta", J. Lipid Research, 29: 1264-1271.
Aoi et al., 2003, "Astaxanthin limits exercise-induced skeletal and cardiac muscle damage in mice", Antioxidants & Redox Signaling, 5(1): 139-44.
Britton, 1985, "General Carotenoid Methods", Methods in Enzymology, vol. 111, pp. 113-149.
Calder, 2006, "n-3 polyunsaturated fatty acids, inflammation, and inflammatory diseases", Am. J. Clin. Nutr., 83: 1505S.

(Continued)

*Primary Examiner* — Debbie K Ware
(74) *Attorney, Agent, or Firm* — Casimir Jones S.C.

(57) ABSTRACT

This invention discloses methods of using krill oil and compositions comprising krill oil to treat risk factors for metabolic, cardiovascular, and inflammatory disorders. The present invention also relates to methods of using compositions comprising krill oil to modulate biological processes selected from the group consisting of glucose metabolism, lipid biosynthesis, fatty acid metabolism, cholesterol biosynthesis, and the mitochondria respiratory chain. The present invention further includes pharmaceutical and/or nutraceutical formulations made from krill oil, methods of making such formulations, and methods of administering them to treat risk factors for metabolic, cardiovascular, and inflammatory disorders. Further, a method of reducing appetite in humans by administering a krill oil composition is also disclosed.

4 Claims, 26 Drawing Sheets

(56) References Cited

U.S. PATENT DOCUMENTS

Figure 1:
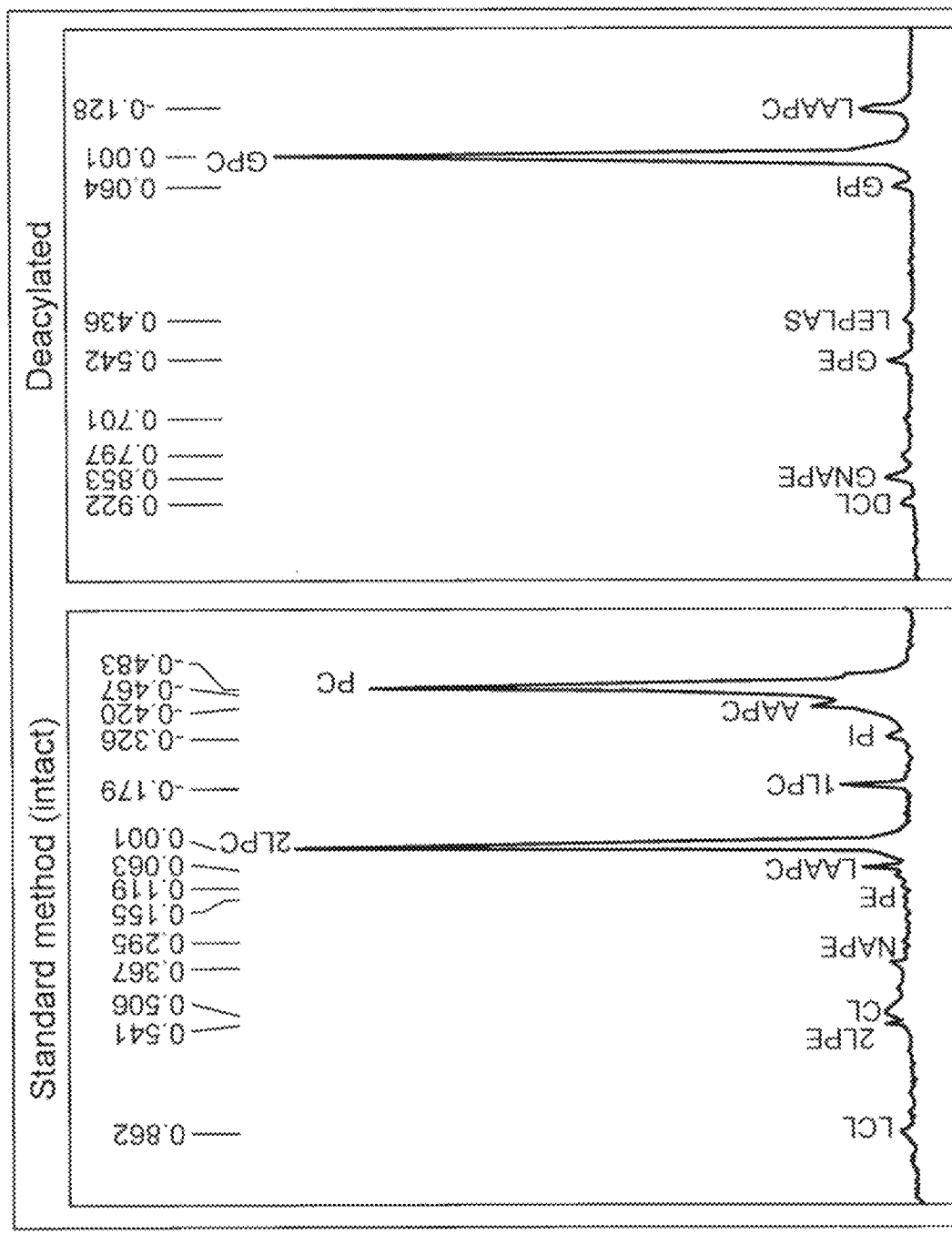

| | | | |
|---|---|---|---|
| 8,057,825 | B2 | 11/2011 | Sampalis |
| 8,278,351 | B2 | 10/2012 | Sampalis |
| 8,372,812 | B2 | 2/2013 | Tilseth et al. |
| 8,383,675 | B2 | 2/2013 | Sampalis |
| 8,697,138 | B2 | 4/2014 | Bruheim et al. |
| 9,028,877 | B2 | 5/2015 | Bruheim et al. |
| 9,034,388 | B2 | 5/2015 | Bruheim et al. |
| 9,072,752 | B1 | 7/2015 | Bruheim et al. |
| 9,078,905 | B2 | 7/2015 | Bruheim et al. |
| 9,119,864 | B2 | 9/2015 | Bruheim et al. |
| 2002/0076468 | A1 | 6/2002 | Saxby |
| 2003/0044495 | A1 | 3/2003 | Kagan |
| 2003/0113432 | A1 | 6/2003 | Yoshitomi |
| 2004/0241249 | A1 | 12/2004 | Sampalis |
| 2005/0003073 | A1 | 1/2005 | Pivovarov et al. |
| 2006/0078625 | A1 | 4/2006 | Rockway |
| 2006/0193962 | A1 | 8/2006 | Kamiya et al. |
| 2008/0166419 | A1 | 7/2008 | Sones |
| 2008/0166420 | A1 | 7/2008 | Sones |
| 2008/0274203 | A1* | 11/2008 | Bruheim ............... A61K 9/4858 424/522 |
| 2009/0061067 | A1 | 3/2009 | Tilseth et al. |
| 2010/0143571 | A1 | 6/2010 | Breivik |
| 2010/0160659 | A1 | 6/2010 | Catchpole |
| 2010/0226977 | A1 | 9/2010 | Tilseth et al. |
| 2011/0130458 | A1 | 6/2011 | Breivik |
| 2014/0005421 | A1 | 1/2014 | Bruheim et al. |
| 2014/0010888 | A1 | 1/2014 | Bruheim et al. |
| 2014/0080791 | A1 | 3/2014 | Berge et al. |
| 2014/0088043 | A1 | 3/2014 | Hoem et al. |
| 2014/0088047 | A1 | 3/2014 | Hoem et al. |
| 2014/0107072 | A1 | 4/2014 | Tilseth et al. |
| 2014/0274968 | A1 | 9/2014 | Berge et al. |
| 2014/0363517 | A1 | 12/2014 | Bruheim et al. |
| 2014/0370115 | A1 | 12/2014 | Hoem et al. |
| 2015/0030718 | A1 | 1/2015 | Saebo |
| 2015/0050403 | A1 | 2/2015 | Tilseth et al. |
| 2015/0164841 | A1 | 6/2015 | Hoem et al. |

FOREIGN PATENT DOCUMENTS

| | | |
|---|---|---|
| CA | 1098900 | 4/1981 |
| CL | 40348 | 7/1997 |
| CN | 102746941 | 1/2014 |
| EP | 0609078 | 8/1994 |
| EP | 0670306 | 6/1995 |
| EP | 1127497 | 8/2001 |
| EP | 1392623 | 3/2004 |
| EP | 1406641 | 4/2004 |
| EP | 1631280 | 4/2004 |
| EP | 1542670 | 6/2005 |
| EP | 0973532 | 9/2005 |
| EP | 1689413 | 8/2006 |
| EP | 1660071 | 1/2007 |
| EP | 1743531 | 1/2007 |
| EP | 1123368 | 4/2008 |
| EP | 1419768 | 1/2009 |
| EP | 1292294 | 3/2009 |
| EP | 1706106 | 7/2009 |
| EP | 1385500 | 7/2010 |
| GB | 2097014 | 10/1982 |
| GB | 921537 | 6/1999 |
| JP | S51-125774 | 11/1976 |
| JP | S52-114046 | 9/1977 |
| JP | 60-153779 | 8/1985 |
| JP | 61281159 | 12/1986 |
| JP | 02049091 | 2/1990 |
| JP | 2215351 | 8/1990 |
| JP | 4012665 | 1/1992 |
| JP | 2963152 | 2/1992 |
| JP | 04057853 | 2/1992 |
| JP | 3081692 | 7/1994 |
| JP | 2524217 | 8/1996 |
| JP | H08-231391 | 8/1996 |
| JP | 3344887 | 7/1997 |
| JP | 3611222 | 8/1997 |
| JP | 2909508 | 6/1999 |
| JP | 2001-158736 | 6/2001 |
| JP | 2003-003192 | 1/2003 |
| JP | 2003-048831 | 2/2003 |
| JP | 2003-146883 | 5/2003 |
| JP | 3467794 | 9/2003 |
| JP | 2003-530448 | 10/2003 |
| JP | 3486778 | 10/2003 |
| JP | 2004-534800 | 11/2004 |
| JP | 3678317 | 5/2005 |
| JP | 2005-245379 | 9/2005 |
| JP | 2006-069948 | 3/2006 |
| JP | 2006-083136 | 3/2006 |
| JP | 2006-290784 | 10/2006 |
| JP | 2006-316073 | 11/2006 |
| JP | 2006-328014 | 12/2006 |
| JP | 2007-126455 | 5/2007 |
| JP | 2007-246404 | 9/2007 |
| SU | 220741 | 1/1971 |
| WO | 82/02819 | 9/1982 |
| WO | 86/06082 | 10/1986 |
| WO | 89/01031 | 2/1989 |
| WO | 89/10960 | 11/1989 |
| WO | 90/05765 | 5/1990 |
| WO | 93/24142 | 12/1993 |
| WO | 97/38585 | 10/1997 |
| WO | 97/39759 | 10/1997 |
| WO | 98/34498 | 8/1998 |
| WO | 99/39589 | 8/1999 |
| WO | 00/23546 | 4/2000 |
| WO | 00/25608 | 5/2000 |
| WO | 00/38708 | 7/2000 |
| WO | 01/28526 | 4/2001 |
| WO | 01/82928 | 11/2001 |
| WO | 02-083122 | 10/2002 |
| WO | 02/083122 | 10/2002 |
| WO | 02/092540 | 11/2002 |
| WO | 02/102394 | 12/2002 |
| WO | 03/011873 | 2/2003 |
| WO | 03/013497 | 2/2003 |
| WO | 2004/028529 | 4/2004 |
| WO | 2004/047554 | 6/2004 |
| WO | 2004/112767 | 12/2004 |
| WO | 2005/004593 | 1/2005 |
| WO | 2005-018632 | 3/2005 |
| WO | 2005/037848 | 4/2005 |
| WO | 2005/038037 | 4/2005 |
| WO | 2005/070411 | 8/2005 |
| WO | 2006/030552 | 3/2006 |
| WO | 2004-100943 | 5/2006 |
| WO | 2006/111633 | 10/2006 |
| WO | 2007/080514 | 7/2007 |
| WO | 2007/080515 | 7/2007 |
| WO | 2007/108702 | 9/2007 |
| WO | 2007/123424 | 11/2007 |
| WO | 2008/006607 | 1/2008 |
| WO | 2008/072563 | 6/2008 |
| WO | 2008/117062 | 10/2008 |
| WO | 2009/027692 | 3/2009 |
| WO | 2010/097701 | 9/2010 |
| WO | 2013/102792 | 7/2013 |
| WO | 2014/013335 | 1/2014 |

OTHER PUBLICATIONS

Charest et al., 2001, "Astaxanthin Extraction from Crawfish Shells by Supercritical CO2 with Ethanol as Cosolvent", J. Aquatic Food Product Technology, 10(3): 79-93.

Chen and Meyers, 1982, "Extraction of Astaxanthin Pigment from Crawfish Waste Using a Soy Oil Process", J. Food Sci., 47: 892-896.

Clarke, 1980, "The Biochemical Composition of Krill, *Euphausia superba* dana,from South Georgia", J. Exp. Mar. Biol. Ecol., 43: 221-236.

Czeczuga, 1974, "Comparative Studies of Carotenoids in the Fauna of the Gullmar Fjord (Bohuslan, Sweden). II. Crustacea: Eupagurus bernhardus, Hyas coarctatus and Upogebia deltaura", Marine Biology, 28: 95-98.

(56) References Cited

OTHER PUBLICATIONS

De Ritter and Purcell, 1981, "Carotenoid Analytical Methods", Carotenoids as Colorants and Vitamin A Precursors: Technological and Nutritional Applications, pp. 815-882.
Deutch, 1995, "Menstrual pain in Danish women correlated with low n-3 polyunsaturated fatty acid intake", Eur. J. Clin. Nutr., 49(7): 508-16.
Diez et al., 2003, "The role of the novel adipocyte-derived hormone adiponectin in human disease", Eur. J. Endocrinol., 148(3): 293-300.
Ellingsen et al., 1987, "Biochemistry of the autolytic processes in Antarctic krill post mortem. Autoproteolysis." Biochem. J. 246, 295-305.
Emodi, 1978, "Carotenoids: Properties and Applications", Food Technology, 32(5): 38.
Felix-Valenzuela et al., 2001, "Supercritical CO2/Ethanol Extraction of Astaxanthin from Blue Crab (*Callinectes sapidus*) Shell Waste", Journal of Food Process Engineering, 24: 101-112.
Fox and Scheer, 1941, "Comparative Studies of the Pigments of Some Pacific Coast Echinoderms", The Biological Bulletin, 441-455.
Geusens et al., 1994, "Long-term effect of omega-3 fatty acid supplementation in active rheumatoid arthritis. A 12-month, double-blind, controlled study", Arthritis Rheum., 37(6): 824-9.
Gilchrist and Green, 1960, "The Pigments of Artemia", Proceedings of the Royal Society, Series B Biological Sciences, vol. 152 No. 946, pp. 118-136.
Goodwin and Srisukh, 1949, "Some Observations on Astaxanthin Distribution in Marine Crustacea", Department of Biochemistry, University of Liverpool, pp. 268-270.
Gulyaev and Bugrova, 1976 "Removing fats from the protein paste Okean". Konservnaya I Ovoshchesushil'naya Promyshlennost, (4), 37-8.
Hardardottir and Kinsella, 1988, "Extraction of Lipid and Cholesterol from Fish Muscle with Supercritical Fluids" Journal of Food Science, 53(6): 1656-1658.
International Aqua Feed, 2006, vol. 9, 50 pages.
International Search Report and Written Opinion for PCT/GB2008/002934, Dated Mar. 11, 2009.
International Search Report and Written Opinion for PCT/IB2010/000512; dated Jun. 24, 2010.
International Search Report for PCT/IB2007/000098, dated: Jun. 26, 2007.
Itoh et al., 2007; "Increased adiponectin secretion by highly purified eicosapentaenoic acid in rodent models of obesity and human obese subjects", Arteriosclerosis, Thrombosis, and Vascular Biology; 27(9): 1918-1925.
Johnson et al., 1978, "Simple Method for the Isolation of Astaxanthin from the Basidiomycetous Yeast *Phaffia rhodozyma*", Applied and Environmental Microbiology, 35(6): 1155-1159.
Kolakowska, 1989, "Krill lipids after frozen storage of about one year in relation to storage time before freezing", Die Nahrung Food, 33(3): 241-244.
Kris-Etherton et al., 2002, "Fish Consumption, Fish Oil, Omega-3 Fatty Acids, and Cardiovascular Disease", Circulation, 106:2747-2757.
Kristensen et al., 1989, "Dietary supplementation with n-3 polyunsaturated fatty acids and human platelet function: a review with particular emphasis on implications for cardiovascular disease", J. Intern. Med. Suppl. 731:141-50.
Kunesova et al., 2006, "The influence of n-3 polyunsaturated fatty acids and very low calorie diet during a short-term weight reducing regimen on weight loss and serum fatty acid composition in severely obese women", Physiol Res.; 55 (1):63-72.
Laight et al., 1999, "F2-isoprostane evidence of oxidant stress in the insulin resistant, obese Zucker rat: effects of vitamin E", Eur. J. Pharmacol. 377(1): 89-92.
Lambertson and Braekkan, 1971, "Method of Analysis of Astaxanthin and its Occurrence in some Marine Products," J. Sci. Food. Agr., vol. 22(2): 99-101.

Libby et al., 2006, "Inflammation and Atherothrombosis: From Population Biology and Bench Research to Clinical Practice", J. Amer. Coll. Card., 48 (9, Suppl. A): A33-A46.
Lopez et al., 2004, "Selective extraction of astaxanthin from crustaceans by use of supercritical carbon dioxide", Talanta, 64: 726-731.
Mandeville, 1991, "Isolation and Identification of Carotenoid Pigments, Lipids and Flavor Active Components from Raw Commercial Shrimp Waste", Food Biotechnology, 5(2): 185-195.
Meyers and Bligh, 1981, "Characterization of Astaxanthin Pigments from Heat-Processed Crawfish Waste", J. Agric. Food Chem., 29: 505-508.
Meyers, 1977, "Using Crustacean Meals and Carotenoid-Fortified Diets", Feedstuffs, vol. 49(19).
Meyers, 1994, "Developments in world aquaculture, feed formulations, and role of carotenoids", Pure & Appl. Chem, vol. 66(5): 1069-1076.
Mills et al., 1989, "Dietary N-6 and N-3 fatty acids and salt-induced hypertension in the borderline hypertensive rat", Lipids, 24(1): 17-24.
Moates and Van Bentem, 1990, "Separating out the value", Food Science and Technology Today, 4(4): 213-214.
Nikolaeva, 1967 "Amino acid composition of protein-coagulate in krill", VNIRO, 63:161-4.
Phleger, et al. (2002) "Interannual and between species comparison in the lipids, fatty acids, and sterols of Antarctic krill from the US AMLR Elephant Island survey area: 1997 and 1998". Comp Biochem Physiol 131B:733-747.
Popp-Snijders et al., 1987, "Dietary supplementation of omega-3 polyunsaturated fatty acids improves insulin sensitivity in non-insulin-dependent diabetes", Diabetes Res. 4(3): 141-7.
Sachindra, 2006, "Recovery of carotenoids from shrimp waste in organic solvents", Waste Management, 26: 1092-1098.
Saether et al., 1986, "Lipids of North Atlantic krill", J Lipid Res., 27(3):274-85.
Shahidi et al., 1998, "Carotenoid Pigments in Seafoods and Aquaculture" Critical Reviews in Food Science, 38(1): 1-67.
Sidehu et al., 1970, "Biochmical Composition and Nutritive Value of Krill (*Euphausia superb* dana)", J. Sci Food Agr., vol. 21, 293-296.
Simopoulos, 1991, "Omega-3 fatty acids in health and disease and in growth and development", Am. Clin. Nutr. 54:438-63.
Somiya, 1982, "'Yellow lens' eyes of a stomiatoid deep-sea fish, *Malacosteus niger*", Proc. R. Soc. Lond., 215: 481-489.
Valeri, D., et al., "Visocities of Fatty acids, triglycerides and their binary mixtures," JAOCS 74 (1997) pp. 1221-1226.
CRC 2013-2014, "Viscosity of Liquids", 94th ed., pp. 6-231-6-235.
EP Opposition filed Feb. 13, 2014 by Olympic Seafood AS, EP Patent Application No. EP0871891016.
Brzustowicz, Michael R., et al., "Controlling Membrane Cholesterol Content. A Role for Polyunsaturated (Docosahexaenoate) Phospholipids," Biochemistry (2002), 41, pp. 12509-12519.
Jong-Ho Lee, "A Review: Antioxygenic and Peroxide-decomposing Activities of Antarctic Krill Lipids," J. Korean Soc. Food Mutr. 13(3) pp. 326-333 (1984).
Ki Woong Cho, et al., "Lipid and Fatty Acid Composition of the Antarctic Krill *Euphausia superba*," Ocean Research 21(2): 109-116 (1999).
Hvattum, Erlend, et al., "Effect of soybean oil and fish oil on individual molecular species of Atlantic salmon . . . ", Journal of Chromatography B, 748 (2000) 137-149.
Igarashi, Daisuke, et al., "Positional Distribution of DHA and EPA in Phosphatidylcholine and Phosphatidylethanolamine from Different Tissues of Squids," J. Oleo Sci. vol. 50, No. 9 (2001).
Tochizawa, Kaoru, et al., "Effects of Phospholipds Containing Docosahexaenoic Acid on Differentiation and Growth of HL-60 Human Promyelocytic Leukemia Cells," J. Jpn. Oil Chem. Soc. vol. 46, No. 4 (1997).
Zerouga, Mustapha, et al., "Comparison of phosphatidylcholines containing one or two docosahexaenoic acyl chains on properties of phospholipid monolayers and bilayers," Biochimica et Biophysica Acta 1236 (1995) 266-272.

(56) References Cited

OTHER PUBLICATIONS

Eung-Ho Lee, et al., "Studies on the Processing of Krill Sauce," J. Korean Soc. Food Nutr. 13(1) 97-106 (1984).
Hyun-Ku Kim, et al., "Effects of Cooking and Drying Methods on the Polar Lipds Composition of Shrimp," Korean J. Food Sci. Technol. vol. 21, No. 1, pp. 25-30 (1989).
Shon, Mi-Yae, et al., "Effects of Krill and Cadmium on Lipid Composition of Plasma in Cholesterol-Fed Rats," J. Korean Soc. Food Nutr. 23(1), 38-43 (1994).
Summons Materials downloaded from ESPACE on Dec. 16, 2014 for EP Patent Application No. 08 718 910.6.
Yanase, M., "Innovations on the russian method for separating heat coagulated protein from antarctic krill, through autolysis," Bulletin of Tokai Regional Fisheries Research Laboratory, 1974, No. 78, p. 79-84.
Kolakowski and Gajowiecki, "Optimization of autoproteolysis to obtain and edible product 'precipitate' from Antarctic krill," Seafood Science and Technology, pp. 331-336.
EP Opposition filed May 8, 2015 by Olympic Seafood AS, EP Patent No. 2144618, 150 pages.
Allahpichay et al., "Extraction of Growth Promoting Fractions from Non-muscle Krill Meal of *Euphausia superba* and its Effect on Fish Growth," Bulletin of the Japanese Society of Scientific Fisheries, 1984, 50(5): 821-826.
Takaichi et al., 2003, "Fatty Acids of astaxanthin esters in krill determined by mild mass spectrometry", Comparative Biochemistry and Physiology Part B, Biochemistry and Molecular Biology, Elsevier, Oxford, vol. 136, Jan. 1, 2003, p. 317-322.
Tanaka et al., 2004, "Extraction of Phospholipids from Salmon Roe with Supercritical Carbon Dioxide and an Entrainer", J. Oleo Sci, 53(9): 417-424.
Tanaka et al., 2005, "Extraction of Phospholipids from Unused Natrual Resources with Supercritical Carbon Dioxide and an Entrainer", Journal of Oleo Science, vol. 54(11): 569-576.
Todoric et al., 2006, "Adipose tissue inflammation induced by high-fat diet in obese diabetic mice is prevented by n-3 polyunsaturated fatty acids", Diabetologia, 49(9): 2109-2119.
Tou et al., 2007, "Krill for human consumption: nutritional value and potential health benefits.", Nutrition Rev 65 (2):63-77.
Trayhurn et al., 2004, "Adipokines: inflammation and the pleiotropic role of white adipose tissue", Br. J. Nutrition, 92(3): 347-355.
Trebble et al., 2003, "Inhibition of tumour necrosis factor-alpha and interleukin 6 production by mononuclear cells following dietary fish-oil supplementation in healthy men and response to antioxidant co-supplementation", Br. J. Nutrition, 90(2): 405-412.
Ukkola et al., 2002, "Adiponectin: a link between excess adiposity and associated comorbidities?", J. Mol. Med., 80 (11): 696-702.
Van Der Veen et al., 1971 "The Lipids of Krill (*Euphausia* Species) and Red Crab (*Pleuroncodes planipes*)", Lipids, 6(7): 481-485.
Virtue, et al. 1996, Reproductive trade-off in male Antarctic krill, *Euphausia superba*, Marine Biology, vol. 126, No. 3, pp. 521-527.
Yamaguchi et al., 1983, "The Composition of Carotenoid Pigments in the Antarctic Krill *Euphausia superba*", Bulletin of the Japanese Society of Scientific Fisheries, 49(9): 1411-1415.
Yamaguchi et al., 1986, "Supercritical Carbon Dioxide Extraction of Oils From Antarctic Krill," Journal of Agricultural and Food Chemistry, vol. 34, pp. 904-907.
Yanase M; 1974, "Modification of a Russian method for separation of heat-coagulated protein from Antarctic krill", Database FSTA (online); International Food Information Service (IFIS); Frankfurt-Main, DE.
Yen et al., 1994, "Effect of dietary omega-3 and omega-6 fatty acid sources on PUVA-induced cutaneous toxicity and tumorogenesis in the hairless mouse", Arch. Dermatol. Res., 286(6): 331-6.
Database WPI Week 200682, Thomson Scientific, London, GB, 2006.
Yanase, M., "Modification of Russian Method for Separating Heat Congulated Protein from Antarctic Krill," Bull. Tokai Reg. Fish. Res. Lab, 78: 79-84 (1974).
Sikorski, E., "The Utilization of Krill for Food," Food Process Eng., 1:845-855 (1980).
Budzinskli, E., et al., "Possibilities of processing and marketing of products made from Antarctic Krill", FAO Fish. Tech. Pap. (268) 46 pages (1985) (Budzinski).
Bunea R., et al., "Evaluation of the Effects of Neptune Krill Oil on the Clinical Course of Hyperlipidemia," Alternative Medicine Review, Thorne Research Inc., Sandpoint, US, vol. 9, No. 4, Jan. 1, 2004.
Gordeev, K.Y., et al. "Fatty Acid Composition of the Main Phospholipids of the Antarctic Krill, *Euphausia superba*," Khim. Prirod. Soed. 2 (1990), pp. 181-187.
Dec. 8, 2011 Office Action, KR Patent Application No. 10-2010-7006897 and its English translation.
JP Office Action mailed Feb. 23, 2012, JP Patent Application No. 2010-522444 (and English translation).
CN Office Action mailed Apr. 27, 2012, JP Patent Application No. 200880112125.6 (and English translation).
Fricke, et al., Lipid, Sterol and Fatty Acid Composition of Antarctic Krill (*Euphausia superba* Dana), Lipids (1984) 19 (11): 821-827.
Fricke, et al., 1-O-Alkylglycerolipids in Antarctic Krill (*Euphausia superba* Dana), Comp. Biochem. Physiol. (1986) 85B(1): 131-134.
Gordeev, K.Y., et al. "Fatty Acid Composition of the Main Phospholipids of the Antarctic Krill, *Euphausia superba*," Chem. Nat. Cmpds. (1990) 26(2), pp. 143-147.
Grantham (1977) Southern Ocean Fisheries Survey Programme, FAO Rome, GLO/SO/77/3: 1-61.
Raventos et al., Application and Posssibilities of Supercritical CO2 Extraction in Food Processing Industry: An Overview, Food Science and Technology International (2002) 8: 269-284.
Tanaka, T., et al.., Platelet-activating Factor (PAF)-like Phospholoipds Formed during Peroxidation of Phosphatidylcholines from Different Foodstuffs, Biosci. Biotech. Biochem. (1995) 59 (8), pp. 1389-1393.
Winther, et al., Elucidation of Phosphatidylcholine Composition in Krill Oil Extracted from *Euphausia superba*, Lipids (2011) 46: 25-36.
International Search Report, International Patent Application No. PCT/IB2016/000208, mailed May 13, 2016, five pages.
Partial International Search Report, International Patent Application No. PCT/IB2016/000326, mailed Jun. 15, 2016, six pages.
Database FSTA [Online]} International Food Information Service, Frankfurt-Main; Shibata N. "Effect of fishing season on lipid content and composition of Antarctic krill (translated)" Database accession No. FS-1985-04-r-0091, abstract only.
Statement of Grounds and Particulars, Rimfrost AS, filed Jun. 10, 2016, Australian Patent Application No. 2014203179, 21 pages.

\* cited by examiner

METHOD OF REDUCING APPETITE IN A HUMAN SUBJECT COMPRISING ADMINISTERING KRILL OIL COMPOSITION

CROSS-REFERENCE TO RELATED APPLICATIONS

This application is a divisional of pending U.S. patent application Ser. No. 14/244,532, filed Apr. 3, 2014, now allowed as U.S. Pat. No. 9,220,735 which is a divisional of U.S. patent application Ser. No. 12/790,575, filed May 28, 2010, now U.S. Pat. No. 8,697,138, which claims the benefit of U.S. Provisional Patent Application No. 61/181,743, filed May 28, 2009, and is a continuation-in-part of U.S. patent application Ser. No. 12/057,775, filed Mar. 28, 2008, now U.S. Pat. No. 9,034,388, which claims the benefit of U.S. Provisional Patent Application No. 60/920,483, filed Mar. 28, 2007, U.S. Provisional Patent Application No. 60/975,058, filed Sep. 25, 2007, U.S. Provisional Patent Application No. 60/983,446, filed Oct. 29, 2007, and U.S. Provisional Patent Application No. 61/024,072, filed Jan. 28, 2008, all of which are incorporated by reference herein in their entirety.

FIELD OF THE INVENTION

This invention relates generally to methods of using krill oil to treat risk factors for metabolic, cardiovascular, and inflammatory disorders, including, but not limited to, modulating endocannabinoid concentrations; reducing ectopic fat; reducing triacylglycerides in the liver and heart; reducing monoacylglyceride lipase activity in the visceral adipose tissue, liver, and heart; increasing levels of DHA in the liver; increasing the levels of EPA and DHA in the phospholipid fractions of tissues that exhibit changes in endocannabinoid concentration; reducing susceptibility to inflammation, modulating glucose and lipid homeostasis; reducing fatty liver disease (alcoholic and non-alcoholic); reducing MAGL activity in the heart; increasing levels of plasma ALA/LA; decreasing levels of ALA/LA in the heart; decreasing levels of ARA in the subcutaneous adipose tissue; and decreasing availability of substrates to decrease the activity of the endocannabinoid system. The present invention also relates to methods of using compositions comprising krill oil to modulate biological processes selected from the group consisting of glucose metabolism, lipid biosynthesis, fatty acid metabolism, cholesterol biosynthesis, and the mitochondrial respiratory chain. The present invention further includes pharmaceutical and/or nutraceutical formulations made from krill oil, methods of making such formulations, and methods of administering them to treat risk factors for metabolic, cardiovascular, and inflammatory disorders.

BACKGROUND OF THE INVENTION

Krill is a small crustacean which lives in all the major oceans worldwide. For example, it can be found in the Pacific Ocean (*Euphausia pacifica*), in the Northern Atlantic (*Meganyctiphanes norvegica*) and in the Southern Ocean off the coast of Antarctica (*Euphausia superba*). Krill is a key species in the ocean as it is the food source for many animals such as fish, birds, sharks and whales. Krill can be found in large quantities in the ocean and the total biomass of Antarctic krill (*Euphausia superba*) is estimated to be in the range of 300-500 million metric tons. Antarctic krill feeds on phytoplankton during the short Antarctic summer. During winter, however, its food supply is limited to ice algae, bacteria, marine detritus as well as depleting body protein for energy. Virtue et al., *Mar. Biol.* 126, 521-527. For this reason, the nutritional values of krill vary during the season and to some extent annually. Phleger et al., *Comp. Biochem. Physiol.* 131B (2002) 733. In order to accommodate variations in food supply, krill has developed an efficient enzymatic digestive apparatus resulting in a rapid breakdown of the proteins into amino acids. Ellingsen et al., *Biochem. J.* (1987) 246, 295-305. This autoproteolysis is highly efficient also post mortem, making it a challenge to catch and store the krill in a way that preserves the nutritional quality of the krill. Therefore, in order to prevent the degradation of krill the enzymatic activity is either reduced by storing the krill at low temperatures or the krill is made into a krill meal.

During the krill meal process the krill is cooked so that all the active enzymes are denatured in order to eliminate all enzymatic activity. Krill is rich in phospholipids which act as emulsifiers. Thus, it is more difficult to separate water, fat, and proteins using mechanical separation methods than it is in a regular fish meal production line. In addition, krill becomes solid, gains weight and loses liquid more easily when mixed with hot water. Eventually this may lead to a gradual build up of coagulated krill proteins in the cooker and a non-continuous operation due to severe clogging problems. In order to alleviate this, hot steam must be added directly into the cooker. This operation is energy demanding and may also result in a degradation of unstable bioactive components in the krill oil, such as omega-3 fatty acids, phospholipids and astaxanthin. The presence of these compounds make krill oil an attractive source as a food supplement, a functional food product, and a pharmaceutical for the animal and human applications.

Omega-3 fatty acids have been shown to have potential effect of preventing cardiovascular disease, cognitive disorders, joint disease and inflammation-related diseases such as rheumatoid arthritis and osteoarthritis. Astaxanthin is a strong antioxidant and may also assist in promoting optimal health.

Published PCT Application No. WO 00/23546 discloses isolation of krill oil from krill using solvent extraction methods. Krill lipids have been extracted by placing the material in a ketone solvent (e.g., acetone) in order to extract the lipid soluble fraction. This method involves separating the liquid and solid contents and recovering a lipid rich fraction from the liquid fraction by evaporation. Further processing steps include extracting and recovering by evaporation the remaining soluble lipid fraction from the solid contents by using a solvent such as ethanol. The compositions produced by these methods are characterized by containing at least 75 μg/g astaxanthin, preferably 90 μg/g astaxanthin. Another krill lipid extract disclosed contained at least 250 μg/g canastaxanthin, preferably 270 μg/g canastaxanthin.

Published PCT Application No. WO 02/102394 discloses methods of treating and/or preventing cardiovascular disease, rheumatoid arthritis, skin cancer, premenstrual syndrome, diabetes, and enhancing transdermal transport. The methods include administering a krill or marine oil to a patient. The application also describes a test that was carried out to evaluate the effects of krill and/or marine oils on arteriosclerotic coronary artery disease and hyperlipidemia, and resulted in a cholesterol decrease of about 15%, a triglyceride decrease of about 15%, an HDL increase of about 8%, an LDL decrease of about 13%, and a cholesterol: HDL ratio decrease of about 14%

Published PCT Application No. WO 2007/080515 discloses a marine lipid extract derived from krill. The extract can be used in methods for preventing or treating thrombosis.

Korean Published Application No. 2006008155 discloses an oral composition comprising a mixture of glucosamine and krill oil (provided in a ratio of 2:3) for use in methods of inhibiting osteoarthritis.

U.S. Pat. No. 7,666,447 discloses compositions including krill extracts and conjugated linoleic acid. The compositions are used in methods for treating an individual having a disease state selected from the group consisting of a joint ailment, PMS, Syndrome X, cardiovascular disease, bone disease and diabetes. The methods comprise administering to the individual a therapeutically effective amount of a composition including conjugated linoleic acid and a krill extract comprising krill oil.

However, there remains a need in the art for methods of using compositions comprising krill oil to treat risk factors for metabolic, cardiovascular, and inflammatory disorders.

SUMMARY OF THE INVENTION

The present invention provides methods of using compositions comprising krill oil (KO) to treat risk factors for metabolic, cardiovascular, and inflammatory disorders, including, but not limited to, modulating endocannabinoid concentrations; reducing ectopic fat; reducing triacylglycerides in the liver and heart; reducing monoacylglyceride lipase activity in the visceral adipose tissue, liver, and heart; increasing levels of DHA in the liver; increasing the levels of EPA and DHA in the phospholipid fractions of tissues that exhibit changes in endocannabinoid concentration; reducing susceptibility to inflammation, modulating glucose and lipid homeostasis; reducing fatty liver disease (alcoholic and non-alcoholic); reducing MAGL activity in the heart; increasing levels of plasma ALA/LA; decreasing levels of ALA/LA in the heart; decreasing levels of ARA in the subcutaneous adipose tissue; and decreasing availability of substrates to decrease the activity of the endocannabinoid system. The present invention also provides methods of using compositions comprising krill oil to modulate biological processes selected from the group consisting of glucose metabolism, lipid biosynthesis, fatty acid metabolism, cholesterol biosynthesis, and the mitochondrial respiratory chain. The present invention further includes pharmaceutical and/or nutraceutical formulations made from the compositions, methods of making such formulations, and methods of administering them to treat risk factors for metabolic, cardiovascular, and inflammatory disorders.

In some embodiments, the present invention provides methods of administering compositions comprising krill oil to treat risk factors for metabolic, cardiovascular, and inflammatory disorders in a human subject, where the method includes the step of administering compositions containing krill oil. The risk factors that are treated are selected from the group consisting of modulating endocannabinoid concentrations; reducing ectopic fat; reducing triacylglycerides in the liver and heart; reducing monoacylglyceride lipase activity in the visceral adipose tissue, liver, and heart; increasing levels of DHA in the liver; increasing the levels of EPA and DHA in the phospholipid fractions of tissues that exhibit changes in endocannabinoid concentration; reducing susceptibility to inflammation, modulating glucose and lipid homeostasis; reducing fatty liver disease (alcoholic and non-alcoholic); reducing MAGL activity in the heart; increasing levels of plasma ALA/LA; decreasing levels of ALA/LA in the heart; decreasing levels of ARA in the subcutaneous adipose tissue; and decreasing availability of substrates to decrease the activity of the endocannabinoid system.

In some embodiments, the present invention provides methods of administering compositions comprising krill oil to modulate biological processes in a human subject, where the method includes the step of administering compositions containing krill oil. The biological processes are selected from the group consisting of glucose metabolism, lipid biosynthesis, fatty acid metabolism, cholesterol biosynthesis, and the mitochondrial respiratory chain. These biological processes may be modulated by altering the expression of one or more genes, including, but not limited to, reduced or decreased expression of Ppargc1a (peroxisome proliferator-activated receptor gamma coactivator 1a), Hnf4a (hepatocyte nuclear factor 4 alpha), Pck1 (phosphoenolpyruvate carboxykinase 1), G6pc (glucose-6-phosphatase, catalytic), Cpt1a (carnitine palmitoyl transferase 1a), Acads (acyl-coenzyme A dehydrogenase, short chain), Acadm (acyl-coenzyme A dehydrogenase, medium chain), Acadl (acyl-coenzyme A dehydrogenase, long chain), Hmgcr (3-hydroxy-3-methylglutaryl-coenzyme A reductase), Pmvk (phosphomevalonate kinase), Sbref2 (sterol regulatory element binding factor 2), Ppargc1b (peroxisome proliferator-activated receptor gamma coactivator 1 b), and Sod2 (superoxide dismutase 2). These biological processes may also be affected by enhanced or increased expression of NADH (nicotinamide adenine dinucleotide) dehydrogenase and subunits thereof. The biological processes are also affected by factors including reduced hepatic glucose production, reduced hepatic gluconeogenesis, and reduced hepatic lipid synthesis.

In some embodiments, the present invention provides methods of decreasing lipid content in the liver of a human subject, comprising: administering to said subject an effective amount of a krill oil composition under conditions such that lipid content in the liver of the subject is decreased. In some embodiments, the human subject is clinically obese.

In certain embodiments, the present invention provides methods comprising providing a krill oil composition to a human subject under conditions such that the cardiovascular disease risk factors of the subject are improved. In some embodiments, the cardiovascular risk factors are selected from the group consisting of elevated blood pressure, elevated serum total cholesterol and low-density lipoprotein cholesterol (LDL-C), low serum high-density lipoprotein cholesterol (HDL-C), diabetes mellitus, abdominal obesity, elevated serum triglycerides, small LDL particles, elevated serum homocysteine, elevated serum lipoprotein(a), pro-thrombotic factors, fatty liver and inflammatory markers. In some embodiments, the human subject is clinically obese.

In certain embodiments, the present invention provides methods comprising providing a krill oil composition to a human subject under conditions such that cannabinoid receptor signaling is reduced. In some embodiments, inhibition of the endocannabinoid system of the subject comprises lowering the levels of arachidonylethanolamide (AEA) and/or 2-arachidonyl glycerol (2-AG). In some embodiments, the human subject is clinically obese.

In certain embodiments, the present invention provides methods comprising providing a krill oil composition to a human subject; and administering the krill oil composition to the human subject under conditions such that the appetite of the subject is reduced. In some embodiments, the human subject is clinically obese.

In certain embodiments, the present invention provides methods comprising providing a krill oil composition to a human subject; and administering the krill oil composition to the human subject under conditions such that fat accumulation in the subject is reduced. In some embodiments, the human subject is clinically obese.

In certain embodiments, the present invention provides uses of a krill oil composition in a human subject for improvement of cardiovascular disease risk factors, reduction of cannabinoid receptor signaling, reduction of appetite, reduction of fatty heart or reduction of fat accumulation.

In certain embodiments, the present invention provides uses of krill oil for the preparation of a medicament for improvement of cardiovascular disease risk factors, reduction in cannabinoid receptor signaling, reduction of appetite, or reduction of fat accumulation.

In certain embodiments, the present invention provides methods comprising providing a krill oil composition to a human subject; and administering the krill oil composition to the human subject under conditions such that the reproductive performance is increased. In some embodiments, reproductive performance is improved chance of ovulation in females. In some embodiments, reproductive performance is spermatogenesis, sperm motility and/or acreosome reaction.

In certain embodiments, the present invention provides methods comprising providing a krill oil composition to a human subject; and administering the krill oil composition to the human subject under conditions such the liver and/or kidney functions are improved.

Other novel features and advantages of the present invention will become apparent to those skilled in the art upon examination of the following or upon learning by practice of the invention.

DETAILED DESCRIPTION OF THE DRAWINGS

FIG. 1. $^{31}$P NMR analysis of polar lipids in krill oil.

Figure 2:
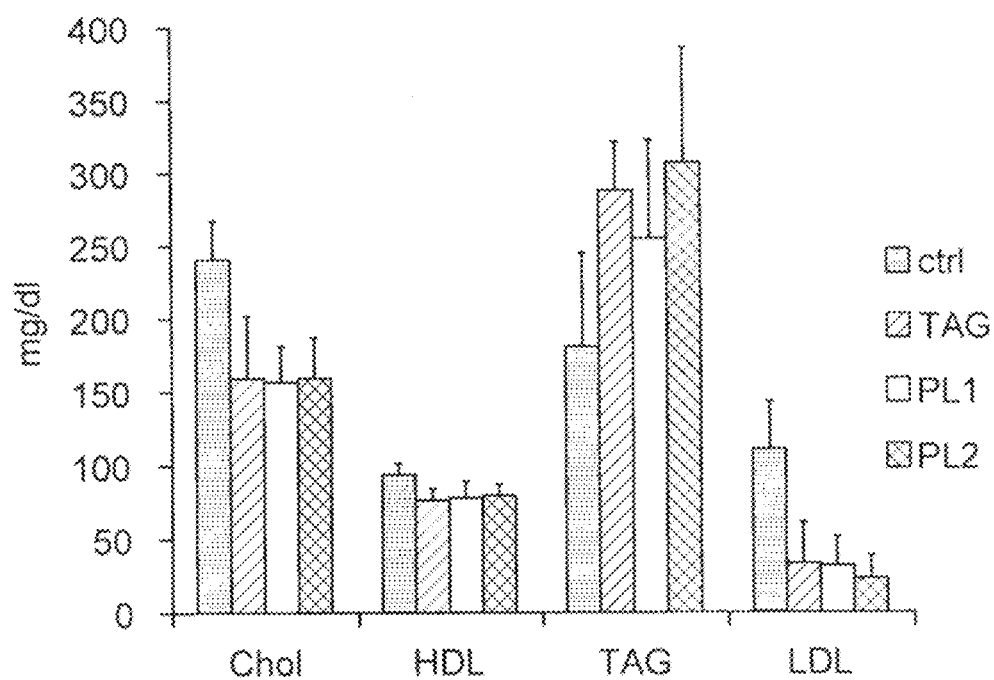

FIG. 2. Blood lipid profiles in Zucker rats fed different forms of omega-3 fatty acids (TAG=FO, PL1=NKO and PL2=Superba).

Figure 3:
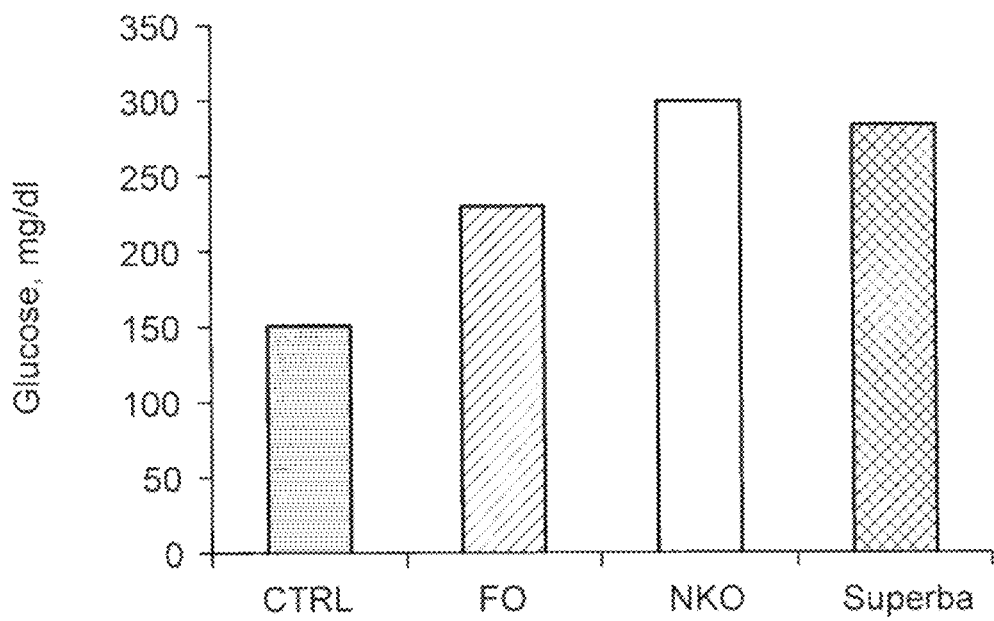

FIG. 3. Plasma glucose concentration in Zucker rats fed different forms of omega-3 fatty acids.

Figure 4:
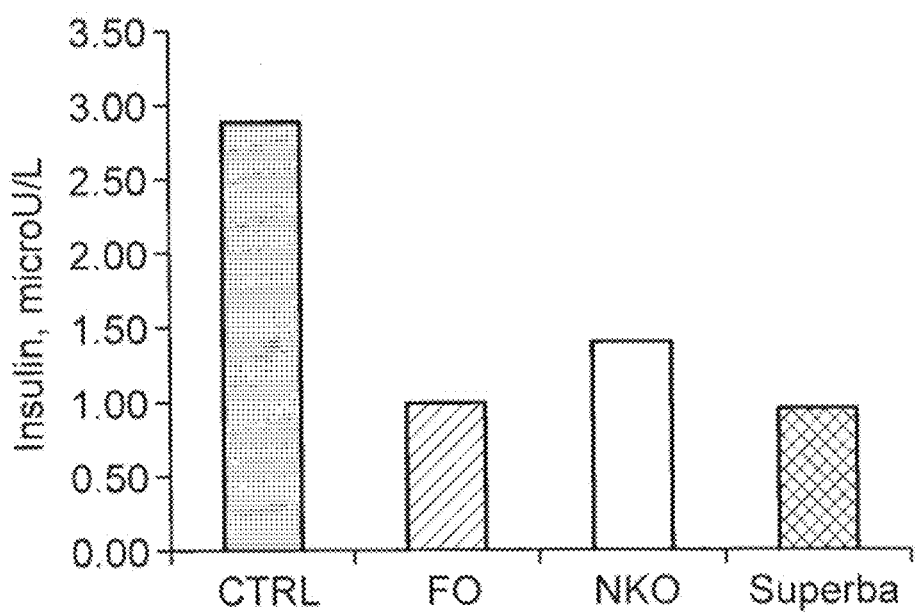

FIG. 4. Plasma insulin concentration in Zucker rats fed different forms of omega-3 fatty acids.

Figure 5:
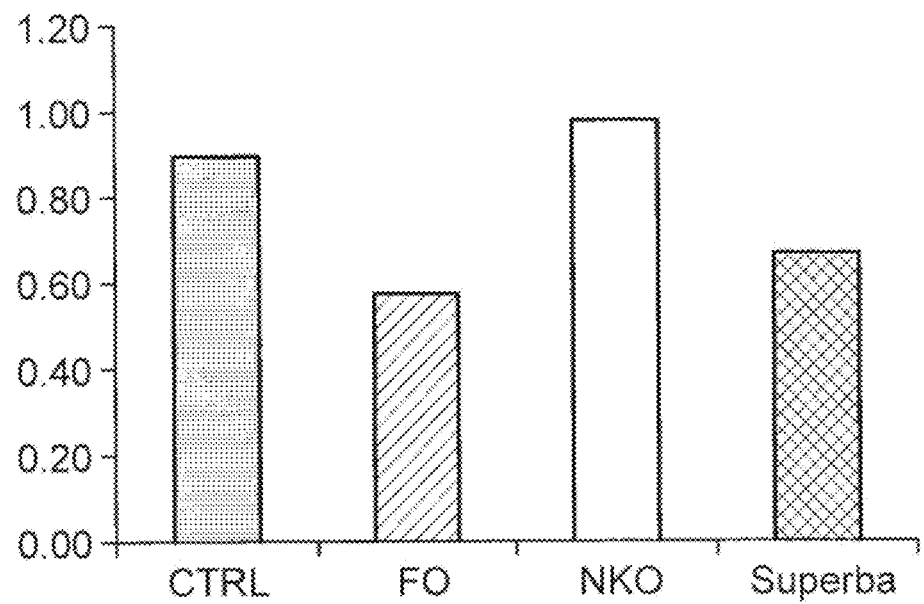

FIG. 5. Estimated HOMA-IR values in Zucker rats fed different forms of omega-3 fatty acids.

Figure 6:
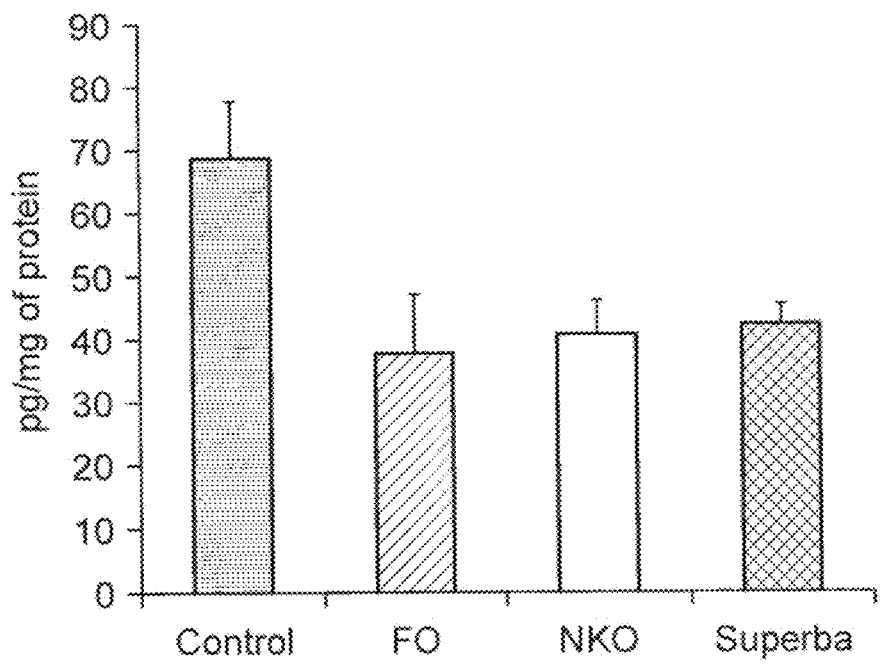

FIG. 6. The effect of dietary omega-3 fatty acids on TNF-α production by peritoneal macrophages.

Figure 7:
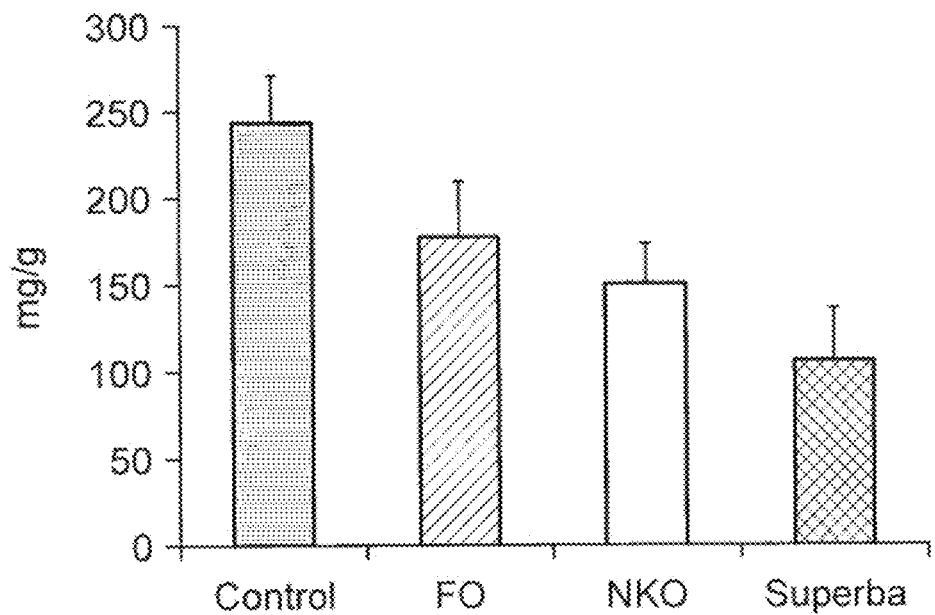

FIG. 7. The effect of dietary omega-3 fatty acids on lipid accumulation in the liver.

Figure 8:
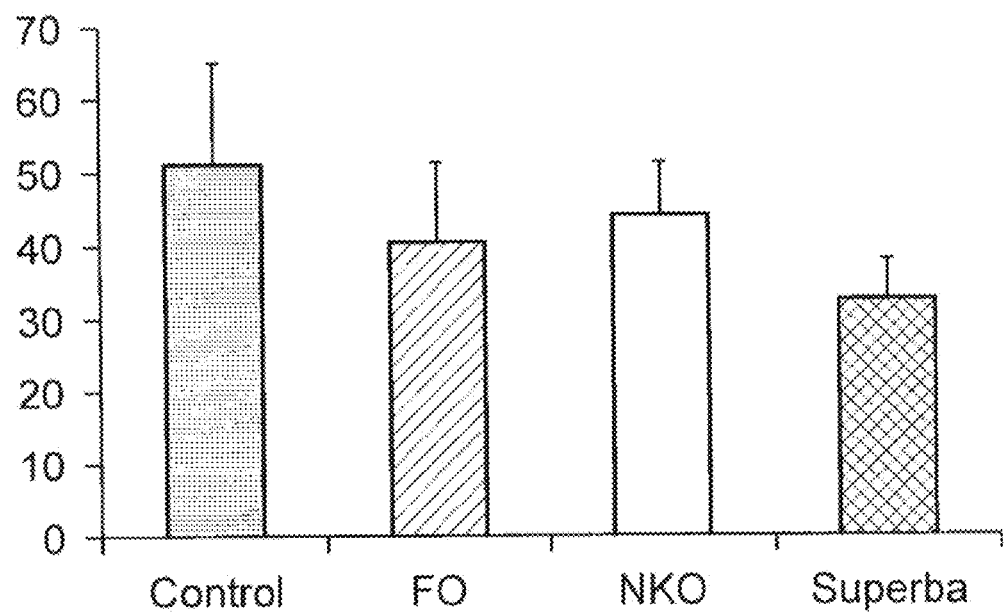

FIG. 8. The effect of dietary omega-3 fatty acids on lipid accumulation in the muscle.

Figure 9:
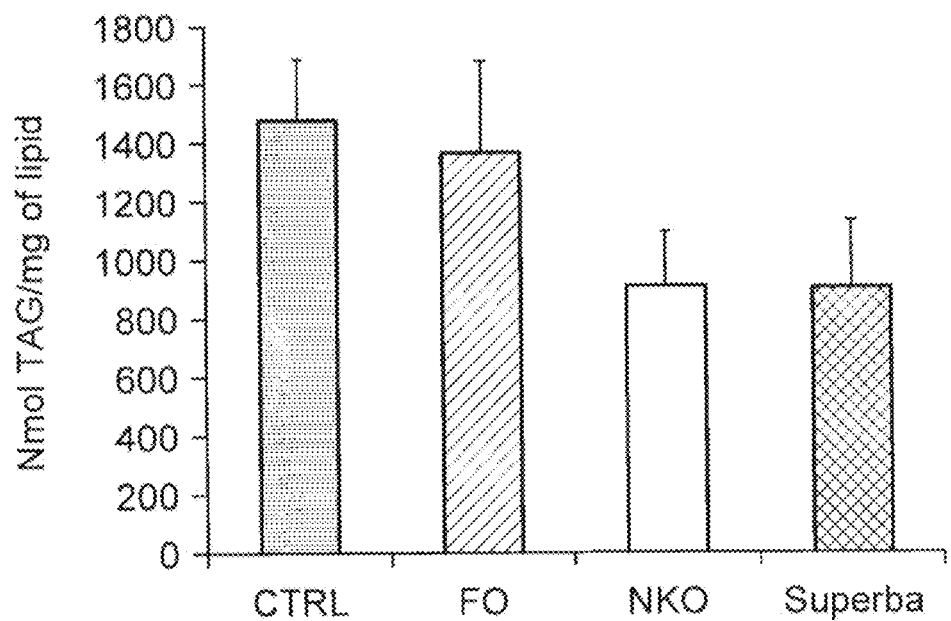

FIG. 9. The effect of dietary omega-3 fatty acids on lipid accumulation in the heart.

Figure 10:
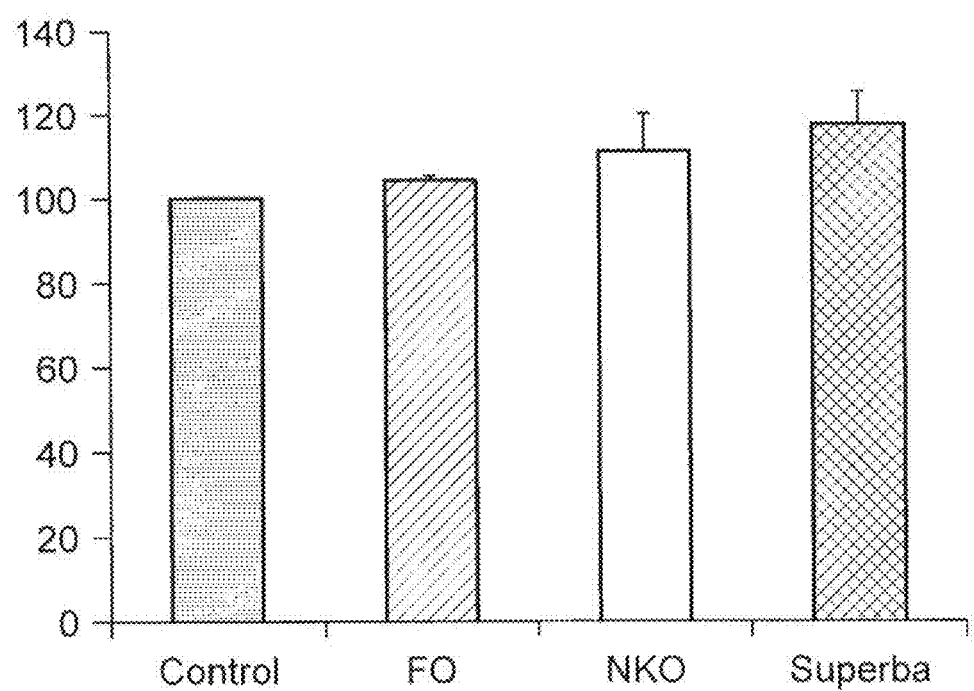

FIG. 10. Relative concentrations of DHA in the brain in Zucker rats supplemented with omega-3 fatty acids.

Figure 11:
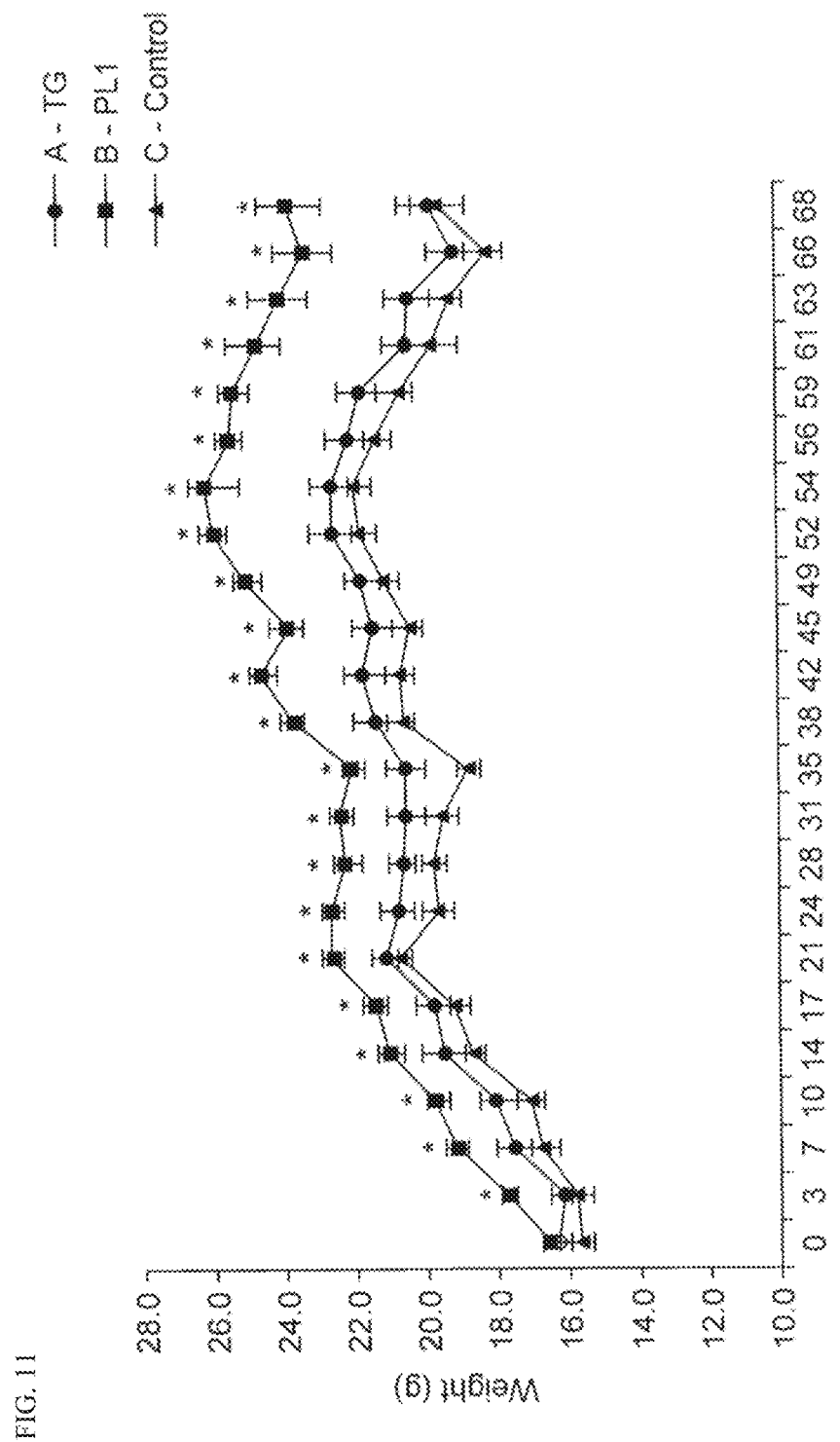

FIG. 11. Mean group body weights (g) in the collagen-induced male DBA/1 arthritic mice. B-PL2 is the krill oil group. *p<0.05, significantly different from Group A (Positive Control-Fish Oil) and Group C (Control).

Figure 12:
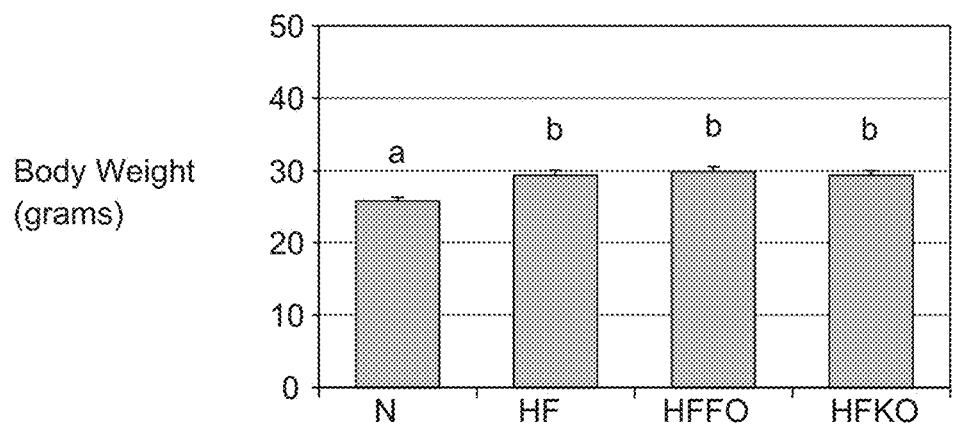

FIG. 12. Body weight for the various treatment groups.

Figure 13:
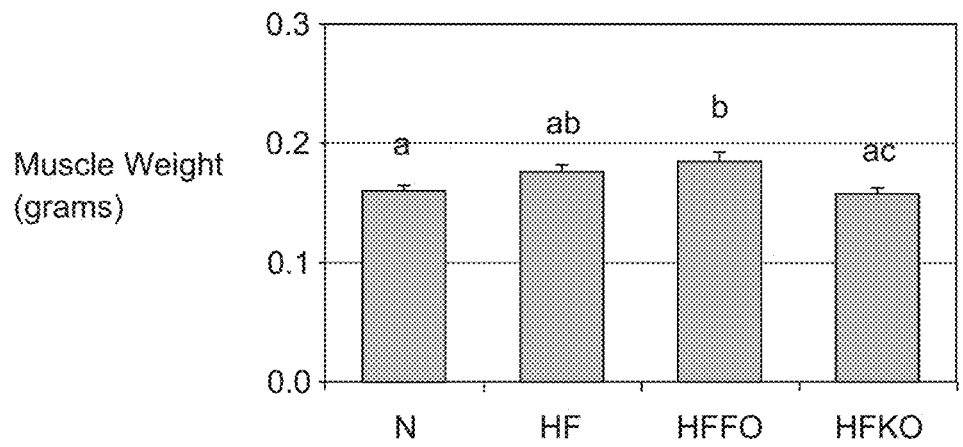

FIG. 13. Muscle weight for the various treatment groups.

Figure 14:
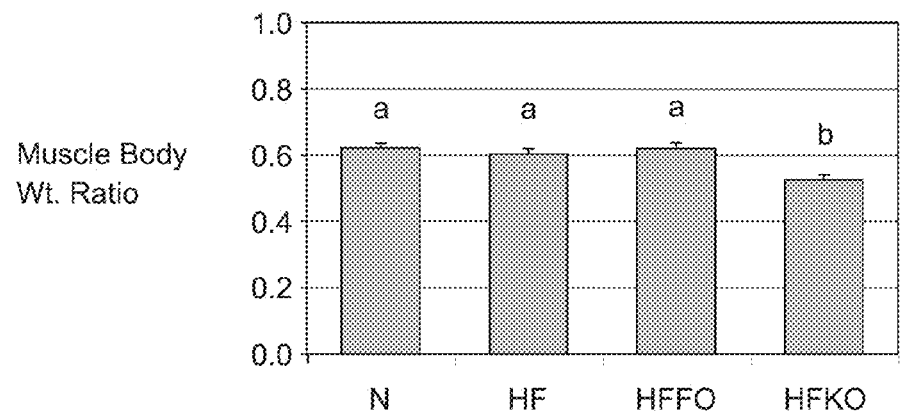

FIG. 14. Muscle to body weight ratio for the various treatment groups.

Figure 15:
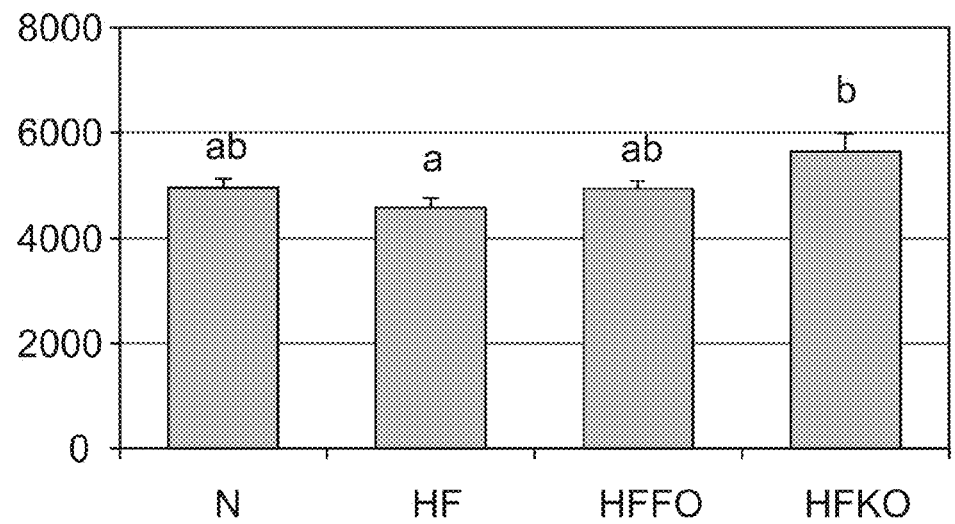

FIG. 15. Serum adiponectin levels (ng/ml) for the various treatment groups.

Figure 16:
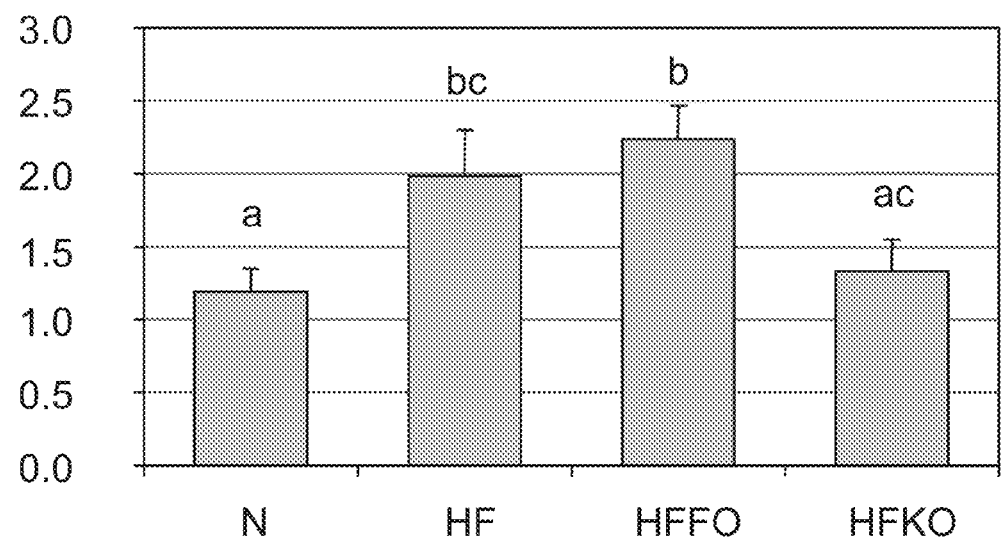

FIG. 16. Serum insulin levels for the various treatment groups.

Figure 17:
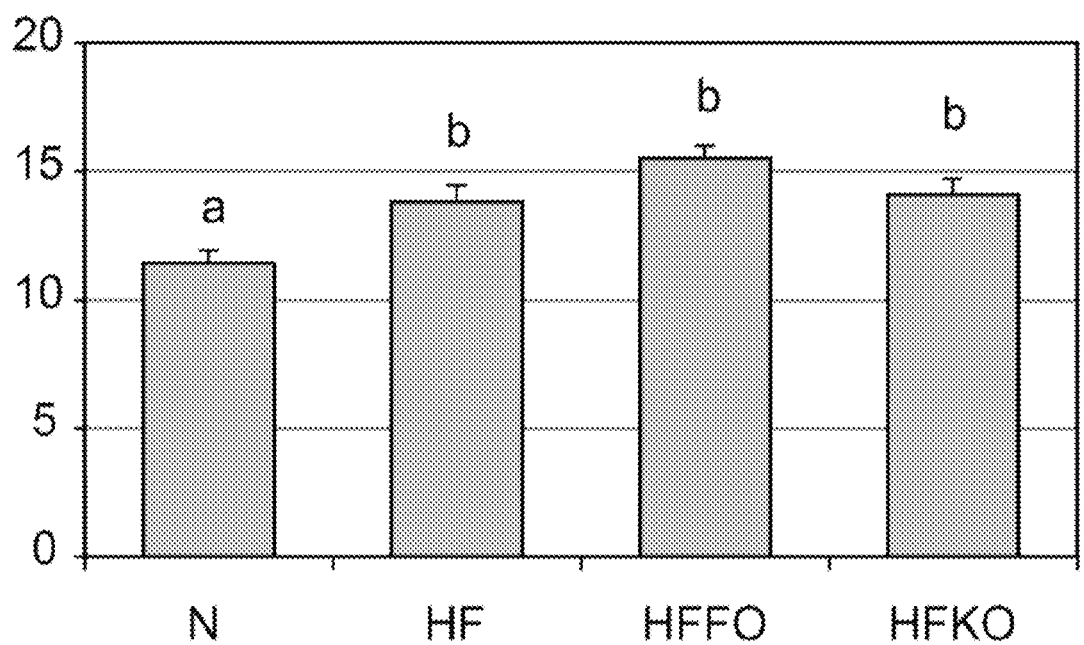

FIG. 17. Blood glucose (mmll/l) levels in the various treatment groups.

Figure 18:
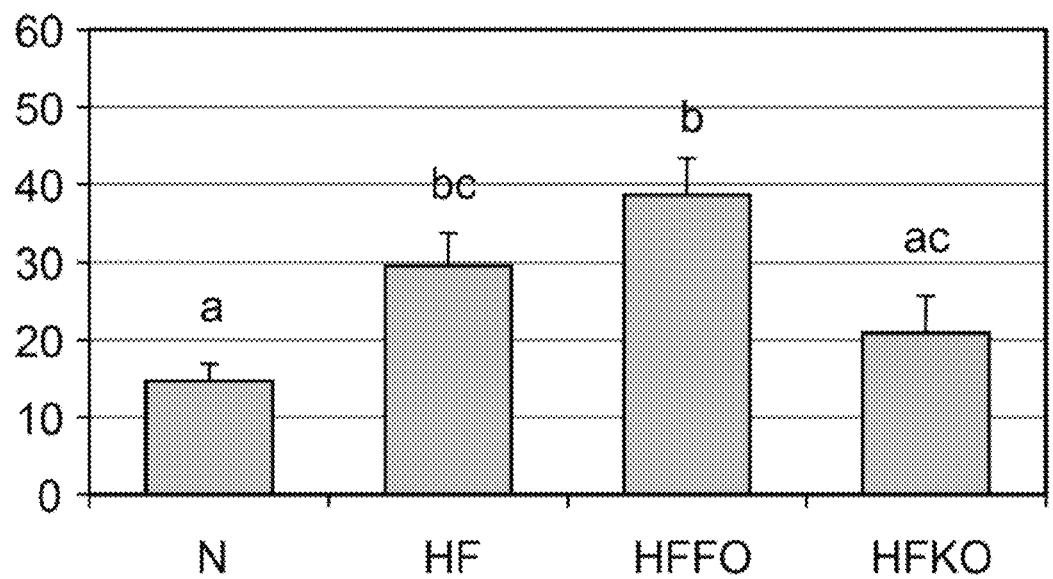

FIG. 18. HOMA-IR values for the various treatment groups.

Figure 19:
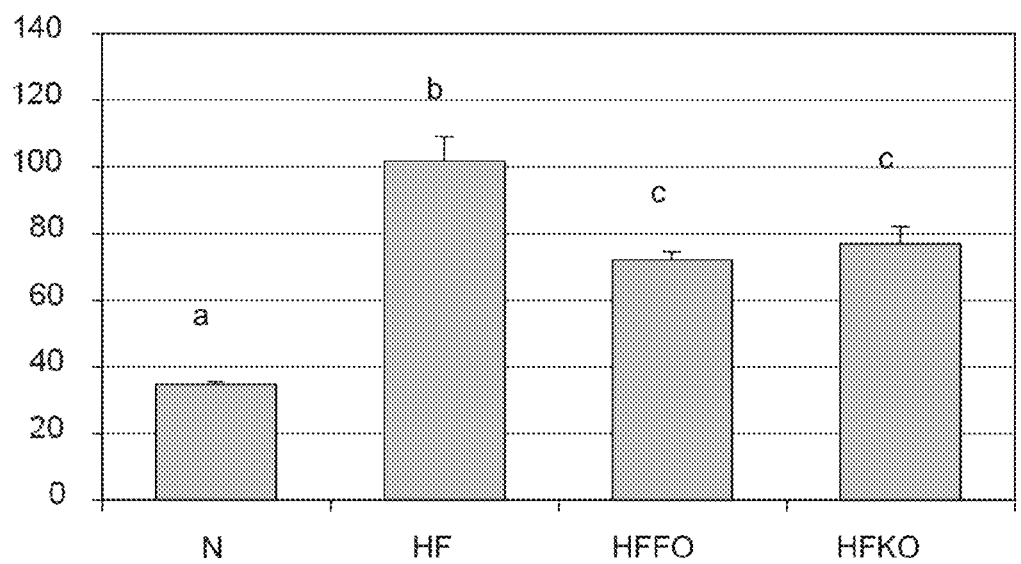

FIG. 19. Liver triglyceride levels (µmol/g) for the various treatment groups.

Figure 20A:
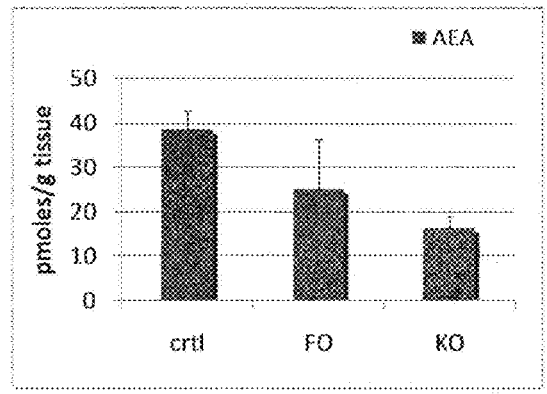
Figure 20B:
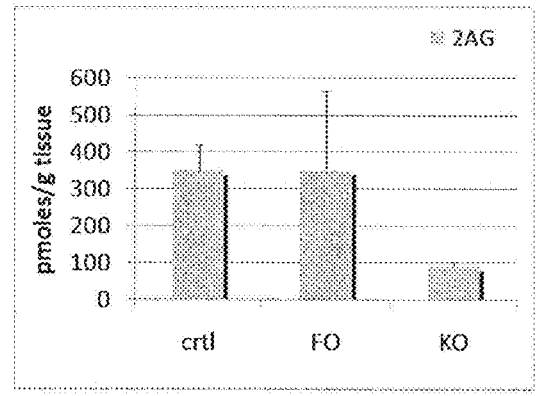

FIG. 20A-B. Levels of anandamide (arachidonoyl ethanolamide) and 2-arachidonoyl glycerol in visceral adipose tissue in Zucker rats.

Figure 21A:
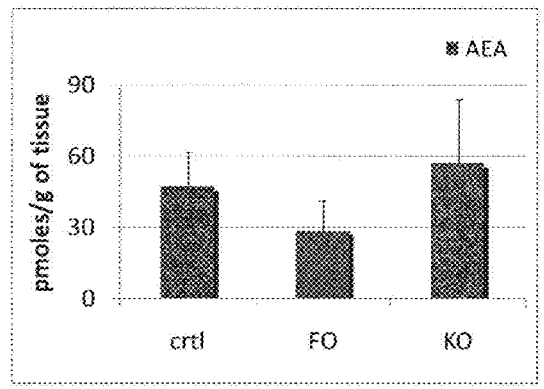
Figure 21B:
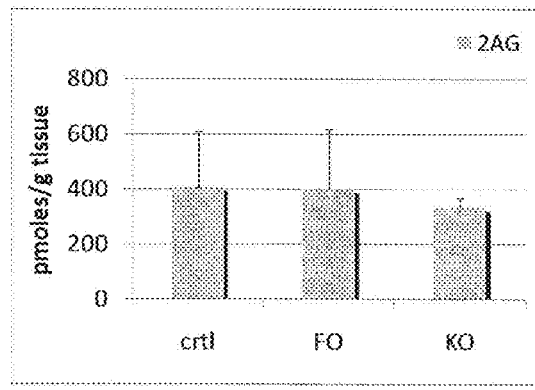

FIG. 21A-B. Levels of anandamide (arachidonoyl ethanolamide) and 2-arachidonoyl glycerol in subcutaneous adipose tissue in Zucker rats.

Figure 22A:
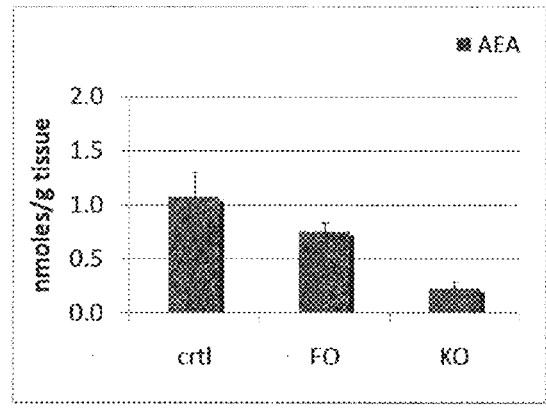
Figure 22B:
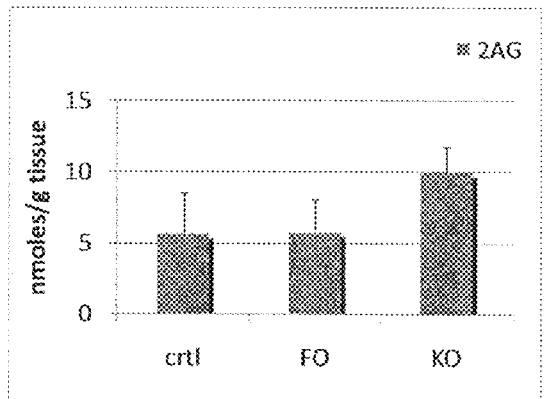

FIG. 22A-B. Levels of anandamide (arachidonoyl ethanolamide) and 2-arachidonoyl glycerol in liver tissue in Zucker rats.

Figure 23A:
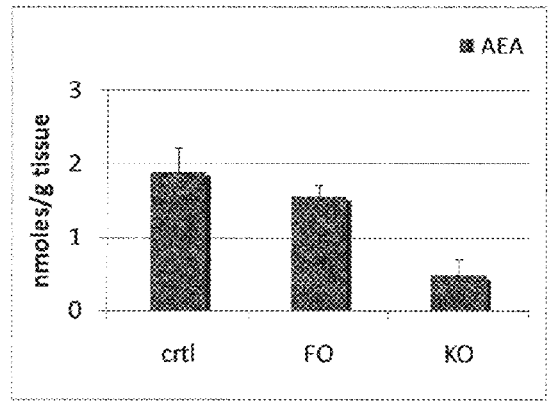
Figure 23B:
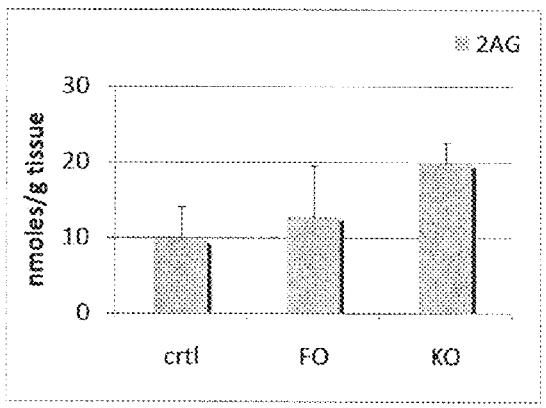

FIG. 23A-B. Levels of anandamide (arachidonoyl ethanolamide) and 2-arachidonoyl glycerol in heart tissue in Zucker rats.

Figure 24:
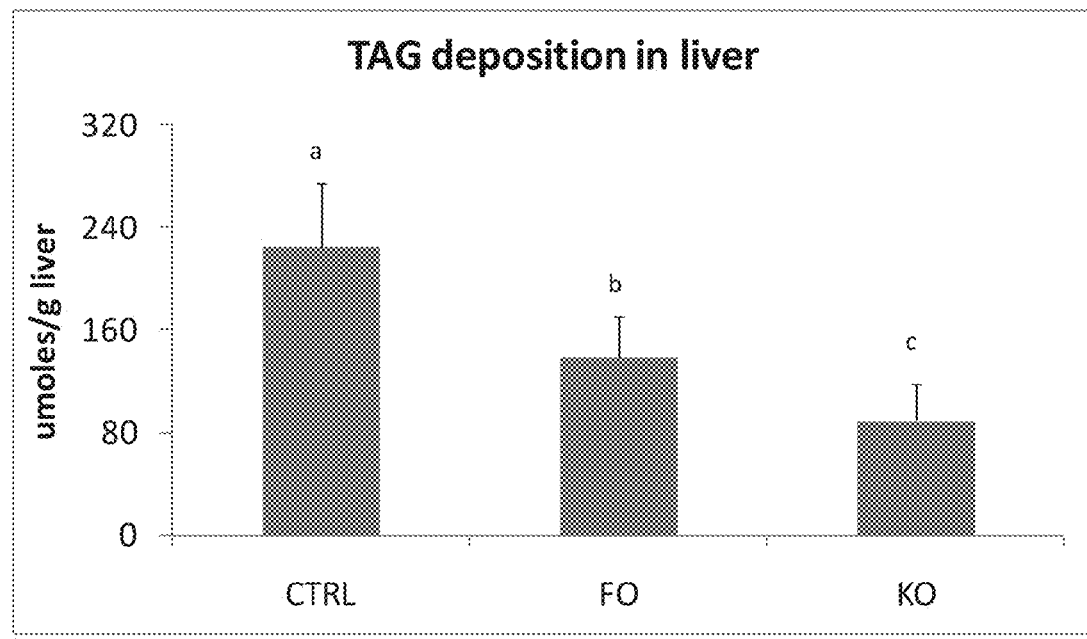

FIG. 24. Triacylglyceride content in liver.

Figure 25:
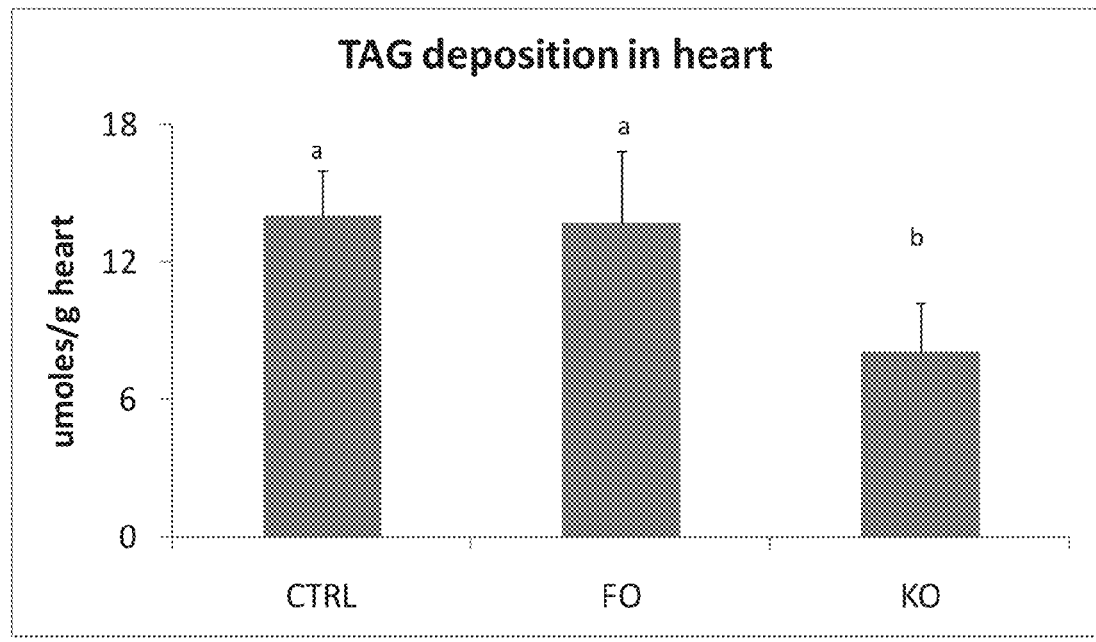

FIG. 25. Triacylglyceride content in heart.

Figure 26:
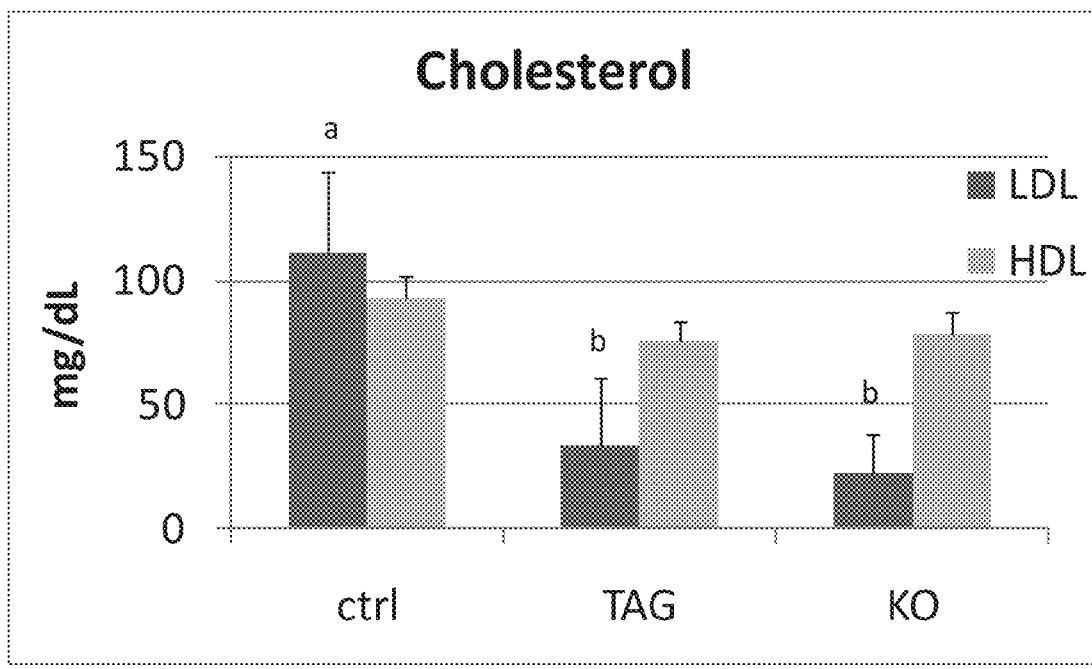

FIG. 26. Cholesterol profile in plasma.

Figure 27:
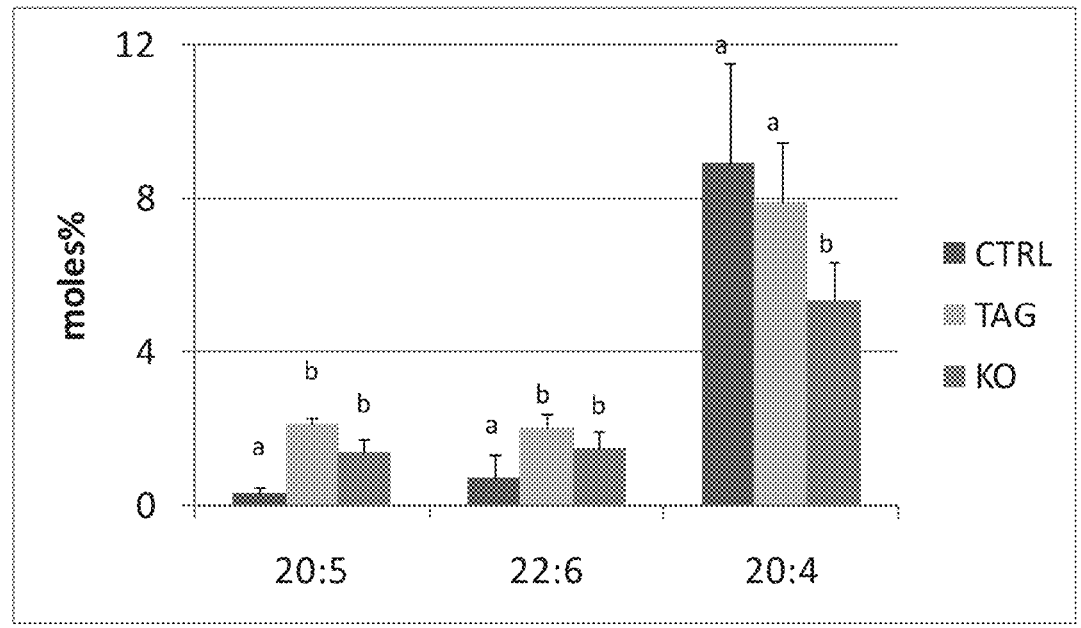

FIG. 27. Fatty acid analyses of monocytes.

Figure 28:
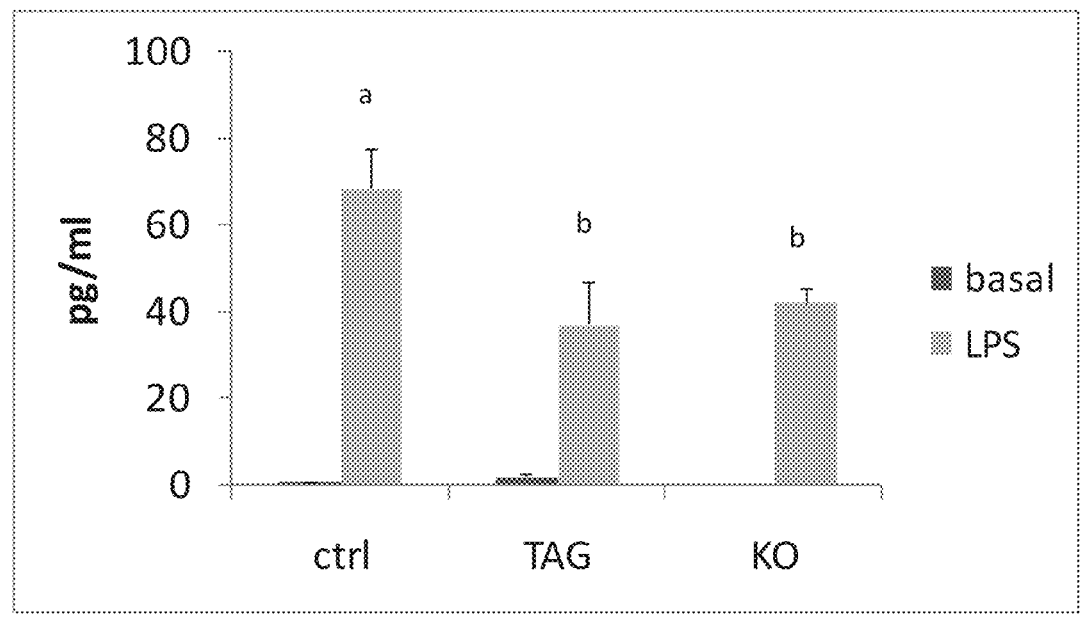

FIG. 28. TNF alpha release in peritoneal monocytes after ex vivo challenge with LPS.

Figure 29A:
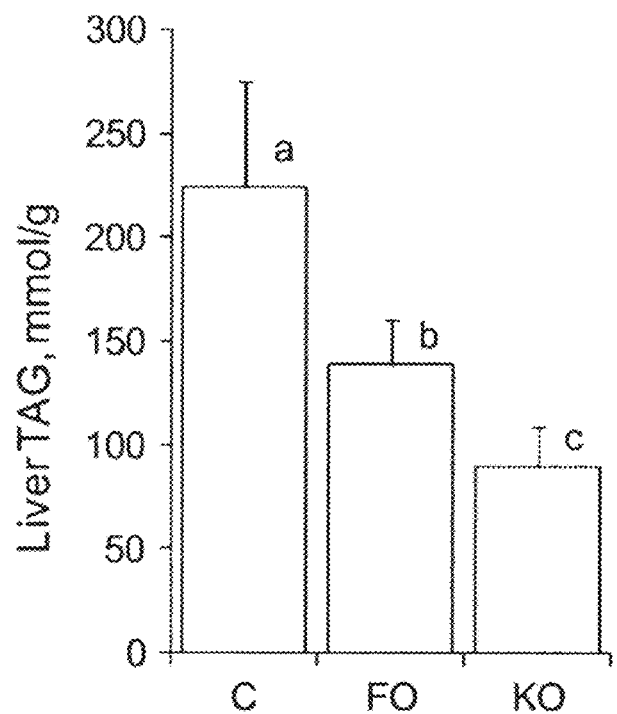
Figure 29B:
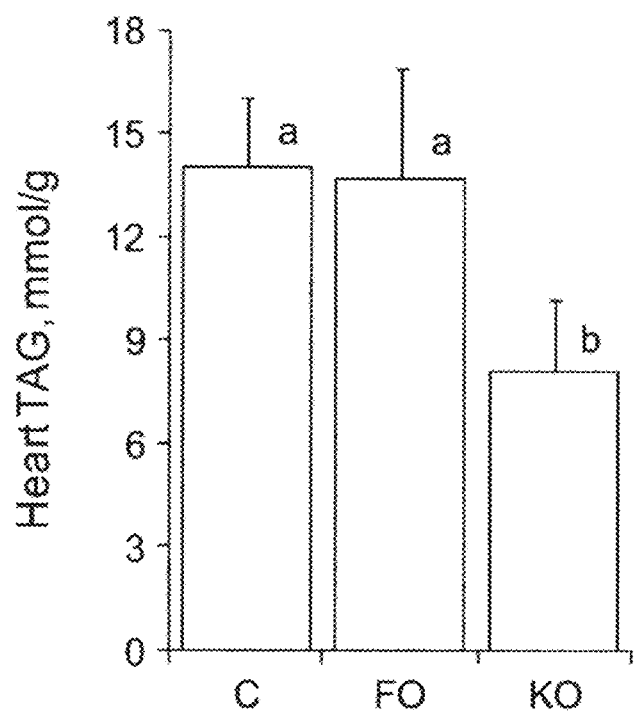

FIG. 29A-B. Liver (A) and heart (B) triacyiglycerol concentrations of obese Zucker rats fed control, fish oil, or krill oil diets for four weeks. Values are expressed as mean+/−SD, n=6. Means that do not have a common letter differ, P<0.05.

Figure 30A:
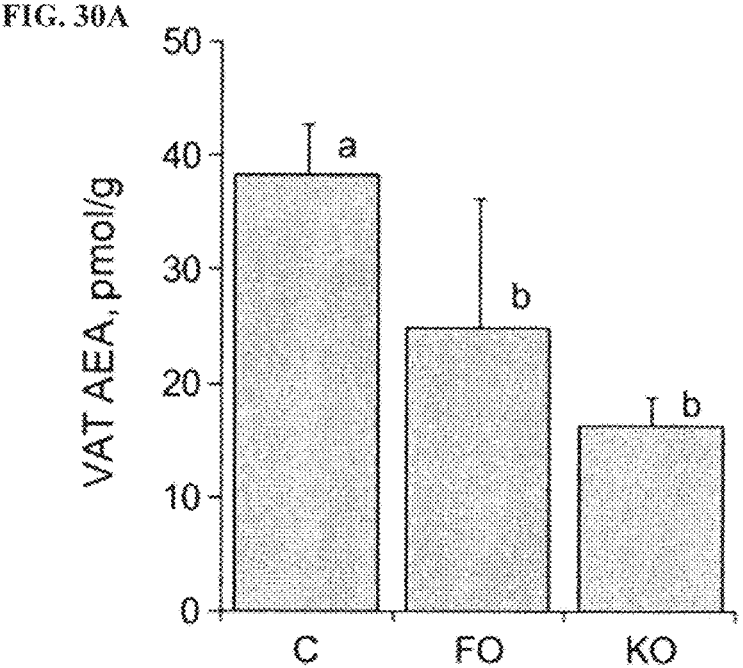
Figure 30B:
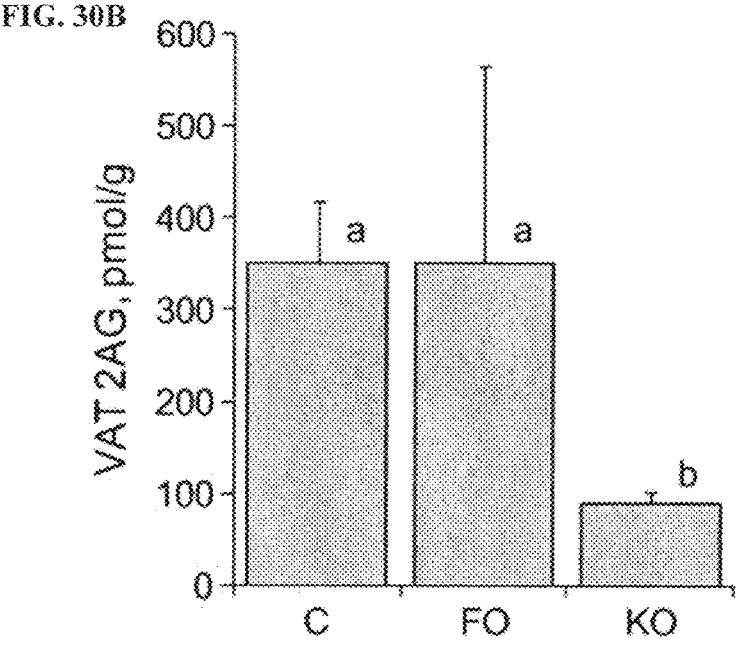
Figure 31A:
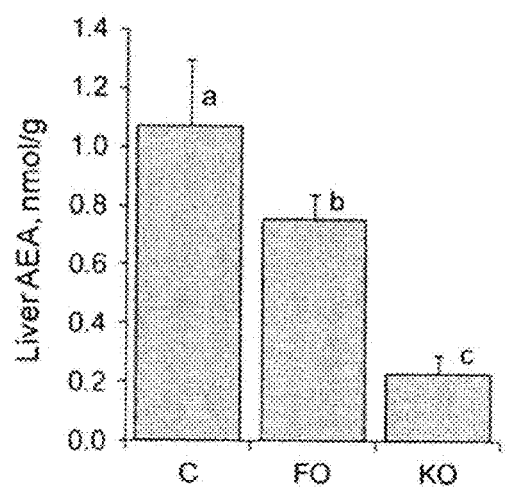
Figure 31B:
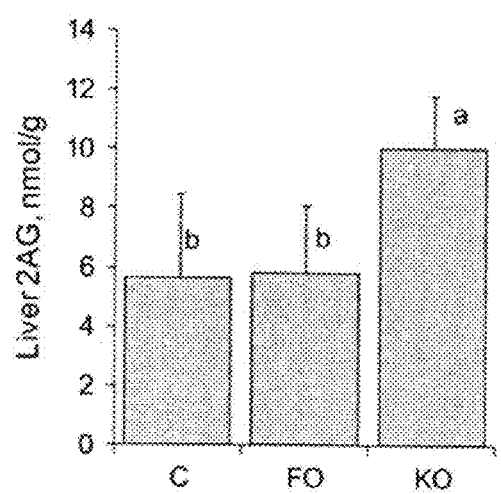
Figure 31C:
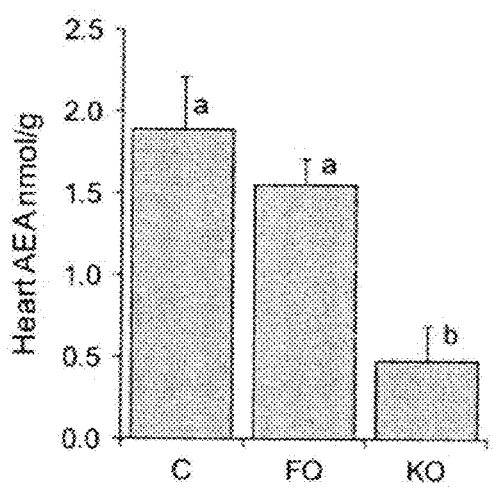
Figure 31D:
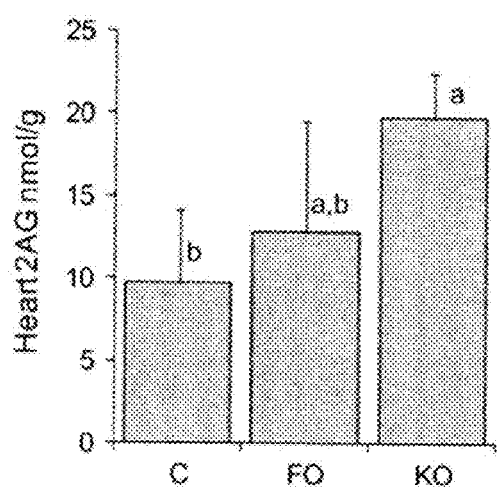

FIG. 30A-B. Visceral AEA (A) and 2-AG (B) concentrations in obese Zucker rats fed control, fish oil, or krill oil diets for four weeks. Values are expressed as mean+/−SD, n=6. Means that do not have a common letter differ, P<0.05.

FIG. 31A-D. Liver (A and B) and heart (C and D) AEA (A and C) and 2-AG (B and D) concentrations in rats fed control, fish oil, or krill oil diets for four weeks. Values are expressed as mean+/−SD, n=6. Means that do not have a common number differ, P<0.05.

Figure 32A:
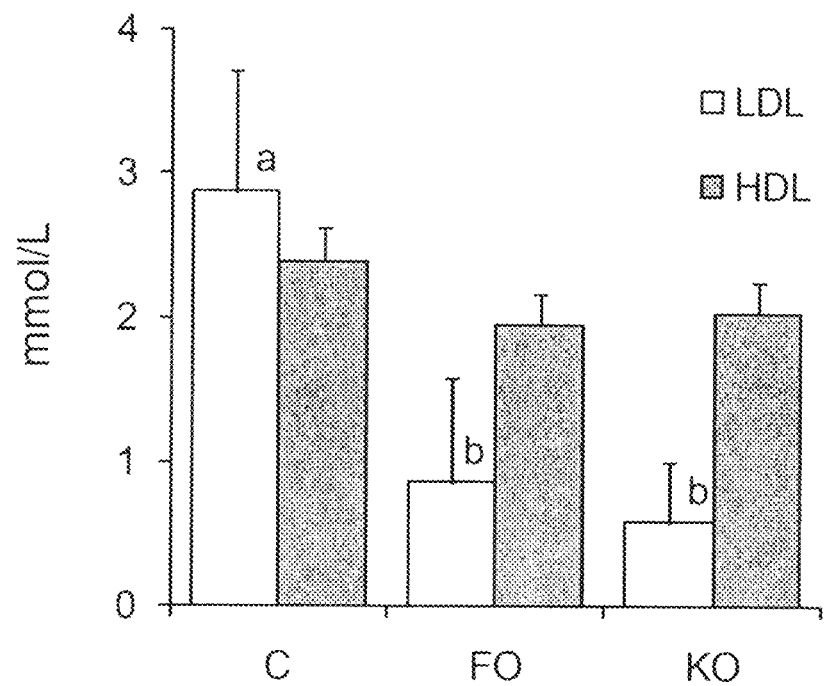
Figure 32B:
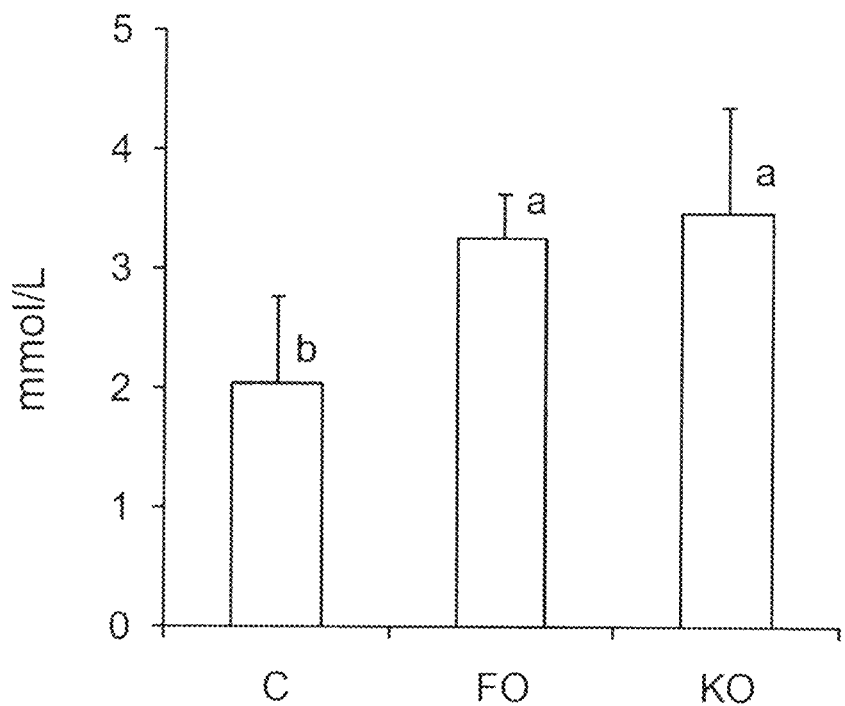

FIG. 32A-B. Cholesterol (A) and TAG (B) concentrations in plasma from rats fed control (C), fish oil (FO), or krill oil (KO) diets. Error bars depict S.D., n=6. Different letters denote significant differences (p<0.05)

Figure 33:
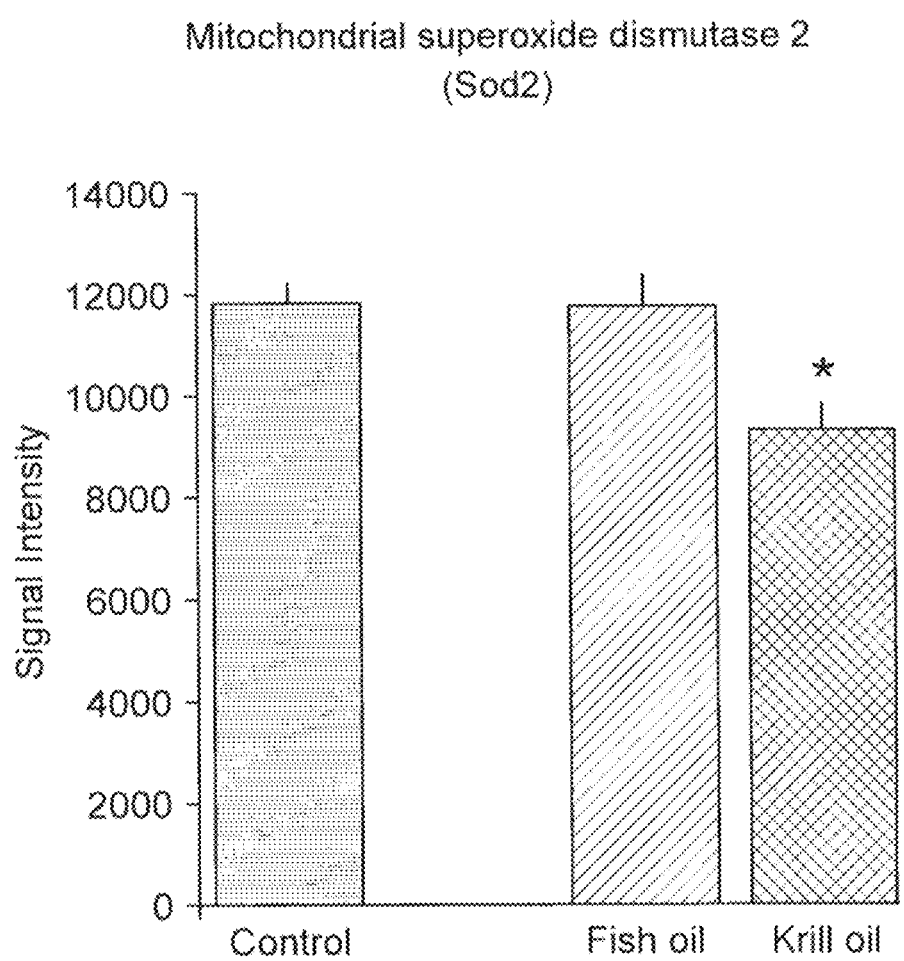

FIG. 33. Treatment-induced changes in the expression of the mitochondrial reactive oxygen species detoxification enzyme Sod2. Expression was significantly decreased by a KO diet.

Figure 34:
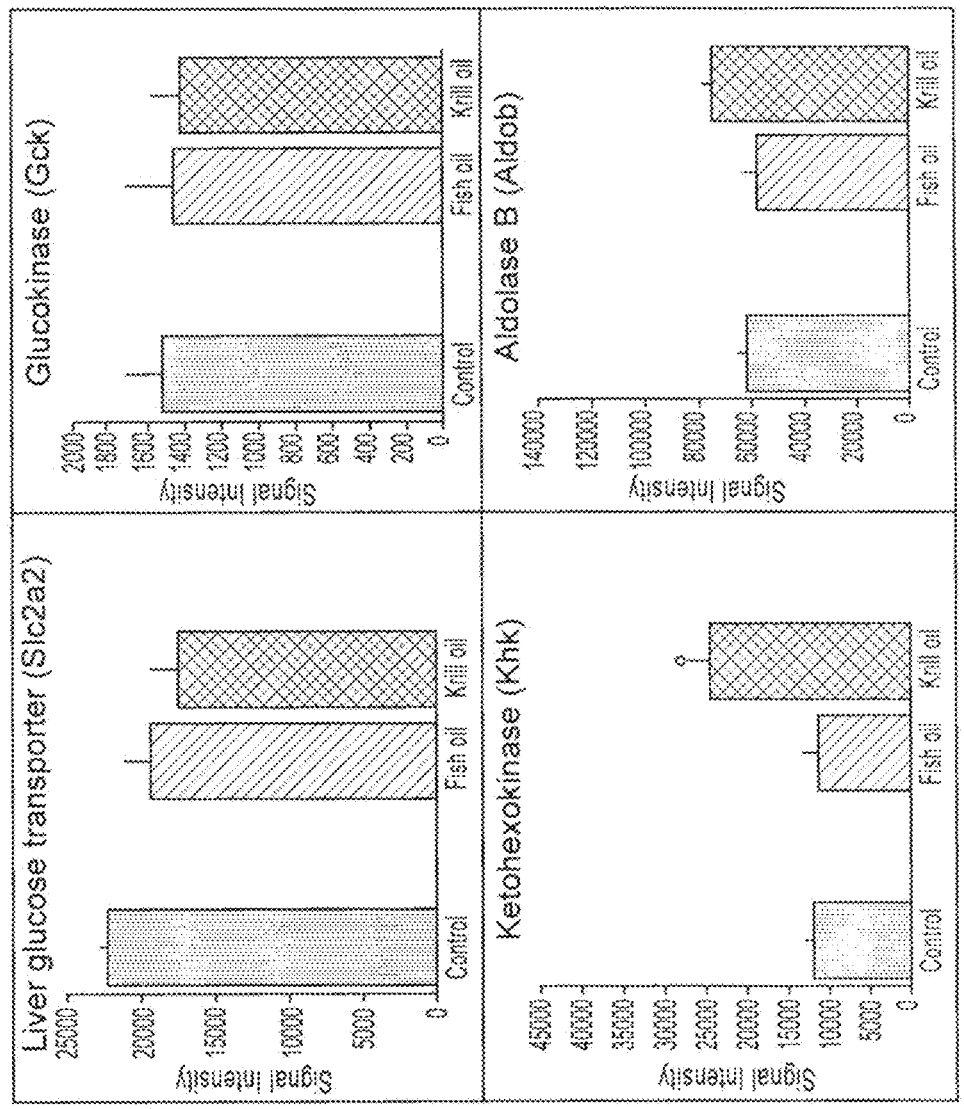

FIG. 34. Genes suggesting decreased glucose uptake and increased fructose metabolism. KO diet showed a trend for increased Aldob expression (p=0.022)

Figure 35:
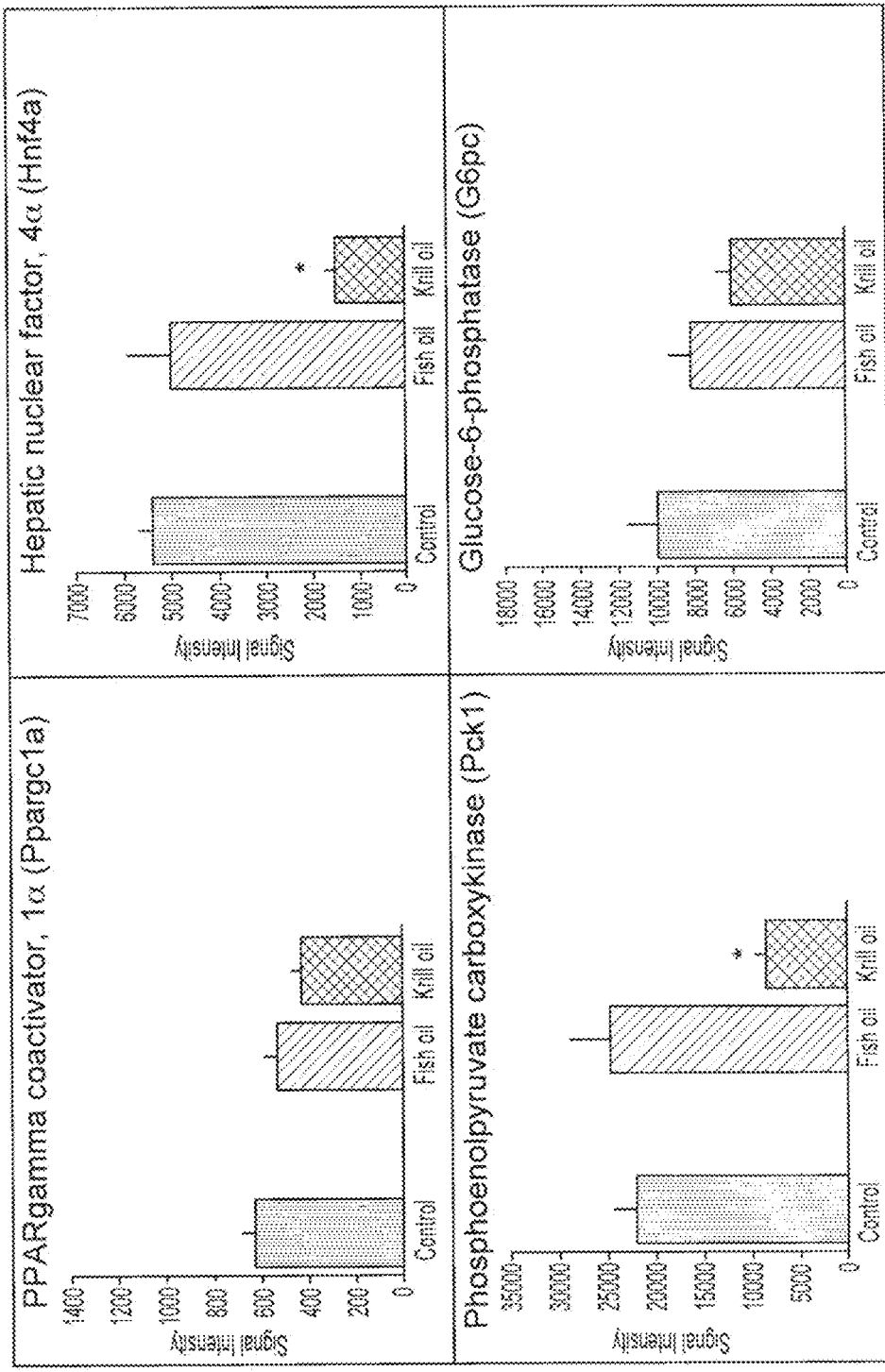

FIG. 35. Key genes regulating hepatic glucose production

Figure 36:
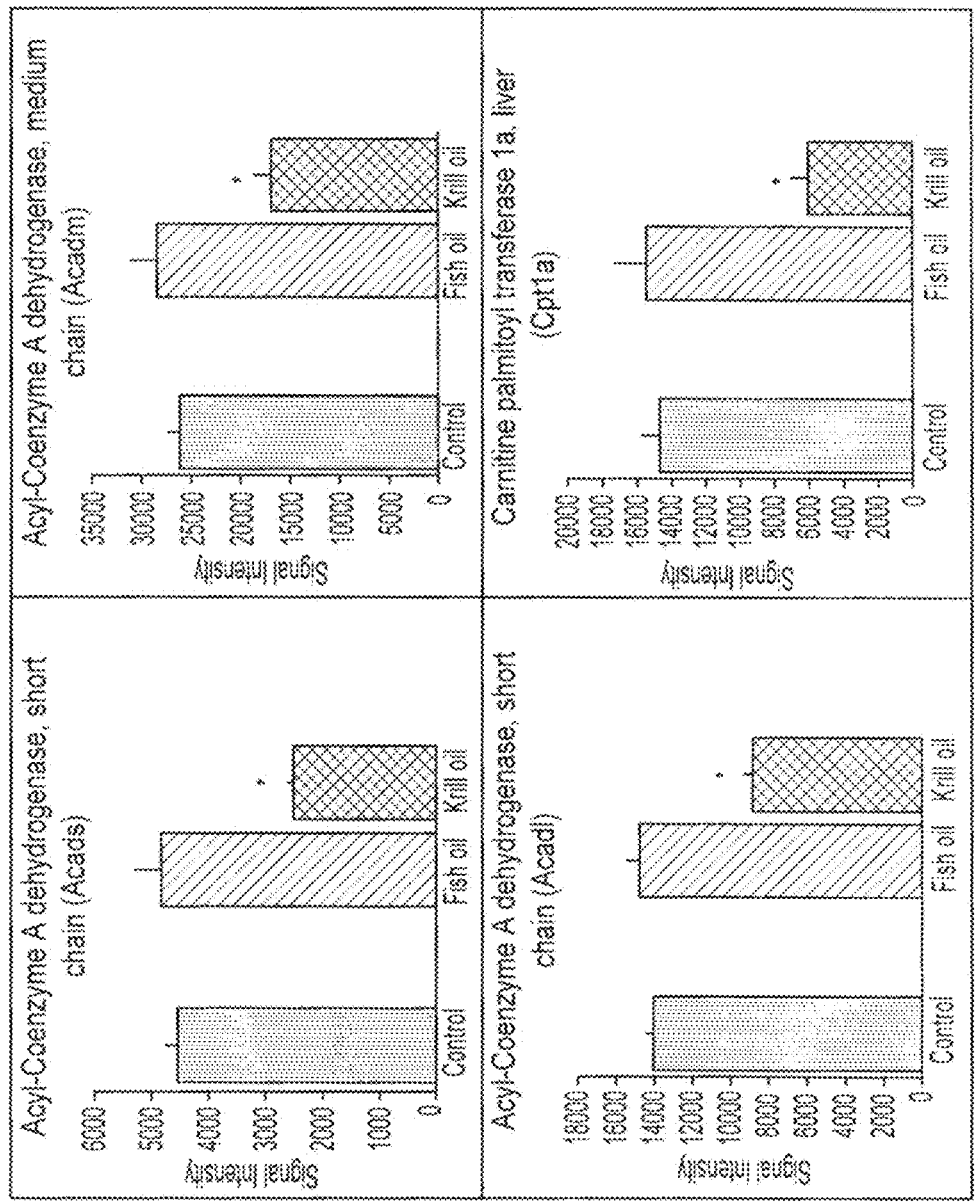

FIG. 36. Key genes involved in fatty acid metabolism.

Figure 37:
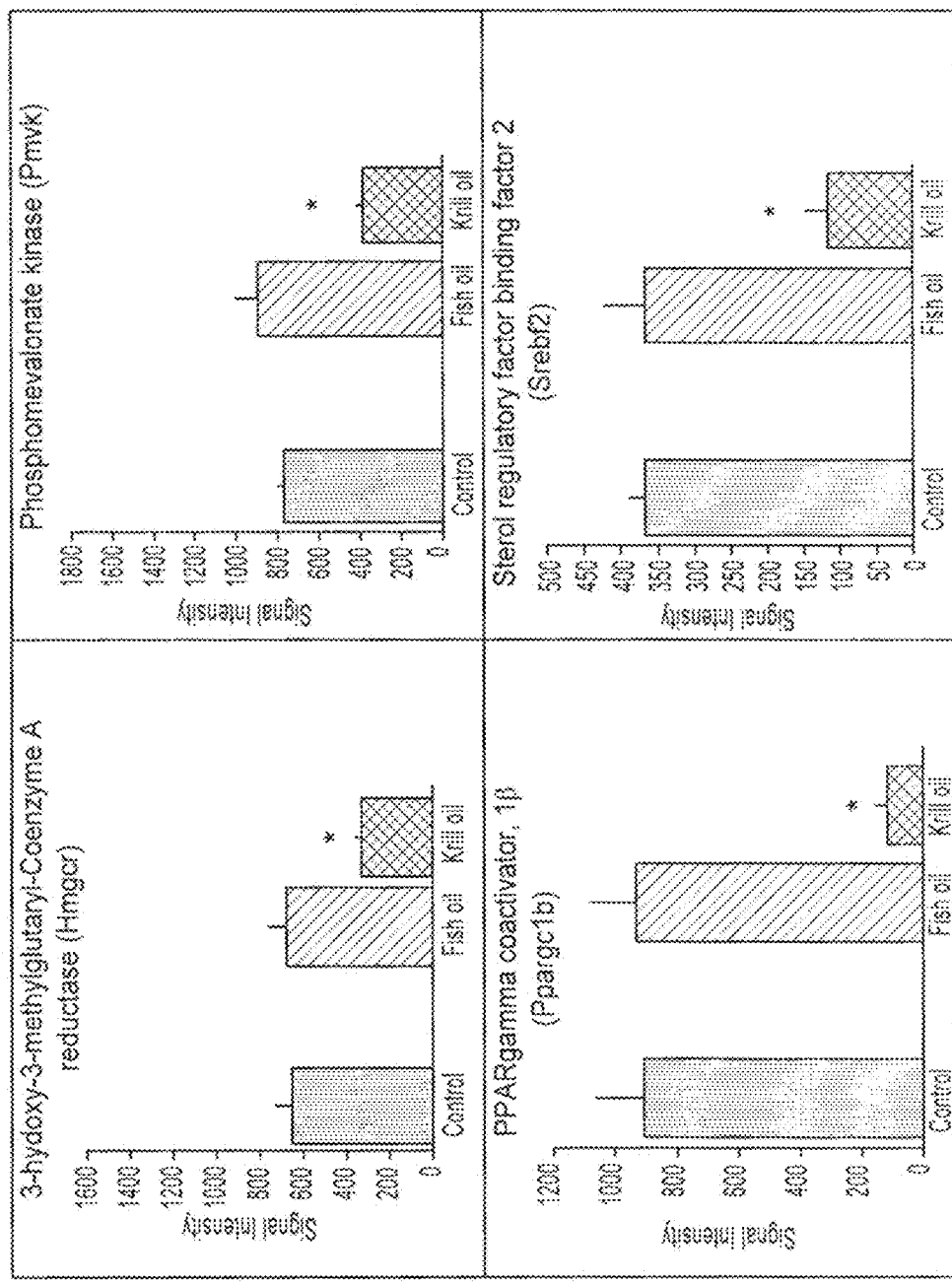

FIG. 37. Key genes regulating cholesterol biosynthesis in the liver 3-hydroxy-3-methylglutaryl-Coenzyme A FIG. 38. Transcriptional cofactors and gene targets proposed to mediate the effect of krill-supplements on hepatic glucose metabolism and lipid biosynthesis.

DEFINITIONS

An "ether phospholipid" as used herein preferably refers to a phospholipid having an ether bond at position 1 of the glycerol backbone. Examples of ether phospholipids include, but are not limited to, alkylacylphosphatidylcholine (AAPC), lyso-alkylacylphosphatidylcholine (LAAPC), and alkylacylphosphatidylethanolamine (AAPE). A "non-ether phospholipid" is a phospholipid that does not have an ether bond at position 1 of the glycerol backbone.

As used herein, the term "omega-3 fatty acid" refers to polyunsaturated fatty acids that have the final double bond in the hydrocarbon chain between the third and fourth carbon atoms from the methyl end of the molecule. Non-limiting examples of omega-3 fatty acids include, 5,8,11,14,17-eicosapentaenoic acid (EPA), 4,7,10,13,16,19-docosahexaenoic acid (DHA) and 7,10,13,16,19-docosapentaenoic acid (DPA).

As used herein, the term "w/w (weight/weight)" refers to the amount of a given substance in a composition on weight basis. For example, a composition comprising 50% w/w phospholipids means that the mass of the phospholipids is 50% of the total mass of the composition (i.e., 50 grams of phospholipids in 100 grams of the composition, such as an oil).

DETAILED DESCRIPTION OF THE INVENTION

The present invention relates to methods of using krill oil and/or compositions comprising krill oil to treat risk factors for metabolic, cardiovascular, and inflammatory disorders, including, but not limited to, modulating endocannabinoid concentrations; reducing ectopic fat; reducing triacylglycerides in the liver and heart; reducing monoacylglyceride lipase activity in the visceral adipose tissue, liver, and heart; increasing levels of DHA in the liver; increasing the levels of EPA and DHA in the phospholipid fractions of tissues that exhibit changes in endocannabinoid concentration; reducing susceptibility to inflammation, modulating glucose and lipid homeostasis; reducing fatty liver disease (alcoholic and non-alcoholic); reducing MAGL activity in the heart; increasing levels of plasma ALA/LA; decreasing levels of ALA/LA in the heart; decreasing levels of ARA in the subcutaneous adipose tissue; and decreasing availability of substrates to decrease the activity of the endocannabinoid system.

The present invention also relates to method of using krill oil and/or compositions comprising krill oil to modulate biological processes selected from the group consisting of glucose metabolism, lipid biosynthesis, fatty acid metabolism, cholesterol biosynthesis, and the mitochondrial respiratory chain.

The present invention further includes pharmaceutical and/or nutraceutical formulations made from krill oil, methods of making such formulations, and methods of administering them to treat risk factors for metabolic, cardiovascular, and inflammatory disorders.

A. Methods of Using Krill Oil

The present invention relates to methods of using krill oil and compositions comprising krill oil to treat one or more risk factors for metabolic, cardiovascular, and inflammatory disorders. There are a variety of risk factors associated with metabolic, cardiovascular, inflammatory, and other disorders, and it has been found in accordance with the present invention that krill oil significantly modulates a substantial number of risk factors associated with metabolic, cardiovascular, inflammatory and other disorders. These disorders may include, but are not limited to, obesity, type II diabetes, type I diabetes, gestational diabetes, metabolic syndrome, dyslipidemia, hypercholesterolemia, hypertension, coronary artery disease, atherosclerosis, stroke, rheumatoid arthritis, and osteoarthritis.

The level(s) of the risk factor(s) to be treated may be assessed in one or more body fluids of interest, including, but not limited to, blood, plasma, urine, sweat, tears, and cerebrospinal fluid. The level(s) of the risk factor(s) may also be assessed in one or more organs of interest, including, but not limited to, the brain, heart, liver, blood vessels, visceral adipose tissue (VAT), subcutaneous adipose tissue (SAT), lungs, intestines, blood vessels, lymph nodes, kidneys, and pancreas.

Specific risk factors that may be modulated by the krill oil-based compositions in the methods of the present invention include endocannabinoid concentrations (particularly AEA (N-arachidonoylethanolamine (anandamide)) and 2-AG (2-arachidonoylglycerol) in the liver, heart, and VAT, although the present invention is not limited to these endocannabinoids); ectopic fat; triacylglycerides in the liver and heart; monoacylglyceride lipase activity in the VAT, liver, and heart; susceptibility to inflammation, glucose and lipid homeostasis; fatty liver disease (alcoholic and non-alcoholic); MAGL (monoacylglycerol lipase) activity in the heart; levels of ALA/LA (alpha-linolenic acid/linoleic acid) in the heart; levels of ARA (arachidonic acid) in the SAT; and availability of substrates to decrease the activity of the endocannabinoid system. According to certain aspects of the invention, the levels or concentrations of these risk factors are decreased in a subject suffering from or at risk for a metabolic, cardiovascular, or inflammatory disorder by administering a krill oil composition. According to other aspects of the invention, the levels or concentrations of these risk factors are decreased in a patient population, by administering a krill oil composition to a patient population including individuals suffering from or at risk for a metabolic, cardiovascular, or inflammatory disorder. According to some aspects of the invention, a krill oil composition may be administered to a subject or patient population in accordance with methods for reducing levels of one or more of these risk factors relative to the level of expression or activity seen in an individual or population not suffering from a metabolic, cardiovascular, inflammatory disorder.

Other risk factors that modulated by the krill-based compositions in the methods of the present invention include levels of DHA (docosahexaenoic acid) in the liver; levels of EPA (eicosapentaenoic acid) and DHA in the phospholipid fractions of tissues that exhibit changes in endocannabinoid concentration; and levels of plasma ALA/LA. According to certain aspects of the invention, the levels or concentrations of these risk factors are increased in a subject suffering from or at risk for a metabolic, cardiovascular, or inflammatory disorder by administering a krill oil composition. According to other aspects of the invention, the levels or concentrations of these risk factors are increased in a patient population, by administering a krill oil composition to a patient population including individuals suffering from or at risk for a metabolic, cardiovascular, or inflammatory disorder. According to some aspects of the invention, a krill oil composition may be administered to a subject or patient population in accordance with methods for increasing levels of one or more of these risk factors relative to the level of expression or activity seen in an individual or population not suffering from a metabolic, cardiovascular, inflammatory disorder.

Biological processes that may be modulated by krill oil and compositions containing krill oil in the methods of the present invention include glucose metabolism, gluconeogenesis, lipid biosynthesis, fatty acid metabolism, cholesterol biosynthesis, and the mitochondrial respiratory chain. These biological processes are affected by expression of a number of genes, including, but not limited to, reduced or decreased expression of Ppargc1a (peroxisome proliferator-activated receptor gamma coactivator 1a), Hnf4a (hepatocyte nuclear factor 4 alpha), Pck1 (phosphoenolpyruvate carboxykinase 1), G6pc (glucose-6-phosphatase, catalytic), Cpt1a (carnitine palmitoyl transferase 1a), Acads (acyl-coenzyme A dehydrogenase, short chain), Acadm (acyl-coenzyme A dehydrogenase, medium chain), Acadl (acyl-coenzyme A dehydrogenase, long chain), Hmgcr (3-hydroxy-3-methylglutaryl-coenzyme A reductase), Pmvk (phosphomevalonate kinase), Sbref2 (sterol regulatory element binding factor 2), Ppargc1b (peroxisome proliferator-activated receptor gamma coactivator 1b), and Sod2 (superoxide dismutase 2). These biological processes may also be affected by enhanced or increased expression of NADH (nicotinamide adenine dinucleotide) dehydrogenase and subunits thereof. The biological processes are also affected by factors including reduced hepatic glucose production, reduced hepatic gluconeogenesis, and reduced hepatic lipid synthesis.

These risk factors may be modulated by increasing or decreasing (as appropriate) the expression of a gene, activity of an enzyme, etc., relative to the level of expression or activity seen in an individual or population not suffering from a metabolic, cardiovascular, inflammatory, or other disorder. Alternatively, the various genes, enzymes, and other risk factors may be modulated by increasing or decreasing (as appropriate) the expression of a gene, activity of an enzyme, etc., relative to the level of expression or activity seen in an individual or population suffering from a metabolic, cardiovascular, inflammatory, or other disorder to be treated or prevented.

The risk factors modulated in accordance with the methods of preventing or treating a metabolic, cardiovascular, inflammatory, or other disorder may be modulated to a degree that results in improvement in the symptoms of the disorder, elimination of the disorder, or reduction in risk for developing the disorder. In these aspects, it may be useful to establish a baseline level for the risk factor in a subject or patient population being treated by determining the amount of the risk factor present in a body fluid or organ of interest. Such a baseline could be determined by assessing the amount of one or more risk factors present in a body fluid or tissue sample taken from a subject or patient population, prior to any treatment with krill oil. According to some aspects, the krill oil or krill oil composition is then administered in an amount that is sufficient to result in an increase/decrease (as appropriate) in a level of a risk factor observed in a subject or patient population being treated by the methods of the invention. According to further aspects, the increase/decrease is at least 5% relative to the baseline level. Preferably the level of the risk factor is increased/decreased by at least 10%, at least 20%, at least 35%, at least 50%, at least 65%, at least 80%, at least 90%, or at least 95%, relative to the baseline level. In some embodiments, the level of the risk factor may be increased/decreased by 100%, 200%, 300%, 400%, 500%, 600%, 700%, 800%, 900%, 1000% or more as compared to the baseline level by the methods of the present invention.

Cardiovascular Disease

In certain embodiments, the present invention can be used in methods of decreasing cardiovascular disease risk factors of a subject. In some embodiments, the cardiovascular risk factors are selected from the group consisting of elevated blood pressure, elevated serum total cholesterol and low-density lipoprotein cholesterol (LDL-C), low serum high-density lipoprotein cholesterol (HDL-C), diabetes mellitus, abdominal obesity, elevated serum triglycerides, small LDL particles, elevated serum homocysteine, elevated serum lipoprotein(a), prothrombotic factors, fatty liver and inflammatory markers. In some embodiments, the subject is a human, and in other embodiments, the subject is clinically obese.

In some embodiments, the krill oil composition of the present invention find use in the treatment of fatty heart disease, alcoholic fatty liver disease, and non-alcoholic fatty liver disease. Thus, the krill oil compositions are useful for decreasing the lipid content of the heart and/or liver of a subject. In other embodiments, the present invention provides methods of providing a krill oil composition to a subject; and administering the krill oil composition to the subject under conditions such the liver and/or kidney functions are improved. In some embodiments, the subject is a human, and in other embodiments, the subject is clinically obese.

Obesity

Excess adipose tissue mass (overweight and obesity) is associated with low grade inflammation in adipose tissue and in the whole body reflecting the inflammatory mediators "spilling over" from fat tissue. Inflammation appears to be an important link between obesity and metabolic syndrome/type-II diabetes as well as cardiovascular disease. Thus, excess adipose tissue is an unhealthy condition.

Weight reduction will improve the inflammatory condition, but persistent weight reduction is difficult to achieve. Omega-3 fatty acid supplementation may alleviate the inflammatory condition in adipose tissue and thus ideally complement the principal strategies of weight reduction, i.e., low calorie diet and exercise. Although a diet and exercise regime may fail to result in a consistent decrease in weight over the long term, the effect of omega-3 fatty acids alleviating the inflammatory condition in the adipose tissue may persist, generating a condition that can be described as "healthy adipose tissue". Reduction in adipose tissue inflammation may be achieved by increasing circulating levels of adiponectin. Adiponectin is an adipose tissue derived anti-inflammatory hormone.

This aspect of the invention therefore relates to the discovery that krill oil is highly effective in alleviating negative health effects caused by obesity, such as reducing LDL cholesterol, reducing ectopic fat deposition and reducing susceptibility to inflammation. These negative health effects may lead to increased cardiovascular disease risk. Accordingly, another embodiment of the invention is to use krill oil in overweight and obese subjects for alleviating diet-induced adipose tissue dysfunction and diet induced changes in lipid metabolism.

In certain embodiments, the present invention provides methods comprising providing a krill oil composition to a subject; and administering the krill oil composition to the subject under conditions such that the appetite of the subject is reduced. In some embodiments, the subject is a human, and in other embodiments, the subject is clinically obese.

In certain embodiments, the present invention provides methods comprising providing a krill oil composition to a subject; and administering the krill oil composition to the subject under conditions such that fat accumulation in the subject is reduced. In some embodiments, the subject is a human, and in other embodiments, the subject is clinically obese.

In still other embodiments, the krill oil compositions of the present invention find use in increasing or inducing diuresis. In some embodiments, the krill oil compositions of the present invention find use in decreasing protein catabolism and increasing the muscle mass of a subject.

Type 2 Diabetes and Metabolic Disorder

Type 2 diabetes is a metabolic disorder characterized by impaired glycemic control (high blood glucose levels). In type 2 diabetes, tissue-wide insulin resistance contributes to the development of the disease. Strategies for reducing insulin resistance or improving tissue sensitivity to insulin are recognized as beneficial in preventing type 2 diabetes. In further embodiments, krill oil is effective in reducing risk factors of type 2 diabetes such as hyperinsulinemia and insulin resistance.

The methods of the present invention may be used to treat and/or prevent type II diabetes and metabolic syndrome in a subject, or reduce the incidence of type II diabetes and/or metabolic syndrome in a patient population comprising individuals at risk for developing diabetes and/metabolic syndrome. Another embodiment of the invention provides a krill oil composition effective for improving the blood lipid profile by increasing the HDL cholesterol levels, decreasing the LDL cholesterol and triglyceride levels. Hence the novel krill oil composition is effective for treating metabolic syndrome, which is defined as the coexistence of 3 or more components selected from the group: abdominal obesity, high serum triglyceride levels, low HDL levels, elevated blood pressure and high fasting plasma glucose levels. In another embodiment of the invention, krill oil compositions are provided that are effective and safe for the treatment of type II diabetes and metabolic syndrome in humans.

Endocannabinoid Modulation

In certain embodiments, the present invention provides methods comprising providing a krill oil composition to a subject under conditions such that cannabinoid receptor signaling is reduced. In some embodiments, inhibition of the endocannabinoid system of the subject comprises lowering the levels of arachidonylethanolamide (AEA) and/or 2-arachidonyl glycerol (2-AG). In some embodiments, the subject is a human, and in other embodiments, the subject is clinically obese.

The endocannabinoid system consists of cannabinoid (CB) receptors, endocannabinoids (EC) and enzymes involved in the synthesis and degradation of these molecules. Cannabionoid-1 (CB-1) receptors are located in the central nervous system such as the brain (basal ganglia, limbic system, cerebellum and hippocampus) and the reproductive system (both male and female), but also peripherally in liver, muscle, and different adipose tissues. Cannabionoid-2 (CB-2) receptors are located on immune cells and in the spleen.

A dysregulated endocannabinoid system results in excessive eating and fat accumulation and is therefore likely to play an important role in the pathogenesis of obesity. This chronic activation may not only be caused by obesity, but also by high fat diets, which can predispose the body to enhanced endocannabinoid biosynthesis.

The present invention discloses that krill oil can be used to effectively modulate the endocannabinoid system in Zucker fatty rats. It is shown that krill oil is more effective than fish oil and the control diet in reducing the level of endocannabinoids AEA and 2-AG in visceral adipose in this model. Visceral fat is the metabolically more active fat and accumulation of visceral fat has been associated with insulin resistance, glucose intolerance, dyslipidemia, hypertension and coronary heart disease. Accumulation of visceral fat is initiated where the capacity for storing subcutaneous fat is saturated. The Zucker rats are leptin receptor-deficient animals, and therefore they became obese due to the increased feed intake which gradually results in the development of metabolic syndrome (the rats develop hyperglycemia, ectopic fat deposition, and elevated LDL cholesterol levels). The data show that the reduction in 2-AG levels in subcutaneous adipose is the most pronounced while the level of AEA in liver and heart were also clearly reduced after intake of krill oil compared to all the other treatments. Subcutaneous fat is less metabolic active than visceral adipose tissue. Functional effects of a dysregulated endocannabinoid system were observed in Example 12, as the rats developed fatty heart, fatty liver, hyperglycemia and elevated LDL cholesterol levels.

Krill oil is an effective agent for modulating the endocannabinoid system, and thereby alleviating the negative health effects of obesity. The invention also relates to the discovery that krill oil is effective in reducing the level of the endocannabinoid precursors, i.e., the arachidonic acid content in phospholipids in the heart, subcutaneous adipose tissue, and visceral adipose tissue. The TAG fraction of the visceral and subcutaneous adipose tissue was influenced by omega-3 supplementation, showing an increased incorporation of EPA (30 fold), DHA (10 fold) and DPA (10 fold). However, the large increase in TAG is less metabolically important than the small increase in the phospholipids. The AEA and 2-AG concentration in visceral and adipose tissue mirrors the fatty acid profiles. Liver TAG omega-3 were significantly increased in fish oil and krill oil groups whereas no changes were found in arachidonic acid or other omega-6 fatty acids. Heart TAGs fatty acids showed increased levels of EPA, DPA and DHA and decrease in ARA in the phospholipid fraction.

The various methods of the present invention demonstrate that krill oil is effective in changing endocannabinoid receptor signaling by modulating the level of the cannabinoid receptor ligands. The levels of endocannabinoid precursors, i.e., arachidonic acid attached to phospholipids, are reduced as well. It might be that the high level of omega-3 phospholipids play a role in the effective modulation of the endocannabinoid system, however the mechanism of action by which krill oil works remains unknown at this stage.

The present invention also relates to modulation of the endocannabinoid system in tissues such as kidney, testis, different brain areas, intestines, pancreas, thyroids glands, etc. A preferred embodiment of this invention is the use of krill oil for modulation of a dysfunctional endocannabinoid system in all tissues in order to obtain improved health. Non-limiting examples of such health effects are treatment of obesity, reduction in feed intake, increased energy expenditure, reduction in cholesterol, improvement in male reproduction (spermatogenesis, sperm motility and acreosome reaction) and female reproduction (increased ovulation), increased sexual drive (libido), treatment of atherosclerosis, improvement in bone metabolism, improvement in lipid metabolism, treatment of ectopic fat deposition, treatment of liver disease such as fibrosis and cirrhosis, control of glucose homeostasis, improvement in insulin resistance, treatment of fatty heart and cardiomyopathy.

B. Krill Oil

According to some aspects, the various methods of the present invention may be carried out using krill oil, or compositions comprising krill oil. The krill oil is characterized by containing high levels of astaxanthin, phospholipids, included an enriched quantities of ether phospholipids, and omega-3 fatty acids.

Krill oil is obtained from Antarctic krill (*Euphausia Superba*) by extracting the lipids with supercritical and/or liquid solvents. Krill oil is different from fish oil at least in the respect that it contains astaxanthin, and the majority of the omega-3 fatty acids are attached to phospholipids.

In preferred embodiments, the krill oil compositions are made as described in co-pending application PCT/GB2008/001080, which is incorporated herein by reference. In other preferred embodiments, compositions for use in accordance with the invention may include, but are not limited to, Superba™ krill oil (Aker Biomarine, Norway). In other preferred embodiments, the compositions for use in accordance with the invention comprise krill oil that is obtained from krill meal by ethanol extraction and/or $CO_2$ extraction. However, any suitable methods for extracting oil from krill may be used in accordance with the present invention.

The krill oil-containing compositions that are preferably used in order to carry out the methods of the present invention are distinguished from previously-described krill oil products, such as those described in U.S. Pat. No. 6,800,299 or WO 03/011873 and Neptune brand krill oil (NKO®, Neptune Technologies & Bioressources, Laval, Quebec, Canada), by having substantially higher levels of non-ether phospholipids, ether phospholipids, and astaxanthin.

The krill compositions that may be used in accordance with the present invention are preferably derived from *Euphausia superba*. Regardless of the krill used, the compositions preferably comprise from about 40% to about 60% w/w phospholipids, preferably from about 45% to 55% w/w phospholipids and from about 300 mg/kg astaxanthin to about 2500 mg/kg astaxanthin, preferably from about 1000 to about 2200 mg/kg astaxanthin, more preferably from about 1500 to about 2200 mg/kg astaxanthin. In some preferred embodiments, the compositions comprise greater than about 1000, 1500, 1800, 1900, 2000, or 2100 mg/kg astaxanthin.

In some preferred embodiments, the krill compositions of the present invention comprise from about 1%, 2%, 3% or 4% to about 8%, 10%, 12% or 15% w/w ether phospholipids or greater than about 4%, 5%, 6%, 7%, 8%, 9% or 10% ether phospholipids. In some embodiments the ether phospholipids are preferably alkylacylphosphatidylcholine, lyso-alkylacylphosphatidylcholine, alkylacyiphosphatidyl-ethanolamine or combinations thereof. In some embodiments, the krill compositions comprise from about 1%, 2%, 3% or 4% to about 8%, 10%, 12% or 15% w/w ether phospholipids and from about 30%, 33%, 40%, 42%, 45%, 48%, 50%, 52%, 54%, 55% 56%, 58% to about 60% non-ether phospholipids so that the total amount of phospholipids (both ether and non-ether phospholipids) ranges from about 40% to about 60%. One of skill in the art will recognize that the range of 40% to 60% total phospholipids, as well as the other ranges of ether and non-ether phospholipids, can include other values not specifically listed within the range.

In further embodiments, the compositions comprise from about 20% to 45% w/w triglycerides; and from about 400 to about 2500 mg/kg astaxanthin. In some embodiments, the compositions comprise from about 20% to 35%, preferably from about 25% to 35%, omega-3 fatty acids as a percentage of total fatty acids in the composition, wherein from about 70% to 95%, or preferably from about 80% to 90% of the omega-3 fatty acids are attached to the phospholipids.

The krill oil extracted for use in the methods of the present invention contains few enzymatic breakdown products. Examples of the krill oil compositions of the present invention are provided in Tables 4-19. In some embodiments, the present invention provides a polar krill oil comprising at least 65% (w/w) of phospholipids, wherein the phospholipids are characterized in containing at least 35% omega-3 fatty acid residues. The present invention is not limited to the presence of any particular omega-3 fatty acid residues in the krill oil composition. In some preferred embodiments, the krill oil comprises EPA and DHA residues. In some embodiments, the krill oil compositions comprise less than about 5%, 4%, 3% or preferably 2% free fatty acids on a weight/weight (w/w) basis. In some embodiments, the krill oil compositions comprise less than about 25%, 20%, 15%, 10% or 5% triglycerides (w/w). In some embodiments, the krill oil compositions comprise greater than about 30%, 40%, 45%, 50%, 55%, 60%, or 65% phosphatidyl choline (w/w). In some embodiments, the krill oil compositions comprise greater than about 100, 200, 300, 400, or 500 mg/kg astaxanthin esters and up to about 700 mg/kg astaxanthin esters. In some embodiments, the present invention provides krill oil compositions comprising at least 500, 1000, 1500, 2000, 2100, or 2200 mg/kg astaxanthin esters and at least 36% (w/w) omega-3 fatty acids. In some embodiments, the krill oil compositions of the present invention comprise less than about 1.0 g/100 g, 0.5 g/100 g, 0.2 g/100 g or 0.1 g/100 g total cholesterol. In some embodiments, the krill oil compositions of the present invention comprise less than about 0.45.

In some embodiments, the present invention is carried out using a neutral krill oil extract comprising greater than about 70%, 75% 80%, 85% or 90% triglycerides. In some embodiments, the krill oil compositions comprise from about 50 to about 2500 mg/kg astaxanthin esters. In some embodiments, the krill oil compositions comprise from about 50, 100, 200, or 500 to about 750, 1000, 1500 or 2500 mg/kg astaxanthin esters. In some embodiments, the compositions comprise from about 1% to about 30% omega-3 fatty acid residues, and preferably from about 5%-15% omega-3 fatty acid residues. In some embodiments, the krill oil compositions comprise less than about 20%, 15%, 10% or 5% phospholipids.

In some embodiments, the present invention is carried out using krill oil containing less than about 70, 60, 50, 40, 30, 20, 10, 5 or 1 micrograms/kilogram (w/w) astaxanthin esters. In some embodiments, the krill oil is clear or only has a pale red color. In some embodiments, the low-astaxanthin krill oil is obtained by first extracting a krill material, such as krill oil, by supercritical fluid extraction with neat carbon dioxide. It is contemplated that this step removes astaxanthin from the krill material. In some embodiments, the krill material is then subjected to supercritical fluid extraction with carbon dioxide and a polar entrainer such as ethanol, preferably about 20% ethanol. The oil extracted during this step is characterized in containing low amounts of astaxanthin. In other embodiments, krill oil comprising astaxanthin is extracted by countercurrent supercritical fluid extraction with neat carbon dioxide to provide a low-astaxanthin krill oil.

In some embodiments, the present invention is carried out using krill oil that is substantially odorless. By substantially odorless it is meant that the krill oil lacks an appreciable odor as determined by a test panel. In some embodiments, the substantially odorless krill oil comprises less than about 10, 5 or 1 milligrams/kilogram trimethylamine. In some preferred embodiments, the odorless krill oil is produced by first subjecting krill material to supercritical fluid extraction with neat carbon dioxide to remove odor causing compounds such as trimethylamine, followed by extraction with carbon dioxide with a polar entrainer such as ethanol.

C. Krill Oil-Based Compositions

In some embodiments, the present invention provides encapsulated *Euphausia superba* krill oil compositions. In some embodiments, the present invention provides a method of making a *Euphausia superba* krill oil composition comprising contacting *Euphausia superba* with a polar solvent to provide an polar extract comprising phospholipids, contacting *Euphausia superba* with a neutral solvent to provide a neutral extract comprising triglycerides and astaxanthin, and combining said polar extract and said neutral extract to provide the *Euphausia superba* krill oils described above.

In some embodiments, fractions from polar and non-polar extractions are combined to provide a final product comprising the desired ether phospholipids, non-ether phospholipids, omega-3 moieties and astaxanthin. In other embodiments, the present invention provides methods of making a *Euphausia superba* (or other krill species) krill oil comprising contacting a *Euphausia superba* preparation such as *Euphausia superba* krill meal under supercritical conditions with $CO_2$ containing a low amount of a polar solvent such as ethanol to extract neutral lipids and astaxanthin; contacting meal remaining from the first extraction step under supercritical conditions with $CO_2$ containing a high amount of a polar solvent such as ethanol to extract a polar lipid fraction containing ether and non-ether phospholipids; and then blending the neutral and polar lipid extracts to provide the compositions described above.

In some embodiments, the compositions of this invention are contained in acceptable excipients and/or carriers for oral consumption. The actual form of the carrier, and thus, the composition itself, is not critical. The carrier may be a liquid, gel, gelcap, capsule, powder, solid tablet (coated or non-coated), tea, or the like. The composition is preferably in the form of a tablet or capsule and most preferably in the form of a soft gel capsule. Suitable excipient and/or carriers include maltodextrin, calcium carbonate, dicalcium phosphate, tricalcium phosphate, microcrystalline cellulose, dextrose, rice flour, magnesium stearate, stearic acid, croscarmellose sodium, sodium starch glycolate, crospovidone, sucrose, vegetable gums, lactose, methylcellulose, povidone, carboxymethylcellulose, corn starch, and the like (including mixtures thereof). Preferred carriers include calcium carbonate, magnesium stearate, maltodextrin, and mixtures thereof. The various ingredients and the excipient and/or carrier are mixed and formed into the desired form using conventional techniques. The tablet or capsule of the present invention may be coated with an enteric coating that dissolves at a pH of about 6.0 to 7.0. A suitable enteric coating that dissolves in the small intestine but not in the stomach is cellulose acetate phthalate. Further details on techniques for formulation for and administration may be found in the latest edition of *Remington's Pharmaceutical Sciences* (Maack Publishing Co., Easton, Pa.).

The composition may comprise one or more inert ingredients, especially if it is desirable to limit the number of calories added to the diet by the composition. For example, the dietary supplement of the present invention may also contain optional ingredients including, for example, herbs, vitamins, minerals, enhancers, colorants, sweeteners, flavorants, inert ingredients, and the like. For example, the composition of the present invention may contain one or more of the following: ascorbates (ascorbic acid, mineral ascorbate salts, rose hips, acerola, and the like), dehydroepiandosterone (DHEA), Fo-Ti or Ho Shu Wu (herb common to traditional Asian treatments), Cat's Claw (ancient herbal ingredient), green tea (polyphenols), inositol, kelp, dulse, bioflavinoids, maltodextrin, nettles, niacin, niacinamide, rosemary, selenium, silica (silicon dioxide, silica gel, horsetail, shavegrass, and the like), spirulina, zinc, and the like. Such optional ingredients may be either naturally occurring or concentrated forms.

In some embodiments, the composition may further comprise vitamins and minerals including, but not limited to, calcium phosphate or acetate, tribasic; potassium phosphate, dibasic; magnesium sulfate or oxide; salt (sodium chloride); potassium chloride or acetate; ascorbic acid; ferric orthophosphate; niacinamide; zinc sulfate or oxide; calcium pantothenate; copper gluconate; riboflavin; beta-carotene; pyridoxine; folic acid; thiamine; biotin; chromium chloride or picolonate; potassium iodide; sodium selenate; sodium molybdate; phylloquinone; retinoic acid; cyanocobalamin; sodium selenite; copper sulfate; vitamin A; vitamin C; inositol; potassium iodide; vitamin E, vitamin K; niacin; and pantothenic acid. Suitable dosages for vitamins and minerals may be obtained, for example, by consulting the U.S. RDA guidelines. In still other embodiments, the particles comprise an amino acid supplement formula in which at least one amino acid is included (e.g., 1-carnitine or tryptophan).

In further embodiments, the composition comprises at least one food flavoring such as acetaldehyde (ethanal), acetoin (acetyl methylcarbinol), anethole (parapropenyl anisole), benzaldehyde (benzoic aldehyde), N butyric acid (butanoic acid), d or l carvone (carvol), cinnamaldehyde (cinnamic aldehyde), citral (3,7-dimethyl-2,6-octadienal, geranial, neral), decanal (N-decylaldehyde, capraldehyde, capric aldehyde, caprinaldehyde, aldehyde C 10), ethyl acetate, ethyl butyrate, 3-methyl-3-phenyl glycidic acid ethyl ester (ethyl methyl phenyl glycidate, strawberry aldehyde, C16 aldehyde), ethyl vanillin, geraniol (3,7-dimethylocta-2,6-dien-1-ol), geranyl acetate (geraniol acetate), limonene (d, l, and dl), linalool (3,7-dimethylocta-1,6-dien-3-ol), linalyl acetate (bergamol), methyl anthranilate (methyl-2-aminobenzoate), piperonal (3,4-methylenedioxy benzaldehyde, heliotropin), vanillin, alfalfa (*Medicago sativa* L.), allspice (*Pimenta officinalis*), ambrette seed (*Hibiscus abelmoschus*), angelic (*Angelica archangelica*), Angostura (*Galipea officinalis*), anise (*Pimpinella anisum*), star anise (*Illicium verum*), balm (*Melissa officinalis*), basil (*Ocimum basilicum*), bay (*Laurus nobilis*), calendula (*Calendula officinalis*), chamomile (*Anthemis nobilis*), capsicum (*Capsicum frutescens*), caraway (*Carum carvi*), cardamom (*Elettaria cardamomum*), cassia (*Cinnamomum cassia*), cayenne pepper (*Capsicum frutescens*), Celery seed (*Apium graveolens*), chervil (*Anthriscus cerefolium*), chives (*Allium schoenoprasum*), coriander (*Coriandrum sativum*), cumin (*Cuminum cyminum*), elder flowers (*Sambucus canadensis*), fennel (*Foeniculum vulgare*), fenugreek (*Trigonella foenum graecum*), ginger (*Zingiber officinale*), horehound (*Marrubium vulgare*), horseradish (*Armoracia lapathifolia*), hyssop (*Hyssopus officinalis*), lavender (*Lavandula officinalis*), mace (*Myristica fragrans*), marjoram (*Majorana hortensis*), mustard (*Brassica nigra, Brassica juncea, Brassica hirta*), nutmeg (*Myristica fragrans*), paprika (*Capsicum annuum*), black pepper (*Piper nigrum*), peppermint (*Mentha piperita*), poppy seed (*Papayer somniferum*), rosemary (*Rosmarinus officinalis*), saffron (*Crocus sativus*), sage (*Salvia officinalis*), savory (*Satureia hortensis, Satureia montana*), sesame (*Sesamum indicum*), spearmint (*Mentha spicata*), tarragon (*Artemisia dracunculus*), thyme (*Thymus vulgaris, Thymus serpyllum*), turmeric (*Curcuma longa*), vanilla (*Vanilla planifolia*), zedoary (*Curcuma zedoaria*), sucrose, glucose, saccharin, sorbitol, mannitol, aspartame. Other suitable flavoring are disclosed in such references as *Remington's Pharmaceutical Sciences*, 18th Edition, Mack Publishing, p. 1288-1300 (1990), and Furia and Pellanca, *Fenaroli's Handbook of Flavor Ingredients*, The Chemical Rubber Company, Cleveland, Ohio, (1971), known to those skilled in the art.

In other embodiments, the compositions comprise at least one synthetic or natural food coloring (e.g., annatto extract, astaxanthin, beet powder, ultramarine blue, canthaxanthin, caramel, carotenal, beta carotene, carmine, toasted cottonseed flour, ferrous gluconate, ferrous lactate, grape color extract, grape skin extract, iron oxide, fruit juice, vegetable juice, dried algae meal, tagetes meal, carrot oil, corn endosperm oil, paprika, paprika oleoresin, riboflavin, saffron, tumeric, and oleoresin).

In still further embodiments, the compositions comprise at least one phytonutrient (e.g., soy isoflavonoids, oligomeric proanthcyanidins, indol-3-carbinol, sulforaphone, fibrous ligands, plant phytosterols, ferulic acid, anthocyanocides, triterpenes, omega 3/6 fatty acids, conjugated fatty acids such as conjugated linoleic acid and conjugated linolenic acid, polyacetylene, quinones, terpenes, cathechins, gallates, and quercitin). Sources of plant phytonutrients include, but are not limited to, soy lecithin, soy isoflavones, brown rice germ, royal jelly, bee propolis, acerola berry juice powder, Japanese green tea, grape seed extract, grape skin extract, carrot juice, bilberry, flaxseed meal, bee pollen, ginkgo biloba, primrose (evening primrose oil), red clover, burdock root, dandelion, parsley, rose hips, milk thistle, ginger, Siberian ginseng, rosemary, curcumin, garlic, lycopene, grapefruit seed extract, spinach, and broccoli.

EXAMPLES

The present invention is further described in the following non-limiting Examples.

Example 1

Antarctic krill (*Euphausia superba*) was captured and brought on board alive, before it was processed into krill meal, an oil (asta oil), and stickwater. During the krill meal processing a neutral oil (asta oil) is recovered.

Example 2

The krill meal obtained in Example 1 was then ethanol extracted according to the method disclosed in JP 02-215351, the contents of which are incorporated herein by reference. The results showed that around 22% fat from the meal could be extracted. Table 1 shows the fatty acid composition of the krill meal and the krill oil extracted from the meal using ethanol. Table 2 shows the composition and properties of the krill meal and products before and after extraction, whereas Table 3 shows the lipid composition.

TABLE 1

Fatty acid distribution in krill meal (g/100 g lipid) and the ethanol extracted krill oil.

| Fatty Acid File | Krill meal | EtOH KO |
|---|---|---|
| C4:0 | 0.00 | |
| C6:0 | 0.00 | |
| C8:0 | 0.00 | |
| C10:0 | 0.00 | |
| C12:0 | 0.00 | |
| C14:0 | 7.8 | 6.4 |
| C14:1 | 0.00 | |
| C15:0 | 0.00 | |
| C16:0 | 15.8 | 14.7 |
| C16:1 | 5.1 | 4.2 |
| C18:0 | 0.9 | 0.7 |
| C18:1 | 13.4 | 11.8 |
| C18:2N6 | 1.1 | 1.2 |
| C18:3N6 | 0.1 | 0.1 |
| C18:3N3 | 0.4 | 0.4 |
| C18:4N3 | 1.1 | 0.1 |
| C20:0 | 0.1 | 0.1 |
| C20:1 | 0.8 | 0.6 |
| C20:2N6 | <0.1 | <0.1 |
| C20:3N6 | 0.1 | <0.1 |
| C20:4N6 | 0.2 | 0.2 |
| C20:3N3 | <0.1 | <0.1 |
| C20:4N3 | 0.2 | 0.2 |
| C20:5N3 (EPA) | 10.5 | 10.4 |
| C22:0 | <0.1 | <0.1 |
| C22:1 | 0.5 | 0.4 |
| C22:2N6 | <0.1 | <0.1 |
| C22:4N6 | <0.1 | |
| C22:5N6 | 0.00 | |
| C22:5N3 | 0.2 | |
| C22:6N3 (DHA) | 5.4 | 4.8 |
| C24:1 | 0.03 | |
| Saturated | 24.6 | 21.9 |
| Monounsaturated | 19.9 | 17.0 |
| Polyunsaturated | 21.0 | 19.4 |
| Total | 65.5 | 58.2 |
| Omega-3 | 18.2 | 17.0 |
| Omega-6 | 1.3 | |

TABLE 2

Composition and properties of the krill meal and products after extraction

| | Krill meal | Delipidated krill meal | EtOH extracted krill oil |
|---|---|---|---|
| Crude protein | 586 g/kg | 735 g/kg | |
| Fat (Folch) | 250 g/kg | 30 g/kg | |
| Moisture/ethanol | 71 g/kg | 134 g/kg | 85 g/kg |
| Astaxanthin esters | 144 mg/kg | 10 mg/kg | 117 mg/kg |
| Diesters | 110 mg/kg | 8.5 mg/kg | 117 mg/kg |
| Monoesters | 33 mg/kg | 1.8 mg/kg | 37 mg/kg |
| Biological digestable protein | 854 g/kg protein | 870 g/kg protein | |
| Flow number | 4.8 | 1.9 | |
| NH3 | 9 mg N/100 g | 0 | 3 mg N/100 g |
| TMA | 2 mg N/100 g | 0 | 70 mg N/100 g |
| TMAO | 125 mg N/100 g | 0 | 456 mg N/100 g |

TABLE 3

Lipid class distribution

| | Krill meal | Delipidated krill meal | EtOH extracted KO |
|---|---|---|---|
| Cholesterol ester | 3.5 | | |
| TG | 32.7 | 37.4 | 31.1 |
| FFA | 7.8 | 14.1 | 16.0 |
| Cholesterol | 9.1 | 8.0 | 12.6 |
| DG | 1.1 | | 3.3 |
| MG | 3.7 | | |
| Sphingolipid | | | 2.8 |
| PE | 6.5 | 2.5 | 2.7 |
| Cardiolipin | | 4.2 | |
| PI | 1.1 | 11.0 | |

TABLE 3-continued

Lipid class distribution

| | Krill meal | Delipidated krill meal | EtOH extracted KO |
|---|---|---|---|
| PS | 1.4 | | |
| PC | 28.6 | 20.2 | 25.3 |
| LPC | 2.9 | 2.6 | 6.2 |
| Total polar lipids | 40.6 | 40.5 | 36.9 |
| Total neutral lipids | 54.2 | 59.5 | 63.1 |

Example 3

The krill meal obtained in Example 1 was then subjected to a supercritical fluid extraction method in two stages. During stage 1, 12.1% fat (neutral krill oil) was removed using neat $CO_2$ only at 300 bars, 60° C. and for 30 minutes. In stage 2, the pressure was increased to 400 bar and 20% ethanol was added (v/v) for 90 minutes. This resulted in further extraction of 9% polar fat which hereafter is called polar krill oil. The total fatty acid composition of the polar krill oil, the neutral krill oil and a commercial product obtained from Neptune Biotech (Laval, Quebec, Canada) are listed in Table 4. In addition the fatty acid composition for the phospholipids (Table 5), the neutral lipids (Table 6), the free fatty acids, diglycerides (Table 7), triglycerides, lysophosphatidylcholine (LPC) (Table 8), phosphatidylcholine (PC), phosphatidylethanolamine (PE) (Table 9), phosphatidylinositol (PI) and phosphatidylserine (PS) (Table 10) are shown. Table 11 shows the level of astaxanthin and cholesterol for the different fractions.

TABLE 4

Total fatty acids compositions of the krill oil products (% (w/w))

| | Total Fatty Acids | | |
|---|---|---|---|
| Fatty Acid File | Neutral KO | Polar KO | NKO |
| C4:0 | 0.00 | 0.00 | 0.00 |
| C6:0 | 0.00 | 0.00 | 0.00 |
| C8:0 | 0.00 | 0.00 | 0.00 |
| C10:0 | 0.00 | 0.00 | 0.00 |
| C12:0 | 0.47 | 0.04 | 0.24 |
| C14:0 | 22.08 | 3.28 | 12.48 |
| C14:1 | 0.33 | 0.01 | 0.17 |
| C15:0 | 0.58 | 0.36 | 0.52 |
| C16:0 | 27.03 | 29.25 | 23.25 |
| C16:1 | 0.07 | 0.01 | 8.44 |
| C18:0 | 1.72 | 1.03 | 1.42 |
| C18:1 | 30.29 | 13.57 | 18.92 |
| C18:2N6 | 2.10 | 1.96 | 1.71 |
| C18:3N6 | 0.30 | 0.21 | 0.00 |
| C18:3N3 | 0.69 | 1.02 | 1.32 |
| C18:4N3 | 0.05 | 1.81 | 3.50 |
| C20:0 | 0.06 | 0.00 | 0.05 |
| C20:1 | 1.87 | 0.80 | 1.16 |
| C20:2N6 | 0.05 | 0.05 | 0.05 |
| C20:3N6 | 0.22 | 0.73 | 0.04 |
| C20:4N6 | 0.00 | 0.00 | 0.49 |
| C20:3N3 | 0.09 | 0.09 | 0.06 |
| C20:4N3 | 0.24 | 0.51 | 0.33 |
| C20:5N3 (EPA) | 7.33 | 29.88 | 16.27 |
| C22:0 | 0.01 | 0.06 | 0.05 |
| C22:1 | 0.64 | 1.78 | 0.82 |
| C22:2N6 | 0.00 | 0.00 | 0.00 |
| C22:4N6 | 0.00 | 0.00 | 0.07 |
| C22:5N6 | 0.00 | 0.03 | 0.00 |
| C22:5N3 | 0.21 | 0.67 | 0.36 |
| C22:6N3 (DHA) | 3.51 | 12.61 | 8.17 |
| C24:0 | 0.05 | 0.00 | 0.01 |
| C24:1 | 0.03 | 0.25 | 0.11 |
| Total | 100.00 | 100.00 | 100.00 |
| Saturated | 52.00 | 34.01 | 38.01 |
| Monounsaturated | 33.22 | 16.43 | 29.61 |
| Polyunsaturated | 14.77 | 49.56 | 32.37 |
| Total | 100.00 | 100.00 | 100.00 |
| Omega-3 | 12.11 | 46.58 | 30.02 |
| Omega-6 | 2.67 | 2.98 | 2.35 |

TABLE 5

Fatty acid composition of the phospholipid fraction (% (w/w)).

| | Total Phospholipid | | |
|---|---|---|---|
| Fatty Acid File | Neutral KO | Polar KO | Neptune KO |
| C4:0 | 0.00 | 0.00 | 0.00 |
| C6:0 | 0.00 | 0.00 | 0.00 |
| C8:0 | 0.00 | 0.00 | 0.00 |
| C10:0 | 0.00 | 0.00 | 0.00 |
| C12:0 | 0.00 | 0.00 | 0.00 |
| C14:0 | 0.01 | 0.00 | 0.00 |
| C14:1 | 0.42 | 0.01 | 0.01 |
| C15:0 | 2.52 | 0.00 | 0.00 |
| C16:0 | 4.73 | 35.78 | 32.81 |
| C16:1 | 0.19 | 0.17 | 0.19 |
| C18:0 | 6.31 | 1.18 | 1.55 |
| C18:1 | 38.40 | 15.58 | 13.54 |
| C18:2N6 | 4.18 | 2.16 | 1.90 |
| C18:3N6 | 0.18 | 0.22 | 0.19 |
| C18:3N3 | 1.02 | 1.05 | 1.48 |
| C18:4N3 | 3.08 | 1.62 | 2.15 |
| C20:0 | 0.27 | 0.00 | 0.07 |
| C20:1 | 2.55 | 1.02 | 0.78 |
| C20:2N6 | 0.19 | 0.06 | 0.06 |
| C20:3N6 | 0.00 | 0.14 | 0.10 |
| C20:4N6 | 0.57 | 0.62 | 0.64 |
| C20:3N3 | 0.43 | 0.08 | 0.09 |
| C20:4N3 | 0.17 | 0.45 | 0.42 |
| C20:5N3 (EPA) | 20.58 | 25.53 | 26.47 |
| C22:0 | 0.14 | 0.06 | 0.00 |
| C22:1 | 0.00 | 2.09 | 1.94 |
| C22:2N6 | 0.25 | 0.71 | 0.85 |
| C22:4N6 | 0.44 | 0.00 | 0.03 |
| C22:5N6 | 0.11 | 0.00 | 0.00 |
| C22:5N3 | 0.00 | 0.60 | 0.63 |
| C22:6N3 (DHA) | 10.93 | 10.30 | 13.34 |
| C24:0 | 1.77 | 0.30 | 0.37 |
| C24:1 | 0.59 | 0.28 | 0.38 |
| Total | 100.00 | 100.00 | 100.00 |
| Saturated | 15.74 | 37.32 | 34.81 |
| Monounsaturated | 42.14 | 19.15 | 16.84 |
| Polyunsaturated | 42.12 | 43.53 | 48.34 |
| Total | 100.00 | 100.00 | 100.00 |
| Omega-3 | 36.22 | 39.62 | 44.56 |
| Omega-6 | 5.91 | 3.90 | 3.78 |

TABLE 6

Fatty acid composition of the total neutral lipid fraction (% (w/w)).

| | Total neutral lipid | | |
|---|---|---|---|
| Fatty Acid File | Neutral KO | Polar KO | Neptune KO |
| C4:0 | 0.00 | 0.00 | 0.00 |
| C6:0 | 0.00 | 0.00 | 0.00 |
| C8:0 | 0.00 | 0.00 | 0.00 |
| C10:0 | 0.00 | 0.00 | 0.00 |
| C12:0 | 0.00 | 0.00 | 0.00 |
| C14:0 | 20.35 | 11.31 | 18.44 |
| C14:1 | 0.30 | 0.29 | 0.25 |
| C15:0 | 0.53 | 1.53 | 0.62 |
| C16:0 | 23.79 | 0.49 | 24.11 |
| C16:1 | 12.42 | 5.22 | 11.86 |
| C18:0 | 1.54 | 3.27 | 1.67 |
| C18:1 | 26.81 | 33.09 | 23.82 |
| C18:2N6 | 1.68 | 2.37 | 1.79 |
| C18:3N6 | 0.20 | 0.23 | 0.25 |
| C18:3N3 | 0.59 | 0.62 | 0.03 |
| C18:4N3 | 0.03 | 1.27 | 0.05 |
| C20:0 | 0.07 | 0.00 | 0.06 |
| C20:1 | 1.63 | 1.41 | 1.39 |
| C20:2N6 | 0.04 | 0.00 | 0.05 |
| C20:3N6 | 0.18 | 0.94 | 0.01 |
| C20:4N6 | 0.00 | 0.00 | 0.00 |
| C20:3N3 | 0.09 | 0.00 | 0.01 |
| C20:4N3 | 0.18 | 0.41 | 0.23 |
| C20:5N3 (EPA) | 5.88 | 19.26 | 9.68 |
| C22:0 | 0.02 | 0.00 | 0.03 |
| C22:1 | 0.56 | 0.60 | 0.53 |
| C22:2N6 | 0.00 | 0.00 | 0.00 |
| C22:4N6 | 0.00 | 0.00 | 0.04 |
| C22:5N6 | 0.01 | 0.00 | 0.00 |
| C22:5N3 | 0.17 | 0.27 | 0.22 |
| C22:6N3 (DHA) | 2.74 | 17.22 | 4.64 |
| C24:0 | 0.15 | 0.00 | 0.17 |
| C24:1 | 0.03 | 0.21 | 0.06 |
| Total | 100.00 | 100.00 | 100.00 |
| Saturated | 46.45 | 16.60 | 45.10 |
| Monounsaturated | 41.75 | 40.82 | 37.91 |
| Polyunsaturated | 11.80 | 42.59 | 16.99 |
| Total | 100.00 | 100.00 | 100.00 |
| Omega-3 | 9.68 | 39.05 | 14.86 |
| Omega-6 | 2.11 | 3.54 | 2.14 |

TABLE 7

Fatty acid composition of the diglyceride and free fatty acids (% (w/w)).

| | Diglycerides | | | Free fatty acids | | |
|---|---|---|---|---|---|---|
| Fatty Acid File | Neutral KO | Polar KO | Neptune KO | Neutral KO | Polar KO | Neptune KO |
| C4:0 | 0.00 | 0.00 | 0.00 | 0.00 | 0.00 | 0.00 |
| C6:0 | 0.00 | 0.00 | 0.00 | 0.00 | 0.00 | 0.00 |
| C8:0 | 0.00 | 0.00 | 0.00 | 0.00 | 0.00 | 0.00 |
| C10:0 | 0.00 | 0.00 | 0.00 | 0.00 | 0.00 | 0.00 |
| C12:0 | 0.00 | 0.00 | 0.00 | 0.00 | 0.00 | 0.00 |
| C14:0 | 13.85 | 14.35 | 12.22 | 5.86 | 7.19 | 5.45 |
| C14:1 | 0.18 | 0.00 | 0.17 | 0.05 | 0.00 | 0.08 |
| C15:0 | 0.49 | 1.08 | 0.66 | 0.46 | 1.60 | 0.45 |
| C16:0 | 23.68 | 35.24 | 25.81 | 28.30 | 29.37 | 21.12 |
| C16:1 | 9.49 | 6.80 | 0.09 | 3.27 | 3.08 | 4.91 |
| C18:0 | 1.56 | 3.63 | 1.89 | 1.13 | 2.43 | 0.99 |
| C18:1 | 23.67 | 19.85 | 23.82 | 14.50 | 14.77 | 17.41 |
| C18:2N6 | 1.79 | 0.21 | 1.90 | 1.69 | 0.97 | 1.86 |
| C18:3N6 | 0.17 | 0.00 | 0.01 | 0.14 | 0.00 | 0.22 |
| C18:3N3 | 0.69 | 0.00 | 1.19 | 0.85 | 0.00 | 1.34 |
| C18:4N3 | 1.92 | 0.00 | 2.75 | 1.30 | 0.00 | 2.72 |
| C20:0 | 0.00 | 0.00 | 0.00 | 0.00 | 0.00 | 0.00 |
| C20:1 | 1.09 | 0.00 | 1.01 | 0.48 | 0.00 | 0.57 |
| C20:2N6 | 0.00 | 0.00 | 0.00 | 0.00 | 0.00 | 0.00 |
| C20:3N6 | 0.13 | 0.00 | 0.00 | 0.08 | 0.00 | 0.05 |
| C20:4N6 | 0.45 | 0.00 | 0.64 | 0.78 | 0.00 | 1.43 |
| C20:3N3 | 0.00 | 0.00 | 0.00 | 0.00 | 0.00 | 0.00 |
| C20:4N3 | 0.35 | 0.00 | 0.43 | 0.39 | 0.00 | 0.43 |
| C20:5N3 (EPA) | 14.03 | 9.80 | 18.00 | 24.33 | 23.57 | 25.36 |
| C22:0 | 0.18 | 0.00 | 0.10 | 0.00 | 0.00 | 0.05 |
| C22:1 | 0.41 | 0.00 | 0.57 | 0.80 | 0.69 | 0.37 |
| C22:2N6 | 0.28 | 0.00 | 0.50 | 0.46 | 0.00 | 0.54 |
| C22:4N6 | 0.00 | 0.00 | 0.00 | 0.00 | 0.00 | 0.00 |
| C22:5N6 | 0.00 | 0.00 | 0.00 | 0.00 | 0.00 | 0.00 |
| C22:5N3 | 0.20 | 0.00 | 0.27 | 0.34 | 0.00 | 0.32 |
| C22:6N3 (DHA) | 4.74 | 9.04 | 7.53 | 14.31 | 16.33 | 13.95 |
| C24:0 | 0.64 | 0.00 | 0.42 | 0.49 | 0.00 | 0.39 |
| C24:1 | 0.00 | 0.00 | 0.00 | 0.00 | 0.00 | 0.00 |
| Total | 100.00 | 100.00 | 100.00 | 100.00 | 100.00 | 100.00 |
| Saturated | 40.40 | 54.30 | 41.10 | 36.24 | 40.59 | 28.45 |
| Monounsaturated | 34.84 | 26.64 | 25.66 | 19.09 | 18.54 | 23.34 |
| Polyunsaturated | 24.77 | 19.06 | 33.24 | 44.67 | 40.87 | 48.22 |
| Total | 100.00 | 100.00 | 100.00 | 100.00 | 100.00 | 100.00 |
| Omega-3 | 21.95 | 18.85 | 30.18 | 41.51 | 39.90 | 44.13 |
| Omega-6 | 2.82 | 0.21 | 3.05 | 3.15 | 0.97 | 4.09 |

TABLE 8

Fatty acid composition of the triglyceride and lyso-phophatidylcholine fractions (% (w/w)).

| | Triglycerides | | | Lyso PC | | |
|---|---|---|---|---|---|---|
| Fatty Acid File | Neutral KO | Polar KO | Neptune KO | Neutral KO | Polar KO | Neptune KO |
| C4:0 | 0.00 | 0.00 | 0.00 | 0.00 | 0.00 | 0.00 |
| C6:0 | 0.00 | 0.00 | 0.00 | 0.00 | 0.00 | 0.00 |
| C8:0 | 0.00 | 0.00 | 0.00 | 0.00 | 0.00 | 0.00 |
| C10:0 | 0.00 | 0.00 | 0.00 | 0.00 | 0.00 | 0.00 |
| C12:0 | 0.00 | 0.00 | 0.00 | 0.00 | 0.00 | 0.00 |
| C14:0 | 23.06 | 26.65 | 25.13 | 19.38 | 4.27 | 2.87 |
| C14:1 | 0.36 | 0.93 | 0.36 | 0.00 | 0.08 | 0.00 |
| C15:0 | 0.56 | 2.64 | 0.78 | 0.00 | 0.52 | 0.45 |
| C16:0 | 23.17 | 4.93 | 27.80 | 41.00 | 44.14 | 30.56 |
| C16:1 | 13.68 | 11.58 | 0.04 | 0.00 | 1.84 | 2.24 |
| C18:0 | 1.52 | 3.12 | 1.99 | 0.76 | 1.59 | 1.32 |
| C18:1 | 27.83 | 34.39 | 27.92 | 6.65 | 14.24 | 11.29 |
| C18:2N6 | 1.64 | 2.05 | 1.92 | 0.00 | 1.75 | 2.07 |
| C18:3N6 | 0.20 | 0.00 | 0.30 | 0.00 | 0.00 | 0.06 |
| C18:3N3 | 0.51 | 0.00 | 0.00 | 7.95 | 0.67 | 1.75 |
| C18:4N3 | 1.99 | 0.00 | 4.83 | 0.00 | 1.11 | 2.46 |
| C20:0 | 0.06 | 0.00 | 0.08 | 0.00 | 0.00 | 0.00 |
| C20:1 | 1.67 | 0.00 | 1.76 | 0.00 | 0.52 | 0.00 |
| C20:2N6 | 0.04 | 0.00 | 0.05 | 0.00 | 0.00 | 0.00 |
| C20:3N6 | 0.05 | 0.00 | 0.01 | 0.00 | 0.00 | 0.54 |
| C20:4N6 | 0.00 | 0.00 | 0.00 | 0.00 | 0.40 | 0.00 |
| C20:3N3 | 0.05 | 0.00 | 0.07 | 0.00 | 0.00 | 0.00 |
| C20:4N3 | 0.11 | 0.00 | 0.17 | 0.00 | 0.31 | 0.55 |
| C20:5N3 (EPA) | 2.10 | 7.97 | 4.44 | 0.00 | 18.59 | 28.48 |
| C22:0 | 0.02 | 0.00 | 0.04 | 0.00 | 0.00 | 0.00 |
| C22:1 | 0.37 | 0.00 | 0.42 | 0.00 | 1.46 | 0.91 |
| C22:2N6 | 0.00 | 0.00 | 0.00 | 0.00 | 0.00 | 0.00 |
| C22:4N6 | 0.01 | 0.00 | 0.01 | 0.00 | 0.00 | 0.00 |

TABLE 8-continued

Fatty acid composition of the triglyceride and lyso-phosphatidylcholine fractions (% (w/w)).

| Fatty Acid File | Triglycerides | | | Lyso PC | | |
|---|---|---|---|---|---|---|
| | Neutral KO | Polar KO | Neptune KO | Neutral KO | Polar KO | Neptune KO |
| C22:5N6 | 0.00 | 0.00 | 0.01 | 0.00 | 0.00 | 0.00 |
| C22:5N3 | 0.10 | 0.00 | 0.16 | 0.00 | 0.41 | 0.62 |
| C22:6N3 (DHA) | 0.67 | 3.97 | 1.42 | 24.26 | 7.79 | 13.82 |
| C24:0 | 0.26 | 1.78 | 0.26 | 0.00 | 0.32 | 0.00 |
| C24:1 | 0.00 | 0.00 | 0.03 | 0.00 | 0.00 | 0.00 |
| Total | 100.00 | 100.00 | 100.00 | 100.00 | 100.00 | 100.00 |
| Saturated | 48.64 | 39.12 | 56.08 | 61.14 | 50.83 | 35.21 |
| Monounsaturated | 43.90 | 46.89 | 30.52 | 6.65 | 18.14 | 14.44 |
| Polyunsaturated | 7.45 | 13.99 | 13.41 | 32.20 | 31.02 | 50.35 |
| Total | 100.00 | 100.00 | 100.00 | 100.00 | 100.00 | 100.00 |
| Omega-3 | 5.51 | 11.94 | 11.11 | 32.20 | 28.87 | 47.69 |
| Omega-6 | 1.94 | 2.05 | 2.30 | 0.00 | 2.15 | 2.66 |

TABLE 9

Fatty acid composition of the phosphatidylcholine and the phosphatidylserine fractions (% (w/w)).

| Fatty Acid File | PC | | | PS | | |
|---|---|---|---|---|---|---|
| | Neutral KO | Polar KO | Neptune KO | Neutral KO | Polar KO | Neptune KO |
| C4:0 | 0.00 | 0.00 | 0.00 | 0.00 | 0.00 | 0.00 |
| C6:0 | 0.00 | 0.00 | 0.00 | 0.00 | 0.00 | 0.00 |
| C8:0 | 0.00 | 0.00 | 0.00 | 0.00 | 0.00 | 0.00 |
| C10:0 | 0.00 | 0.00 | 0.00 | 0.00 | 0.00 | 0.00 |
| C12:0 | 0.00 | 0.00 | 0.00 | 0.00 | 0.00 | 0.00 |
| C14:0 | 0.75 | 3.29 | 2.77 | 7.60 | 9.52 | 2.31 |
| C14:1 | 2.07 | 0.04 | 0.02 | 0.00 | 0.00 | 0.00 |
| C15:0 | 1.34 | 0.00 | 3.83 | 0.00 | 0.00 | 0.00 |
| C16:0 | 16.65 | 31.92 | 29.83 | 30.44 | 43.61 | 19.49 |
| C16:1 | 0.96 | 0.01 | 0.17 | 9.96 | 3.47 | 2.79 |
| C18:0 | 1.33 | 1.06 | 1.33 | 2.08 | 3.34 | 2.24 |
| C18:1 | 34.34 | 13.55 | 11.16 | 0.00 | 7.37 | 11.87 |
| C18:2N6 | 10.55 | 2.27 | 1.90 | 0.00 | 0.00 | 0.00 |
| C18:3N6 | 1.44 | 0.25 | 0.20 | 0.00 | 0.00 | 0.00 |
| C18:3N3 | 2.49 | 1.19 | 1.54 | 0.00 | 0.00 | 0.00 |
| C18:4N3 | 2.38 | 1.92 | 2.41 | 0.00 | 0.00 | 0.00 |
| C20:0 | 2.79 | 0.03 | 0.05 | 0.00 | 0.00 | 0.00 |
| C20:1 | 2.42 | 0.82 | 0.74 | 0.00 | 0.00 | 0.00 |
| C20:2N6 | 0.56 | 0.05 | 0.06 | 0.00 | 0.00 | 0.00 |
| C20:3N6 | 0.67 | 0.13 | 0.09 | 0.00 | 0.00 | 0.00 |
| C20:4N6 | 1.85 | 0.61 | 0.56 | 0.00 | 0.00 | 0.00 |
| C20:3N3 | 3.94 | 0.07 | 0.06 | 0.00 | 0.00 | 0.33 |
| C20:4N3 | 4.32 | 0.50 | 0.46 | 0.00 | 0.00 | 0.00 |
| C20:5N3 (EPA) | 1.08 | 29.85 | 30.09 | 25.84 | 15.81 | 16.35 |
| C22:0 | 0.00 | 0.05 | 0.02 | 0.00 | 0.00 | 0.00 |
| C22:1 | 2.77 | 0.00 | 1.87 | 0.00 | 0.00 | 0.00 |
| C22:2N6 | 0.00 | 0.81 | 0.97 | 0.00 | 0.00 | 0.00 |
| C22:4N6 | 0.00 | 0.01 | 0.02 | 0.00 | 0.00 | 0.00 |
| C22:5N6 | 1.49 | 0.01 | 0.00 | 0.00 | 0.00 | 0.00 |
| C22:5N3 | 1.48 | 0.67 | 0.68 | 0.00 | 0.00 | 0.00 |
| C22:6N3 (DHA) | 0.00 | 10.53 | 12.49 | 20.25 | 16.89 | 44.63 |

TABLE 9-continued

Fatty acid composition of the phosphatidylcholine and the phosphatidylserine fractions (% (w/w)).

| Fatty Acid File | PC | | | PS | | |
|---|---|---|---|---|---|---|
| | Neutral KO | Polar KO | Neptune KO | Neutral KO | Polar KO | Neptune KO |
| C24:0 | 2.34 | 0.10 | 0.18 | 0.00 | 0.00 | 0.00 |
| C24:1 | 0.00 | 0.25 | 0.34 | 0.00 | 0.00 | 0.00 |
| Total | 100.00 | 100.00 | 100.00 | 100.00 | 100.00 | 100.00 |
| Saturated | 25.19 | 36.46 | 34.18 | 43.95 | 56.47 | 24.04 |
| Monounsaturated | 42.56 | 14.67 | 14.29 | 9.96 | 10.84 | 14.65 |
| Polyunsaturated | 32.25 | 48.87 | 51.53 | 46.09 | 32.69 | 61.31 |
| Total | 100.00 | 100.00 | 100.00 | 100.00 | 100.00 | 100.00 |
| Omega-3 | 15.69 | 44.73 | 47.73 | 46.09 | 32.69 | 61.31 |
| Omega-6 | 16.56 | 4.13 | 3.81 | 0.00 | 0.00 | 0.00 |

TABLE 10

Fatty acid composition of the phosphatidylinositol and phophatidylethanolamine fractions (% (w/w)).

| Fatty Acid File | PI | | | PE | | |
|---|---|---|---|---|---|---|
| | Neutral KO | Polar KO | Neptune KO | Neutral KO | Polar KO | Neptune KO |
| C4:0 | 0.00 | 0.00 | 0.00 | 0.00 | 0.00 | 0.00 |
| C6:0 | 0.00 | 0.00 | 0.00 | 0.00 | 0.00 | 0.00 |
| C8:0 | 0.00 | 0.00 | 0.00 | 0.00 | 0.00 | 0.00 |
| C10:0 | 0.00 | 0.00 | 0.00 | 0.00 | 0.00 | 0.00 |
| C12:0 | 0.00 | 0.00 | 0.00 | 0.00 | 0.00 | 0.00 |
| C14:0 | 11.15 | 5.82 | 5.72 | 14.42 | 4.60 | 0.83 |
| C14:1 | 3.03 | 0.66 | 0.00 | 0.00 | 0.00 | 0.10 |
| C15:0 | 5.86 | 1.95 | 3.18 | 0.00 | 1.30 | 0.23 |
| C16:0 | 37.02 | 30.66 | 31.39 | 35.91 | 31.21 | 18.38 |
| C16:1 | 18.05 | 2.24 | 1.16 | 0.00 | 1.51 | 0.75 |
| C18:0 | 6.72 | 2.83 | 5.56 | 12.72 | 16.70 | 1.84 |
| C18:1 | 18.15 | 24.77 | 14.23 | 36.96 | 19.91 | 18.45 |
| C18:2N6 | 0.00 | 2.67 | 0.00 | 0.00 | 2.62 | 0.85 |
| C18:3N6 | 0.00 | 0.00 | 0.00 | 0.00 | 0.00 | 0.00 |
| C18:3N3 | 0.00 | 0.00 | 0.00 | 0.00 | 0.00 | 0.33 |
| C18:4N3 | 0.00 | 0.00 | 0.00 | 0.00 | 0.00 | 0.00 |
| C20:0 | 0.00 | 0.00 | 0.00 | 0.00 | 0.00 | 0.00 |
| C20:1 | 0.00 | 0.00 | 0.00 | 0.00 | 0.00 | 0.00 |
| C20:2N6 | 0.00 | 0.00 | 0.00 | 0.00 | 0.00 | 0.00 |
| C20:3N6 | 0.00 | 0.00 | 0.00 | 0.00 | 0.00 | 1.15 |
| C20:4N6 | 0.00 | 0.00 | 0.00 | 0.00 | 0.00 | 0.00 |
| C20:3N3 | 0.00 | 0.00 | 0.00 | 0.00 | 0.00 | 0.00 |
| C20:4N3 | 0.00 | 0.00 | 0.00 | 0.00 | 0.00 | 0.00 |
| C20:5N3 (EPA) | 0.00 | 17.60 | 20.45 | 0.00 | 10.76 | 21.26 |
| C22:0 | 0.00 | 0.00 | 0.00 | 0.00 | 0.00 | 0.00 |
| C22:1 | 0.00 | 0.00 | 0.00 | 0.00 | 0.00 | 0.00 |
| C22:2N6 | 0.00 | 0.00 | 0.00 | 0.00 | 0.00 | 0.00 |
| C22:4N6 | 0.00 | 0.00 | 0.00 | 0.00 | 0.00 | 0.00 |
| C22:5N6 | 0.00 | 0.00 | 0.00 | 0.00 | 0.00 | 0.00 |
| C22:5N3 | 0.00 | 0.00 | 0.00 | 0.00 | 0.00 | 0.67 |
| C22:6N3 (DHA) | 0.00 | 10.79 | 18.32 | 0.00 | 11.39 | 35.16 |
| C24:0 | 0.00 | 0.00 | 0.00 | 0.00 | 0.00 | 0.00 |
| C24:1 | 0.00 | 0.00 | 0.00 | 0.00 | 0.00 | 0.00 |
| Total | 100.00 | 100.00 | 100.00 | 100.00 | 100.00 | 100.00 |
| Saturated | 60.76 | 41.26 | 45.84 | 63.04 | 53.81 | 21.28 |
| Monounsaturated | 39.24 | 27.67 | 15.39 | 36.96 | 21.42 | 19.30 |
| Polyunsaturated | 0.00 | 31.07 | 38.77 | 0.00 | 24.77 | 59.42 |
| Total | 100.00 | 100.00 | 100.00 | 100.00 | 100.00 | 100.00 |
| Omega-3 | 0.00 | 28.40 | 38.77 | 0.00 | 22.15 | 57.43 |
| Omega-6 | 0.00 | 2.67 | 0.00 | 0.00 | 2.62 | 1.99 |

TABLE 11

Compositional data for the novel krill oil composition obtained and NKO krill oil.

| Compounds | Neptune KO | Ethanol extracted KO | Polar KO | Neutral KO |
|---|---|---|---|---|
| Astaxanthin esters | 472 mg/kg | 117 mg/kg | 580 mg/kg | 98 mg/kg |
| Astaxanthin free | 11 mg/kg | <1 mg/kg | <1 mg/kg | <1 mg/kg |
| Total cholesterol | 1 g/100 g | 12 g/100 g | <0.5 g/100 g | 5.7 g/100 g |

Example 4

Neutral lipids were extracted from krill meal (138 kg) using SFE with neat $CO_2$ (solvent ratio 25 kg/kg) at 500 bar and 75° C. The neutral lipids were fractionated at 200 bar (75° C.) and at 60 bar (35° C.) at two separators. The extract obtained at the first separator (S1—19.6 kg) was characterized, and the results can be found in Table 12. The extract obtained at the second separator (S2—0.4 kg) was rich in water, and was not further used. Next, the polar lipids were extracted using $CO_2$ at 500 bar, 20% ethanol and at a temperature of 75° C. Using a solvent ratio of 32 (kg/kg) and collecting an extract of 18.2 kg using a separator at 60 bars and 35° C. The polar lipids were collected and analyzed (see Table 13). Next, the polar lipids were mixed in a 50/50 ratio with the neutral lipids collected from the first separator before finally the ethanol was removed carefully by evaporation. The product obtained was red and transparent. If the ethanol is removed before the mixing if the fractions a transparent product is not obtained. The composition of the 50/50 red and transparent product can be found in Table 14.

TABLE 12

| | Unit | Amount |
|---|---|---|
| Fatty acid composition of the extract collected in S1 | | |
| Fatty acid | | |
| 14:0 | g/100 g | 18.4 |
| 16:0 | g/100 g | 22.2 |
| 18:0 | g/100 g | 1.5 |
| 16:1 n-7 | g/100 g | 10.9 |
| 18:1 (n-9) + (n-7) + (n-5) | g/100 g | 25.6 |
| 20:1 (n-9) + (n-7) | g/100 g | 1.8 |
| 22:1 (n-11) + (n-9) + (n-7) | g/100 g | 0.5 |
| 16:2 (n-4) | g/100 g | 1.3 |
| 16:4 (n-1) | g/100 g | 1.2 |
| 18:2 n-6 | g/100 g | 1.3 |
| 18:3 n-3 | g/100 g | 0.8 |
| 18:4 n-3 | g/100 g | 2.9 |
| 20:5 n-3 | g/100 g | 4.1 |
| 22:6 n-4 | g/100 g | 1.7 |
| Lipid class composition of the extract collected in S1 | | |
| Lipid | | |
| Triacylglycerol | g/100 g | 84 |
| Diacylglycerol | g/100 g | 0.7 |
| Free fatty acids | g/100 g | 1.5 |
| Cholesterol | g/100 g | 2.7 |
| Cholesterol esters | g/100 g | 0.9 |
| Miscellaneous analysis of the extract in S1. | | |
| Compound | | |
| Free astaxanthin | mg/kg | 4.3 |
| Astaxanthin esters | mg/kg | 462 |
| Trimethylamin | mg N/100 g | <1 |
| Trimethylamineoxide | mg N/100 g | 2 |

TABLE 13

| | Unit | Amount |
|---|---|---|
| Fatty acid composition of the extract collected after $CO_2$ and 20% ethanol in S1. | | |
| Fatty acid | | |
| 14:0 | g/100 g | 1.3 |
| 16:0 | g/100 g | 13.8 |
| 18:0 | g/100 g | 0.6 |
| 16:1 n-7 | g/100 g | 0.9 |
| 18:1 (n-9) + (n-7) + (n-5) | g/100 g | 6.5 |
| 20:1 (n-9) + (n-7) | g/100 g | 0.6 |
| 22:1 (n-11) + (n-9) + (n-7) | g/100 g | 0.1 |
| 16:2 (n-4) | g/100 g | <0.1 |
| 16:4 (n-1) | g/100 g | <0.1 |
| 18:2 n-6 | g/100 g | 0.8 |
| 18:3 n-3 | g/100 g | 0.6 |
| 18:4 n-3 | g/100 g | 1.0 |
| 20:5 n-3 | g/100 g | 14.7 |
| 22:6 n-4 | g/100 g | 6.5 |
| Lipid class composition of the extract collected after $CO_2$ and 20% ethanol in S1. | | |
| Lipid | | |
| Triacylglycerol | g/100 g | <0.5 |
| Cholesterol | g/100 g | <0.5 |
| Phophatidylethanolamine | g/100 g | 1.6 |
| Phosphatidylcholine | g/100 g | 67 |
| Lyso-phophatidylcholine | g/100 g | 4.4 |
| Miscellaneous analysis of the extract in S1. | | |
| Compound | | |
| Trimethylamin | mg N/100 g | 422 |
| Trimethylamineoxide | mg N/100 g | 239 |

TABLE 14

| | Unit | Amount |
|---|---|---|
| Fatty acid composition of the final blended product obtained in Example 4 in S1. | | |
| Fatty acid | | |
| 14:0 | g/100 g | 9.7 |
| 16:0 | g/100 g | 18.5 |
| 18:0 | g/100 g | 1.0 |
| 16:1 n-7 | g/100 g | 5.8 |
| 18:1 (n-9) + (n-7) + (n-5) | g/100 g | 16.0 |
| 20:1 (n-9) + (n-7) | g/100 g | 1.2 |
| 22:1 (n-11) + (n-9) + (n-7) | g/100 g | 1.0 |
| 16:2 (n-4) | g/100 g | 0.3 |
| 16:4 (n-1) | g/100 g | <0.1 |
| 18:2 n-6 | g/100 g | 1.0 |
| 18:3 n-3 | g/100 g | 0.8 |
| 18:4 n-3 | g/100 g | 2.1 |
| 20:5 n-3 | g/100 g | 10.7 |
| 22:6 n-4 | g/100 g | 4.7 |
| Lipid class composition of the final blended product obtained in Example 4. | | |
| Lipid | | |
| Triacylglycerol | g/100 g | 53 |
| Diacylglycerol | g/100 g | 1.3 |
| Free fatty acids | g/100 g | 0.5 |
| Cholesterol | g/100 g | 0.6 |
| Cholesterol esters | g/100 g | <0.5 |
| Phophatidylethanolamine | g/100 g | <1 |
| Phosphatidylcholine | g/100 g | 42 |
| Lyso-phophatidylcholine | g/100 g | 5.9 |

TABLE 14-continued

Miscellaneous analysis of the final blended product obtained in example 4.

| Compound | Unit | Amount |
|---|---|---|
| Free astaxanthin | mg/kg | 1.1 |
| Astaxanthin esters | mg/kg | 151 |
| Trimethylamin | mg N/100 g | 109 |
| Trimethylamineoxide | mg N/100 g | 80 |

Example 5

The asta oil obtained in Example 1 was blended with the polar lipids obtained in Example 4 in a ratio of 46:54 (v/v). Next the ethanol was removed by evaporation and a dark red and transparent product was obtained. The product was analyzed and the results can be found in Table 15. Furthermore, the product was encapsulated into soft gels successfully. During the encapsulation it was observed that any further increase in phospholipids, and thereby viscosity, will make it very difficult to encapsulate the final product.

TABLE 15

Fatty acid composition of the final blended product obtained in Example 5.

| Fatty acid | Unit | Amount |
|---|---|---|
| 14:0 | g/100 g | 8.2 |
| 16:0 | g/100 g | 17.7 |
| 18:0 | g/100 g | 1.0 |
| 16:1 n-7 | g/100 g | 4.9 |
| 18:1 (n-9) + (n-7) + (n-5) | g/100 g | 14.9 |
| 20:1 (n-9) + (n-7) | g/100 g | 1.1 |
| 22:1 (n-11) + (n-9) + (n-7) | g/100 g | 1.0 |
| 16:2 (n-4) | g/100 g | 0.4 |
| 16:4 (n-1) | g/100 g | <0.1 |
| 18:2 n-6 | g/100 g | 1.2 |
| 18:3 n-3 | g/100 g | 0.8 |
| 18:4 n-3 | g/100 g | 1.8 |
| 20:5 n-3 | g/100 g | 10.6 |
| 22:6 n-4 | g/100 g | 4.8 |

Lipid class composition of the final blended product obtained in Example 5.

| Lipid | | |
|---|---|---|
| Triacylglycerol | g/100 g | 41 |
| Diacylglycerol | g/100 g | 0.8 |
| Free fatty acids | g/100 g | 1.2 |
| Cholesterol | g/100 g | 0.4 |
| Cholesterol esters | g/100 g | 0.3 |
| Phophatidylethanolamine | g/100 g | 0.6 |
| Phosphatidylcholine | g/100 g | 51 |
| Lyso-phophatidylcholine | g/100 g | <0.5 |
| Total polar lipids | g/100 g | 52.4 |
| Total neutral lipids | g/100 g | 43.6 |

Miscellaneous analysis of the final blended product obtained in Example 5

| Compound | | |
|---|---|---|
| Free astaxanthin | mg/kg | 12 |
| Astaxanthin esters | mg/kg | 1302 |
| Trimethylamin | mg N/100 g | 193 |
| Trimethylamineoxide | mg N/100 g | 1.7 |

Example 6

Krill lipids were extracted from krill meal (a food grade powder) using supercritical fluid extraction with co-solvent. Initially, 300 bar pressure, 333° K and 5% ethanol (ethanol:$CO_2$, w/w) were utilized for 60 minutes in order to remove neutral lipids and astaxanthin from the krill meal. Next, the ethanol content was increased to 23% and the extraction was maintained for 3 hours and 40 minutes. The extract was then evaporated using a falling film evaporator and the resulting krill oil was finally filtered. The product obtained was then analyzed and the results can be found in Table 16.

TABLE 16

Analysis of the krill oil obtained using supercritical fluid extraction.

| Parameter | Value |
|---|---|
| Ethanol | 1.11% w/w |
| Water Content | 2.98% w/w |
| C20:5 n-3 (EPA) | 19.9 |
| C23:6 n-3 (DHA) | 11.3 |
| Total Omega 3 | 35.7 |
| Total Omega 6 | 3.0 |
| Total Phospholipids | 50.55 wt % |
| Ratio Omega3-PL/Total Omega 3 | 77.6% w/w |
| Ratio EPA-PL/Total EPA | 84.4% w/w |
| Ratio DHA-PL/Total DHA | 74.7% w/w |
| Triglycerides | 25.9 g/100 g |
| Astaxanthin | 2091 mg/kg |
| Peroxide Value | <0.1 |

Example 7

Krill oil was prepared according to the method described in Example 6 by extracting from the same krill meal. The oil was subjected to $^{31}P$ NMR analysis for the identification and quantification of the various forms of phospholipids. The analysis was performed according to the following methods: Samples (20-40 mg) were weighed into 1.5 ml centrifuge tubes. Next, NMR detergent (750 μl-10% Na cholate, 1% EDTA, pH 7.0 in $H_2O+D_2O$, 0.3 g L-1 PMG internal standard) was added. Next, the tube was placed in an oven at 60° C. and periodically shaken/sonicated until completely dispersed. The solution was then transferred to a 5 ml NMR tube for analysis. Phosphorus NMR spectra were recorded on the two-channel Bruker Avance300 with the following instrument settings: spectrometer frequency 121.498 MHz, sweep width 24,271 Hz, 64,000 data points, 30 degree excitation pulse, 576 transients were normally taken, each with an 8 second delay time and f.i.d. acquisition time of 1.35 sec. Spectra were processed with a standard exponential weighting function with 0.2 Hz line broadening before Fourier transformation.

Peaks were identified using known chemical shifts. Deacylation of samples with monomethylamine was also used on two samples for confirmation of peak identity and to achieve better peak resolution. Example spectra are presented in FIG. 1. Peak area integration gave relative molar amounts of each lipid class. Weight percent values were calculated using molecular masses calculated from a krill sample fatty acid profile (average chain length=18.6). Total PL levels were calculated from the PMG internal standard peak. The quantification of the phospholipids are shown in Table 17 for both the raw material, the final product and for a commercially available krill oil (Neptune Krill Oil). The main polar ether lipids of the krill meal are alkylacylphosphatidylcholine (AAPC) at 7-9% of total polar lipids, lyso-alkylacylphosphatidylcholine (LAAPC) at 1% of total polar lipids (TPL) and alkylacylphosphatidyl-ethanolamine (AAPE) at <1% of TPL.

TABLE 17

Phospholipid profiles

|  | Type B krill powder | NKO | Krill Oil obtained in Example 7 |
|---|---|---|---|
| PC | 66.0 | 68.6 | 75.3 |
| AAPC | 12.0 | 7.0 | 13.0 |
| PI |  |  |  |
| 1LPC | 1.2 | 1.3 | 0.4 |
| PS |  |  |  |
| 2LPC | 7.4 | 13.8 | 2.9 |
| LAAPC | 2.2 | 1.2 | 0.9 |
| PR | 6.0 | 3.4 | 3.4 |
| AAPE |  |  | 1.5 |
| SM |  |  |  |
| GPC |  | 1.3 |  |
| DHSM |  |  |  |
| NAPE |  | 3.4 |  |
| CL | 5.3 |  | 2.1 |
| LPE |  |  | 0.5 |
| LCL |  |  |  |
| % PL in powder or lipid sample | 8.3 | 30.0 | 47.9 |

Analysis has been carried out on the fatty acid and ether/alcohol profiles of the AAPC. The results are presented in Table 18.

TABLE 18

Fatty acid profile of the alkylacylphosphatidylcholine.

| AAPC fatty acid composition | AAPC alcohol composition | |
|---|---|---|
|  | alcohol | % |
| 20:5(n-3) - 46.9%; | 16:0 | 47.6 |
| 22:6(n-3) - 36.1%; | 18:1 | 17.8 |
| 18:1(n-9) - 4.6% | 16:1 | 14.1 |
| 22:5(n-3) - 2.6% | 14:0 | 10 |
| 20:4(n-6) - 1.9% | 18:0 | 8.6 |
| 21:5(n-3) - 1.5% | 18:2 | 5.1 |
| 18:2(n-6) - 0.9% | 17:0 | 4.4 |
| 16:1(n-9) - 0.8% | 15:0-i | 2.1 |
| 16:0-0.7% | 15:0 | 1.7 |
| phytanic - 0.6% | 20:1 | 1.4 |
| 18:3(n-3) - 0.5% | 15:0-a | 1.3 |
| 18:4(n-3) - 0.4% | 18:0-i | 0.4 |
| 18:1(n-7) - 0.4% |  |  |
| 24:1-0.4% |  |  |
| 14:0-0.3% |  |  |

The rest of alcohols (i17:0, etc.), were less than 0.3% each. Only part of 20:1 was confirmed by GC-MS. The alcohol moieties composition of Krill AAPC was determined (identification was performed in the form of 1-alkyl-2,3-diTMS glycerols on GC-MS, % of total fatty alcohols were obtained by GC with FID). Ten other fatty acids were all below 0.3% by mass.

Example 8

The purpose of this experiment was to investigate the effect of different omega-3 fatty acid sources on metabolic parameters in the Zucker rat. The Zucker rat is a widely used model of obesity and insulin resistance. Obesity is due to a mutation in the leptin receptor which impairs the regulation of intake. Omega-3 sources compared in this study were fish oil (FO) and two types of krill oil. The krill oil was either from a commercial supplier (Neptune® krill oil (NKO)) or prepared according to Example 6 (Superba™). Four groups of rats (n=6 per group) were fed ad lib either a control diet (CTRL) or a diet supplemented with a source of omega-3 fatty acids (FO, NKO, Superba). All diets supplied same amount of dietary fatty acids, oleic acid, linoleic acid and linolenic acid. Omega-3 diets (FO, NKO and Superba™) were additionally balanced for EPA and DHA content. The Zucker rats were 4 wk old at the start of the study with average initial weight of 250 g. At this stage the Zucker rats can be characterized as being pre-diabetic. Rats were fed the test diets for 4 wk after which they were sacrificed and blood and tissue samples were collected. This example shows that supplementation of the Zucker rat with krill oil prepared as in Example 7 results in an improvement of metabolic parameters characteristic of the obesity induced type two diabetic condition. The effect induced by the novel krill oil is often more pronounced than the effect of FO an in several cases greater than the effect induced by NKO. Specifically, the effects of the two types of krill oil differentiated with respect to the reduction of blood LDL cholesterol levels as well as lipid accumulation in the liver and muscle (FIGS. 2-9). Furthermore, the efficacy of transfer of DHA from the diet to the brain tissue was greatest with the krill oil prepared as in Example 6 (FIG. 10).

Example 9

The purpose of this experiment was to investigate the effect of dietary krill oil on metabolic parameters in high-fat fed mice and to compare the effect of dietary krill oil with that of fish oil containing the same amount of omega-3 fatty acids. Four groups of C57BL/6 mice (n=10 per group) were fed 1) chow (N), 2) high fat diet comprising 21% butter fat and 0.15% cholesterol (HF), 3) high fat diet+krill oil (HFKO) or 4) high fat diet+fish oil (HFFO). Treatment 3 contained 2.25% (w/w) krill oil as prepared in example 5 (except that the astaxanthin content was 500 ppm) which were equivalent to 0.36% omega-3 fatty acids. Treatment 4 also contained 0.36% omega-3 fatty acids obtained from regular 18-12 fish oil. The diets were fed to the mice for 7 weeks with free access to drinking water. Data represented in this example means+/−SE. Columns not sharing a common letter are significantly different (P<0.05) by ANOVA followed by Tukey's multiple comparison test. N=normal chow diet (n=10); HF=high-fat diet (n=10); HFFO=high-fat diet supplemented with fish oil (n=9); HFKO=high-fat diet supplemented with krill oil (n=8). The data are presented in FIGS. 12-19.

This example shows that supplementation of high-fat fed mice with krill oil results in an amelioration of diet-induced hyperinsulinemia, insulin resistance, increase in muscle lipid content (measured as a change in muscle mass), serum adiponectin reduction and hepatic steatosis. These potentially beneficial atheroprotective effects were similar or greater than those achieved with a supplement containing a comparable level of omega-3 fatty acids (see FIGS. 12-19).

Example 10

The effects of different omega-3 fatty acid sources on metabolic parameters in the Zucker rat were also investigated. The Zucker rat is a widely used model of obesity and insulin resistance. Obesity is due to a mutation in the leptin receptor which impairs the regulation of intake. Omega-3 sources compared in this study were fish oil (FO) and krill oil (KO). The KO was prepared by extracting the triacylglycerides and the phospholipids from the krill meal using supercritical $CO_2$ with ethanol so that the final oil consisted of at 50% phospholipids, 30% omega-3 fatty acids and around 1300 ppm astaxanthin. Three groups of rats (n=6 per group) were fed ad lib either a control diet (CTRL) or a diet supplemented with a source of omega-3 fatty acids (FO, KO). All diets supplied same amount of dietary fatty acids, oleic acid, linoleic acid and linolenic acid. Omega-3 diets were additionally balanced for EPA and DHA content (see Table 19).

TABLE 19

Fatty acid content of feeds used.

|      | tot n3 | totn6 | n6/n3 | tot UFA | tot SFA | UFA/SFA |
|------|--------|-------|-------|---------|---------|---------|
| CTRL | 0.264  | 2.073 | 7.845 | 4.682   | 2.318   | 2.020   |
| TAG  | 0.782  | 2.239 | 2.864 | 5.737   | 1.263   | 4.544   |
| KO   | 0.807  | 2.230 | 2.764 | 5.291   | 1.709   | 3.096   |

The Zucker rats were 4 wk old at the start of the study with average initial weight of 250 g. At this stage the Zucker rats can be non-insulin resistant. Rats were fed the test diets for 4 wk after which they were sacrificed and blood and tissue samples were collected. Table 20 shows the fatty acid composition of the triacylglycerides and the phospholipids for visceral adipose tissue, subcutaneous adipose tissue, liver and heart.

TABLE 20

Fatty acid composition of the VAT, SAT, Liver and Heart.

| | TAG | | | | | |
|---|---|---|---|---|---|---|
| | n3 18:3 | n3 20:5 | n3 22:5 | n3 22:6 | n6 18:2 | n6 20:4 |
| VISCERAL ADIPOSE TISSUE | | | | | | |
| CTRL | 37.729 [a] | 0.688 [a] | 2.508 [a] | 2.691 [a] | 254.513 [a] | 7.883 |
|      | 3.466 | 0.118 | 0.648 | 0.623 | 23.310 | 1.076 |
| FO   | 48.558 [a,t] | 18.667 [b] | 22.605 [b] | 29.567 [b] | 346.205 [b] | 8.622 |
|      | 10.211 | 3.902 | 5.408 | 7.103 | 68.345 | 1.192 |
| KO   | 51.564 [c] | 17.404 [b] | 23.647 [b] | 23.783 [b] | 385.790 [b] | 7.282 |
|      | 5.586 | 1.723 | 3.275 | 2.930 | 58.334 | 1.240 |
| SUBCUTANEOUS ADIPOSE TISSUE | | | | | | |
| CTRL | 46.415 [a] | 0.890 [a] | 2.664 [a] | 2.864 [a] | 427.638 | 10.131 [a] |
|      | 1.928 | 0.055 | 0.147 | 0.556 | 53.101 | 0.968 |
| FO   | 59.524 [b] | 20.026 [b] | 16.929 [b] | 31.099 [b] | 473.744 | 10.322 [a] |
|      | 2.017 | 1.206 | 0.949 | 2.316 | 19.382 | 0.517 |
| KO   | 51.999 [a,t] | 17.551 [b] | 16.691 [b] | 22.806 [b] | 496.642 | 7.157 [b] |
|      | 1.582 | 1.519 | 3.630 | 1.994 | 64.959 | 0.704 |
| LIVER | | | | | | |
| CTRL | 15.984 | 4.558 [a] | 5.037 [a] | 8.999 [a] | 159.189 | 33.181 |
|      | 2.351 | 1.424 | 1.835 | 3.180 | 18.602 | 8.791 |
| FO   | 26.911 | 77.719 [b] | 28.496 [b] | 96.935 [b] | 167.123 | 28.139 |
|      | 12.493 | 50.152 | 8.347 | 63.176 | 34.459 | 14.030 |
| KO   | 23.298 | 65.104 [b] | 54.627 [b] | 75.568 [b] | 232.367 | 23.517 |
|      | 5.370 | 26.535 | 30.682 | 30.757 | 58.808 | 8.067 |
| HEART | | | | | | |
| CTRL | 9.483 [a] | 1.590 [a] | 23.822 [a] | 23.281 [a] | 152.366 [a] | 38.420 [a] |
|      | 1.240 | 0.274 | 8.330 | 4.298 | 27.664 | 4.891 |
| FO   | 10.386 [a] | 10.002 [b] | 45.427 [b] | 57.068 [b] | 144.720 [a] | 26.780 [b] |
|      | 2.179 | 2.814 | 12.818 | 7.927 | 45.675 | 4.804 |
| KO   | 6.463 [b] | 8.173 [b] | 50.499 [b] | 48.747 [b] | 111.583 [b] | 19.826 [b] |
|      | 1.788 | 0.804 | 18.988 | 4.494 | 24.563 | 2.500 |

| | PL | | | | | |
|---|---|---|---|---|---|---|
| | n3 18:3 | n3 20:5 | n3 22:5 | n3 22:6 | n6 18:2 | n6 20:4 |
| VISCERAL ADIPOSE TISSUE | | | | | | |
| CTRL | | 0.019 [a] | 0.043 [a] | 0.124 [a] | 1.291 | 0.645 [a] |
|      | | 0.014 | 0.002 | 0.010 | 0.248 | 0.121 |
| FO   | | 0.061 [b] | 0.096 [b] | 0.248 [b] | 1.379 | 0.320 [b] |
|      | | 0.030 | 0.030 | 0.054 | 0.242 | 0.072 |
| KO   | | 0.111 [b] | 0.134 [b] | 0.373 [c] | 1.702 | 0.424 [b] |
|      | | 0.014 | 0.009 | 0.045 | 0.456 | 0.067 |

TABLE 20-continued

Fatty acid composition of the VAT, SAT, Liver and Heart.

SUBCUTANEOUS ADIPOSE TISSUE

| | | | | | | |
|---|---|---|---|---|---|---|
| CTRL | | 0.004 [a] | 0.017 | 0.040 | 0.304 | 0.335 |
| | | 0.003 | 0.006 | 0.025 | 0.067 | 0.096 |
| FO | | 0.035 [b] | 0.021 | 0.047 | 0.282 | 0.260 |
| | | 0.012 | 0.011 | 0.025 | 0.043 | 0.111 |
| KO | | 0.021 [b] | 0.022 | 0.073 | 0.236 | 0.268 |
| | | 0.014 | 0.000 | 0.032 | 0.104 | 0.103 |

LIVER

| | | | | | | |
|---|---|---|---|---|---|---|
| CTRL | 0.607 | 0.994 [a] | 3.496 [a] | 23.372 [a] | 23.274 [a] | 72.149 |
| | 0.540 | 0.000 | 1.786 | 6.123 | 11.233 | 18.769 |
| FO | 1.494 | 19.770 [b] | 14.935 [b] | 89.729 [b] | 57.491 [b] | 115.675 |
| | 0.439 | 0.000 | 7.415 | 59.748 | 27.479 | 79.309 |
| KO | 1.459 | 29.158 [b] | 18.445 | 101.450 [b] | 70.619 [b] | 133.981 |
| | 0.916 | 0.000 | 6.156 | 46.934 | 16.126 | 58.640 |

HEART

| | | | | | | |
|---|---|---|---|---|---|---|
| CTRL | 2.273 | 2.270 [a] | 37.548 [a] | 118.815 [a] | 302.295 [a] | 263.031 [a] |
| | 0.365 | 0.560 | 5.905 | 24.674 | 25.788 | 12.649 |
| FO | 1.729 | 18.182 [b] | 53.216 [a,t] | 177.093 [b] | 380.252 [a,t] | 181.710 [b] |
| | 0.278 | 1.580 | 21.323 | 10.530 | 186.140 | 7.456 |
| KO | 2.514 | 35.750 [c] | 63.534 [b] | 252.017 [b] | 525.519 [b] | 266.554 [a] |
| | 0.245 | 3.652 | 3.307 | 28.366 | 152.206 | 22.517 |

This example shows that supplementation of the Zucker rat with krill oil prepared as described above resulted in a reduction in the levels of anandamide (AEA) and 2-arachidonoyl glycerol (2-AG) in visceral adipose tissue (FIG. 20A-B). In subcutaneous fat, the level of 2-AG were reduced compared to fish oil and control (FIG. 21A-B). In liver and heart (FIGS. 22A-B and 23A-B, respectively) the level of AEA was most efficiently reduced with krill oil.

Furthermore, the triacylglycerol content in tissues was measured as well. FIGS. 24 and 25 show the TAG deposition in the liver and heart, respectively. In both tissues, krill oil is the most effective in reducing ectopic fat deposition. FIG. 26 shows the cholesterol profile in rat plasma, and again krill oil is the most effective treatment. FIG. 27 shows the fatty acid profile of the monocytes. Clearly, krill oil is most effective in reducing the level of arachidonic acid and thereby reducing the inflammatory potential of the monocytes. FIG. 28 shows the level of TNF-alpha after lipopolysaccharide (LPS) challenge, and both krill and fish oils show a reduced level of TNF-alpha release compared to the control.

Example 11

In this example, the effects on lipid metabolism, ectopic fat deposition, and susceptibility to inflammation in Zucker fa/fa rats were studied. Relatively low doses of dietary (n-3) LCPUFA were administered as FO or KO. Fatty acid profiles and endocannabinoid concentrations were determined in different tissues to examine the possible impact of (n-3) LCPUFA on the dysregulated endocannabinoid system of Zucker rats, which were fed a diet containing 0.8% of energy (n-3) LCPUFA, a level lower than that typically used in rodent studies, to allow a more meaningful comparison with human studies.

Eighteen male Zucker rats (Harlan) 4 wk of age were divided into 3 groups and fed for 4 wk a control diet (C) or diets supplemented with either FO (GC Rieber Oils) or KO (Superba, Aker BioMarine). The diets were based on the AIN-93G formulation, with substitution of soybean oil with a blend of oils (rapeseed oil, sunflower oil, coconut oil, and linseed oil). This allowed the 3 diets to be similar for total fatty acids and for oleic, linoleic (LA), and a-linolenic (ALA) acids. FO and KO diets were further balanced for EPA and DHA content (see Table 21). The 3 diets were prepared by Altromin GmbH & Co. KG and stored in vacuum bags to reduce (n-3) LCPUFA oxidation. The amount of 0.5 g EPA+DHA/100 g of diet, equivalent to 0.8% of energy in the rat diet, was chosen to provide a level of (n-3) LCPUFA intake achievable in humans and corresponds to 1.8 g/d in an 8.4-MJ/d diet in humans. All experiments were performed according to the guidelines and protocols approved by the European Union (EU Council 86/609; D.L. 27.01.1992, no. 116) and by the Animal Research Ethics Committee of the University of Cagliari, Italy.

TABLE 21

Dietary Fatty Acid Composition.

| Fatty acid | C | FO | KO |
|---|---|---|---|
| | | g/100 g diet | |
| 18:3(n-3) | 0.25 | 0.25 | 0.29 |
| 18:4(n-3) | 0.00 | 0.05 | 0.08 |
| 20:5(n-3) | 0.00 | 0.29 | 0.80 |
| 22:8(n-3) | 0.00 | 0.18 | 0.14 |
| Total (n-3) | 0.28 | 0.78 | 0.81 |
| 18:2(n-8) | 2.07 | 2.23 | 2.22 |
| 20:4(n-5) | 6.00 | 0.01 | 0.01 |
| Total (n-5) | 2.07 | 2.24 | 2.23 |
| (n-8):(n-3) | 7.85 | 2.85 | 2.75 |
| 18:1(n-9) | 2.34 | 2.72 | 2.25 |
| Total UFA | 4.68 | 5.74 | 5.29 |
| 12:0 | 1.09 | 0.04 | 0.02 |
| 14:0 | 0.39 | 0.20 | 0.38 |
| 16:0 | 0.58 | 0.78 | 1.08 |
| 18:0 | 0.22 | 0.21 | 0.19 |
| 20:0 | 0.03 | 0.04 | 0.03 |
| Total SFA | 2.32 | 1.26 | 1.71 |
| UFA-SFA | 2.02 | 4.54 | 3.10 |

Rats were food-deprived overnight and macrophages were isolated from their peritoneal cavity. The rats were deeply anesthetized with sodium pentobarbital (50 mg/kg intraperitoneally; Sigma-Aldrich) before being killed. Cells were obtained by peritoneal lavage with 60 mL of cold PBS containing 5 mmol/L EDTA. The rats were subjected to a vigorous massage of the peritoneal area prior to collection of cells. Immediately after death, blood was drawn from aorta, and liver, brain, heart, subcutaneous adipose tissues (SAT), and visceral adipose tissues (VAT) were removed and stored at 280° C.

Cells were centrifuged at 300×g; 10 min and the cell pellet was washed twice with cold sterile PBS and suspended in DMEM, 10% heat-inactivated fetal calf serum, penicillin (100 kU/L), and streptomycin (100 mg/L). The cell number was determined with a Coulter Counter corrected for viability determined by tryptan blue dye exclusion. The cells were then seeded at the density of $4.0 \times 10^5$ cells $cm^2$ and incubated for 2 h at 37° C. and 5% $CO_2$ atm. After removing nonadherent cells, macrophages were cultured in DMEM with 10% fetal calf serum in the presence of lipopolysaccharide (LPS) from *Escherichia coli* 026:B6 (Sigma Aldrich) (100 mg/L) for 24 h. The incubation time was chosen based on preliminary experiments that showed no substantial difference in cytokine secretion between 24 and 48 h. At the time indicated, supernatants and cells were separated and stored at 280° C. until ELISA and fatty acid analysis were performed. Sandwich ELISA tests were carried out all at the same time to avoid variations during the assay conditions and performed as described by the manufacturer.

Serum C-reactive protein (Chemicon International), tumor necrosis factor-a (TNFa), interleukin (IL)-10, and tumor growth factor-b (TGFb) (Biosource) were determined by a sandwich ELISA. Moreover, to evaluate macrophage susceptibility to inflammatory ligands, the secretion of TNFa, IL-6 (Bender MedSystem), IL-1b, IL-10, and TGFb were assessed in culture supernatants from peritoneal macrophages activated with LPS. Media were assayed at 800×g; 10 min to remove debris. Supernatants were frozen at 280° C. until assayed with a sandwich ELISA (Biosource).

Total lipids were extracted from tissues using chloroform: methanol 2:1 (v:v). Separation of total lipids into TAG and PL was performed as previously reported. Aliquots were mildly saponified as previously described to obtain FFA for HPLC analysis. Separation of fatty acids was conducted with a Hewlett-Packard 1100 HPLC system (Hewlett-Packard) equipped with a diode array detector as previously reported. Because SFA are transparent to UV, they were measured, after methylation, by means of a gas chromatograph (Agilent, Model 6890) equipped with split ratio of 20:1 injection port, a flame ionization detector, an autosampler (Agilent, Model 7673), a 100-m HP-88 fused capillary column (Agilent), and an Agilent ChemStation software system. The injector and detector temperatures were set at 250° C. and 280° C., respectively. $H_2$ served as carrier gas (1 mL/min) and the flame ionization detector gases were $H_2$ (30 mL/min), $N_2$ (30 mL/min), and purified air (300 mL/min). The temperature program was as follows: initial temperature was 120° C., programmed at 10° C./min to 210° C. and 5° C./min to 230° C., then programmed at 25° C./min to 250° C. and held for 2 min.

AEA and 2-AG were measured. MAGL and FAAH activities were determined in the heart, liver, VAT, and SAT from C and FO- and KO-supplemented rats. In particular, 2-AG hydrolysis (mostly by MAGL) was measured by incubating the 10,000×g cytosolic fraction of tissues (100 mg per sample) in Tris-HCl 50 mmol/L, at pH 7.0 at 37° C. for 20 min, with synthetic 2-arachidonoyl-[$^3$H]-glycerol (40 Ci/mmol, ARC) properly diluted with 2-AG (Cayman Chemicals). After incubation, the amount of [$^3$H]-glycerol produced was measured by scintillation counting of the aqueous phase after extraction of the incubation mixture with 2 volumes of $CHCl_3$:MeOH 1:1 (v:v). AEA hydrolysis (by FAAH) was measured by incubating the 10,000×g membrane fraction of tissues (70 mg per sample) in Tris-HCl 50 mmol/L, at pH 9.0-10.00 at 37° C. for 30 min, with synthetic N-arachidonoyl-[$^{14}$C]-ethanolamine (110 mCi/mmol, ARC) properly diluted with AEA (Tocris Bioscience). After incubation, the amount of [$^{14}$C]-ethanolamine produced was measured by scintillation counting of the aqueous phase after extraction of the incubation mixture with 2 volumes of $CHCl_3$:MeOH 1:1 (by vol.). Values in the text are means±SD.

The one-way ANOVA and the Bonferroni test for post hoc analyses were applied to evaluate statistical differences among groups. Where variances were unequal, Kruskal-Wallis non-parametric 1-way ANOVA was used.

Growth and food intake did not differ among the 3 groups and none of the rats exhibited adverse effects (data not shown). At the end of the 4-wk treatment, the body weight of the rats was 400±35 g.

In KO-supplemented rats, and to a lesser extent in the FO group, the liver TAG concentration was significantly lower than in C (FIG. 29A). The heart TAG concentration was significantly lower than C only in KO-supplemented rats (FIG. 29B).

Rats supplemented with FO or KO had 75% lower plasma LDL cholesterol concentrations than C, whereas HDL cholesterol did not differ among the groups (FIG. 32A). Conversely, triglyceridemia was ~30% higher than C in both (n-3) LCPUFA-supplemented groups (FIG. 32B).

Plasma proinflammatory (TNFa, IL-6, IL-1b) and anti-inflammatory cytokines (IL-10 and TGFb) and C-reactive protein did not differ among the experimental groups (see Table 22).

TABLE 22

Plasma levels of inflammatory markers in rats fed Control (C), Fish Oil (FO), or Krill Oil (KO) diets.

|  | C | FO | KO |
|---|---|---|---|
|  |  | mg/L plasma |  |
| TNFα | 17.2 ± 2.0 | 19.4 ± 3.4 | 19.1 ± 5.2 |
| IL-10 | 10.3 ± 0.6 | 9.8 ± 0.9 | 10.9 ± 1.5 |
| CRP | 382.2 ± 51.7 | 356.8 ± 119.8 | 414.7 ± 42.0 |
| TGFβ | 39.4 ± 2.1 | 43.9 ± 2.9 | 39.7 ± 5.0 |

Values are mean ± SD, n = 6.
No significant differences among the experimental groups were detected In macrophages incubated for 24 h in the presence of LPS, TNFa secretion was significantly lower in FO and KO rats compared with C (see Table 23). Plasma IL-1b, IL-6, and IL-10 concentrations did not differ among dietary groups following LPS stimulation.

TABLE 23

TNF-alpha release in LPS-treated peritoneal macrophages from Obese Zucker rats fed C, FO, or KO diets for four weeks.

|  | C | FO | KO |
|---|---|---|---|
|  |  | mg/L plasma |  |
| Basal | 9.6 ± 0.1 | 1.9 ± 0.7 | 0.3 ± 0.1 |
| LPS | 68.4 ± 9.4$^a$ | 37.2 ± 9.7$^b$ | 42.2 ± 3.2$^b$ |

$^a$Values are mean ± SD, n = 8.
$^b$in a row with superscripts without connection letter differ, P < 0.05.

The VAT AEA concentration was lower in the FO and KO groups than in C (FIG. 30A), whereas 2-AG was significantly lower than C only in the KO-supplemented rats (FIG. 30B). Endocannabinoid concentrations in SAT did not differ among the 3 groups.

Liver and heart endocannabinoids were similarly affected in the KO-supplemented rats (FIG. 31A-D). AEA concentrations were ~25% of, and 2-AG concentrations ~200% of, those of C in both tissues. In FO-fed rats, liver but not heart AEA concentrations were less than in C.

Activities of enzymes involved in endocannabinoid degradation. Changes in FAAH and MAGL activity have been observed in adipose tissues and liver of obese individuals and rodents. In this study, heart, liver, VAT, and SAT FAAH activities did not differ among the experimental groups (see Table 24). Conversely, MAGL activity was significantly lower in the VAT of the FO and KO groups, and in the heart tissue of the KO group, compared with C (see Table 24). Liver MAGL activity tended to be lower in both groups compared with C (P=0.1).

TABLE 24

FAAH and MAGL activities in the heart, liver, VAT, and SAT of Obese Zucker rats fed C, FO, or KO diets for four weeks.

| Tissue and diet group | FAAH | MAGL |
|---|---|---|
| | pmol/(min · mg tissue) | |
| Heart | | |
| C | 4.8 ± 2.6 | 2442.7 ± 62.2$^a$ |
| FO | 4.1 ± 1.3 | 2169.8 ± 10.1$^{a,b}$ |
| KO | 4.0 ± 1.4 | 2072.6 ± 168.4$^b$ |
| Liver | | |
| C | 208.0 ± 4.5 | 2075.3 ± 6.6 |
| FO | 207.6 ± 4.9 | 1958.6 ± 106.7 |
| KO | 208.9 ± 3.9 | 1938.7 ± 110.4 |
| VAT | | |
| C | 9.7 ± 3.2 | 1627.5 ± 151.8$^a$ |
| FO | 7.0 ± 2.7 | 1257.8 ± 49.0$^b$ |
| KO | 0.2 ± 0.8 | 1217.4 ± 18.8$^b$ |
| SAT | | |
| C | 29.6 ± 1.3 | 1279.2 ± 8.3 |
| FO | 14.1 ± 3.8 | 1316.3 ± 24.7 |
| KO | 50.4 ± 25.3 | 1277.8 ± 45.1 |

[1]Values are mean ± SD, n = 4.
Within a tissue, means in a column with superscripts without a connection letter differ, P < 0.05.

Plasma EPA and DHA concentrations were higher and that of ARA was lower in the FO and KO groups compared with C (see Table 25). Interestingly, the levels of ALA and LA (only in the KO group) were higher than in C despite the similar levels of these fatty acids in the diets (see Table 21). Peritoneal macrophages from FO- and KO-fed rats had significantly higher EPA and DHA and lower ARA concentrations than those from the C group (see Table 26).

TABLE 25

TNF-alpha release in LPS-treated peritoneal macrophages from rats fed Control (C), Fish Oil (FO), or Krill Oil (KO) diets.

| | C | FO | KO |
|---|---|---|---|
| | | mg/L plasma | |
| Basal | 0.6 ± 0.1* | 1.9 ± 0.7$^a$ | 0.3 ± 0.1* |
| LPS | 68.4 ± 9.4$^a$ | 37.2 ± 9.7$^b$ | 42.2 ± 3.2$^b$ |

Values are mean ± SD, n = 6.
Different letters denote significant differences (p < 0.05).
*In all those dietary groups.
LPS treatment increased TNF α release significantly (p < 0.05).

TABLE 26

20:5(n-3), 22:6(n-3), and 20:4(n-6) concentrations in peritoneal macrophages from rats fed Control (C), Fish Oil (FO), or Krill Oil (KO) diets (expressed as mol % of total fatty acids).

| | C | FO | KO |
|---|---|---|---|
| | | mol % | |
| 20:4(n-6) | 8.9 ± 2.6$^a$ | 7.9 ± 1.5$^a$ | 5.3 ± 1.0$^b$ |
| 20:5(n-3) | 0.3 ± 0.1$^a$ | 2.2 ± 0.1$^b$ | 1.4 ± 0.4$^b$ |
| 22:6(n-3) | 0.8 ± 0.5$^a$ | 2.1 ± 0.3$^b$ | 1.5 ± 0.5$^b$ |

Values are mean ± SD, n = 6.
Different letters denote significant differences (p < 0.05).

Dietary (n-3) LCPUFA influenced the TAG fraction of VAT and SAT with greater incorporation of EPA, DPA, and DHA in both experimental groups compared with C (see Table 27). The EPA and DHA levels in SAT were higher in FO- than in KO-treated rats. ARA was significantly lower than in C only in SAT of KO-supplemented rats; there was no difference among the groups in VAT. As in plasma, ALA was higher than in C in both VAT and SAT of FO and KO groups. On the contrary, LA was significantly higher only in VAT of (n-3) LCPUFA supplemented rats compared with C. In all 3 dietary groups, remarkable differences in fatty acid profiles of the PL fraction were observed, also between VAT and SAT (see Table 27). PL ARA levels of the VAT, but not SAT, were significantly less in FO- and KO-supplemented rats than in C. Levels of EPA, DPA, and DHA were higher in the (n-3) LCPUFA-supplemented rats compared with C in VAT PL, while only EPA changed significantly in SAT PL.

TABLE 27

PUFA composition of visceral and subcutaneous adipose tissues from rats fed Control (C), Fish Oil (FO), or Krill Oil (KO) diets.

| | TAG | | | | | | PL |
|---|---|---|---|---|---|---|---|
| | nmol/mg lipid | | | | | | nmol/mg lipid |
| | 18:3(n-3) | 20:5(n-3) | 22:5(n-3) | 22:6(n-3) | 18:2(n-6) | 20:4(n-6) | 18:3(n-3) |
| VISCERAL ADIPOSE TISSUE | | | | | | | |
| C | 37.7 ± 3.5$^a$ | 0.7 ± 0.1$^a$ | 2.5 ± 0.7$^a$ | 2.7 ± 0.6$^a$ | 254.5 ± 23.3$^a$ | 7.9 ± 1.1 | |
| FO | 48.6 ± 10.2$^{a,b}$ | 18.7 ± 3.9$^b$ | 22.6 ± 5.4$^b$ | 29.6 ± 7.1$^b$ | 346.2 ± 68.3$^b$ | 8.6 ± 1.2 | |
| KO | 51.6 ± 5.6$^b$ | 17.4 ± 1.7$^b$ | 23.7 ± 3.3$^b$ | 23.8 ± 2.9$^b$ | 385.8 ± 58.3$^b$ | 7.3 ± 1.2 | |
| SUBCUTANEOUS ADIPOSE TISSUE | | | | | | | |
| C | 46.4 ± 1.3$^a$ | 0.9 ± 0.1$^a$ | 2.7 ± 0.2$^a$ | 2.9 ± 0.6$^a$ | 427.6 ± 53.1 | 10.1 ± 1.0$^a$ | |
| FO | 59.5 ± 2.0$^b$ | 20.0 ± 1.2$^b$ | 16.9 ± 0.9$^b$ | 31.1 ± 2.3$^b$ | 473.7 ± 19.4 | 10.3 ± 0.5$^a$ | |
| KO | 52.0 ± 1.6$^c$ | 17.6 ± 1.5$^c$ | 16.7 ± 3.6$^b$ | 22.8 ± 2.0$^c$ | 496.7 ± 65.0 | 7.2 ± 0.7$^b$ | |

TABLE 27-continued

PUFA composition of visceral and subcutaneous adipose tissues from rats fed Control (C), Fish Oil (FO), or Krill Oil (KO) diets.

| | | PL nmol/mg lipid | | | | |
|---|---|---|---|---|---|---|
| | | 20:5(n-3) | 22:5(n-3) | 22:6(n-3) | 18:2(n-6) | 20:4(n-6) |
| | | VISCERAL ADIPOSE TISSUE | | | | |
| | C | 0.01 ± 0.01$^a$ | 0.04 ± 0.01$^a$ | 0.1 ± 0.01$^a$ | 1.3 ± 0.3 | 0.6 ± 0.1$^a$ |
| | FO | 0.06 ± 0.03$^b$ | 0.1 ± 0.03$^b$ | 0.3 ± 0.05$^b$ | 1.4 ± 0.2 | 0.3 ± 0.1$^b$ |
| | KO | 0.1 ± 0.01$^c$ | 0.1 ± 0.01$^c$ | 0.4 ± 0.04$^c$ | 1.7 ± 0.5 | 0.4 ± 0.1$^b$ |
| | | SUBCUTANEOUS ADIPOSE TISSUE | | | | |
| | C | 0.004 ± 0.003$^a$ | 0.02 ± 0.006 | 0.04 ± 0.02 | 0.3 ± 0.1 | 0.3 ± 0.1 |
| | FO | 0.03 ± 0.01$^b$ | 0.02 ± 0.01 | 0.05 ± 0.02 | 0.3 ± 0.04 | 0.3 ± 0.1 |
| | KO | 0.02 ± 0.01$^b$ | 0.02 ± 0.003 | 0.07 ± 0.03 | 0.2 ± 0.1 | 0.3 ± 0.1 |

Value are mean ± SD, n = 6. Different letters denote significant differences (p < 0.05).

TABLE 28

PUFA composition of liver and heart from rats fed Control (C), Fish Oil (FO), or Krill Oil (KO) diets.

| | TAG nmol/mg lipid | | | | | | PL nmol/mg lipid |
|---|---|---|---|---|---|---|---|
| | 18:3(n-3) | 20:5(n-3) | 22:5(n-3) | 22:6(n-3) | 18:2(n-6) | 20:4(n-6) | 18:3(n-3) |
| | LIVER | | | | | | |
| C | 16.0 ± 2.3 | 4.6 ± 1.4a | 5.0 ± 1.8a | 9.0 ± 3.2a | 159.2 ± 18.6 | 33.2 ± 8.8 | 0.6 ± 0.54 |
| FO | 26.9 ± 12.5 | 77.7 ± 50.1b | 28.5 ± 8.3b | 96.9 ± 63.2b | 167.1 ± 34.5 | 28.1 ± 14.0 | 1.5 ± 0.44 |
| KO | 23.3 ± 5.4 | 65.1 ± 26.5b | 54.6 ± 30.7b | 75.6 ± 30.8b | 232.4 ± 58.8 | 23.5 ± 8.1 | 1.5 ± 0.92 |
| | HEART | | | | | | |
| C | 9.5 ± 1.2a | 1.6 ± 0.3a | 23.8 ± 8.3a | 23.3 ± 4.3a | 152.4 ± 27.7 | 38.4 ± 4.9a | 2.3 ± 0.4 |
| FO | 10.4 ± 2.2a | 10.0 ± 2.8b | 45.4 ± 12.8a | 57.1 ± 7.9b | 144.7 ± 45.7 | 26.78 ± 4.8b | 1.7 ± 0.3 |
| KO | 6.5 ± 1.8b | 8.2 ± 0.8b | 50.5 ± 19.0b | 48.7 ± 4.5b | 111.6 ± 24.6b | 19.82 ± 2.6b | 2.5 ± 0.2 |

| | | PL nmol/mg lipid | | | | |
|---|---|---|---|---|---|---|
| | | 20:5(n-3) | 22:5(n-3) | 22:6(n-3) | 18:2(n-6) | 20:4(n-6) |
| | | LIVER | | | | |
| | C | 1.0 ± 0.2a | 3.5 ± 1.8a | 23.4 ± 6.1a | 23.3 ± 11.2a | 72.1 ± 18.8 |
| | FO | 19.8 ± 4.5b | 14.9 ± 7.4b | 89.7 ± 59.7a | 57.5 ± 27.5b | 115.68 ± 79.3 |
| | KO | 29.2 ± 6.3c | 18.4 ± 6.2b | 101.4 ± 46.9b | 70.6 ± 16.1b | 133.98 ± 58.6 |
| | | HEART | | | | |
| | C | 2.27 ± 0.6a | 37.5 ± 5.9a | 118.8 ± 24.7a | 302.3 ± 25.8 | 263.0 ± 12.6a |
| | FO | 18.18 ± 1.6b | 53.2 ± 21.3a,b | 177.1 ± 10.57b | 380.2 ± 186.1 | 181.7 ± 7.5b |
| | KO | 35.75 ± 3.6c | 63.5 ± 3.3b | 252.0 ± 28.4c | 525.5 ± 152.2 | 266.5 ± 22.5a |

Value are mean ± SD, n = 6. Different letters denote significant differences (p < 0.05)

In liver TAG, EPA, DPA, and DHA levels were significantly elevated in the FO and KO groups compared with C, whereas ARA levels did not differ among the groups. In liver PL, EPA and DPA concentrations were greater in both (n-3) LCPUFA supplemented groups than in C, whereas DHA was significantly higher than C only in the KO group. LA was significantly greater in the (n-3) LCPUFA-supplemented groups than in C, whereas the ARA level did not differ (see Table 28). The heart TAG fatty acid profile had higher levels of EPA, DPA, and DHA and lower levels of ARA in the FO and KO groups compared with C. LA and ALA concentrations were lower than in C only in the KO-supplemented rats. In the PL fraction of the (n-3) LCPUFA-supplemented groups, concentrations of EPA, DPA, and DHA were also greater than C, with higher levels in the KO group, whereas ARA was significantly less than in C only in the FO group (see Table 28).

Example 12

Male CBA/J mice were purchased from Jackson Laboratory at six weeks of age and were individually housed and fed 84 kcal/week of a control AIN93M diet. At two months of age, mice were transferred to one of six test diets (10 mice per diet): Control, a diet supplemented with fish oil, (FO), and a diet supplemented with Superba krill oil (KO). All mice received 84 kcal/week. The supplemented diets were based on modifications of the Control diet as described in Table 29. Amounts of each component are shown as grams of that component per kilogram of diet.

TABLE 29

Lipid and protein sources for the diets.

| | Control | Fish oil | Krill oil |
|---|---|---|---|
| Lipid source | 40 g soybean oil | 29 g soybean oil; 11 g fish oil | 25 g soybean oil; 15 g krill oil |
| Protein source | 140 g casein | 140 g casein | 140 g casein |

Body weight was measured approximately two times per month and were similar in all groups. At five months of age, mice were euthanized by cervical dislocation, blood was collected from the body cavity, and tissues were rapidly dissected, flash frozen in liquid nitrogen, and stored at −80° C. Gene expression profiling was performed. Total RNA was extracted from liver tissue of seven mice per group and was processed according to standard protocols described by Affymetrix. Samples were hybridized on the Affymetrix Mouse Genome 430 2.0 array, which allows from the detection of approximately 20,000 known genes. To determine the effect of a test diet on the expression of a gene, the average signal intensity for the treated group was compared to the average signal intensity for that gene in the Control group. Comparisons between groups were made using two-tailed t-tests (experimental vs. Control); a gene was considered to be significantly changed by treatment at $p<0.01$.

To identify functional classes of genes changed by treatment Parametric Analysis of Gene set Enrichment (PAGE) was performed. This technique allows for an unbiased and highly sensitive method of detecting classes of genes that are modulated by treatment. In addition, PAGE determines a z-score indicating if a gene class was activated (z-score >0) or repressed (z-score <0) by treatment. Genes were grouped into functional classes using the Gene Ontology (GO) hierarchy, and GO terms that were annotated with at least 10 but not more than 1000 genes per term were considered. GO terms were considered to be significantly altered by treatment at $p<0.001$. A global comparison of the GO Biological Processes modulated by diet was made, which showed that fish oil is less bioactive than krill oil. Moreover, in several cases (e.g., lipid biosynthesis and fatty acid metabolism), the overall effect of fish oil was in the opposite direction as observed with the KO diet.

The effect of diet on glucose metabolism was studied. PAGE analysis revealed that the GO term "glucose metabolism" was decreased in the FO and KO diets (p=0.004-6). The ability of n-3 PUFAs to decrease glucose metabolism compared to the control diet with the same energy intake may be regulated at the early stages of glycolysis by decreasing glucose uptake though the liver glucose transporter (Glut2/S1c2a2) and by decreased phosphorylation through the liver enzyme glucokinase (Gck). KO showed a trend for decreased S1c2a2 expression (p=0.030; see FIG. 34). It is important to note that the majority of the carbohydrate in the diets used in this study comes from sucrose (composed of glucose and fructose), and interestingly, there appears to be a shift favoring fructose metabolism in mice fed diets containing KO. As shown in FIG. 34, expression of two genes involved in fructose metabolism tended to be greater in the KO group: Ketohexokinase (Khk) converts fructose to fructose-1-phosphate, and aldolase B (Aldob) converts fructose-1-phosphate into compounds which can enter glycolysis or be used to synthesize glycogen. Taken together, the decrease in glucose metabolism and shift towards hepatic fructose metabolism suggest that krill oil supplementation acts to preserve glucose for tissues such as brain or muscle.

PAGE also revealed a trend for decreased gluconeogenesis in the KO group, with a nearly significant decrease in this pathway (p=0.040). In addition to the genes annotated in this Gene Ontology term, there are several well-known genes that regulate hepatic glucose production but are not annotated by the Gene Ontology consortium; interestingly, these genes showed a strong trend to be regulated in the KO group (see FIG. 35) providing further evidence for decreased hepatic gluconeogenesis. Two of these genes (Ppargc1a and Hnf4a) are master regulators of metabolic gene transcription, and they have potent physiological effects on hepatic gluconeogenesis/glucose production. These genes encode proteins that regulate metabolism by binding to DNA and enhancing the expression of other metabolic genes in many tissues. In the liver of humans with type 2 diabetes and in mouse models of diabetes, the expression of Ppargc1a and Hnf4a are increased which results increases the expression of genes that result in gluconeogenesis (phosphoenolpyruvate carboxykinase 1; Pck1) and aberrant glucose export from the liver (glucose-6-phosphatase, G6pc). In the current study, Ppargc1a expression was decreased in KO (p=0.014); and Hnf4a was significantly decreased in expression by the KO diet. There were also marked reductions by KO in the expression of two targets of Ppargc1a/Hnf4a (see FIG. 35), with Pck1 being significantly decreased by KO and G6pc showing a trend for a decrease by KO (p=0.04). These data strongly suggest that krill oil has the ability to suppress hepatic glucose production which is increased in type 2 diabetes. Suppression of gluconeogenesis and hepatic glucose output via modulation of Ppargc1a activity has been proposed as a strong therapeutic target for the treatment of diabetes, provided that the intervention does not oppose the beneficial effects of Ppargc1a expression in other tissues. The krill supplements used in this study may functionally decrease hepatic glucose production and increase glucose uptake in tissues other than liver.

The effect of diet on hepatic lipid metabolism was also studied. The KO diet resulted in a gene expression profile suggesting decreased hepatic lipid accumulation. There is a significant modulation of the GO term "lipid biosynthesis." While decreased hepatic lipid synthesis in the KO group may simply be a consequence of decreased substrate availability as a result of decreased glucose metabolism, this result may be of clinical significance as hepatic lipid accumulation (hepatic steatosis) is associated with insulin resistance and the metabolic syndrome in humans. Interestingly, fish oil did not significantly modulate lipid biosynthesis in this study. Thus, it is tempting to speculate that krill oil would be a novel dietary intervention to modulate key pathways of energy metabolism in the liver in a manner which would oppose the effect seen in type 2 diabetes.

Although it has been reported that n-3 PUFA supplementation increases the expression of genes involved in fatty acid oxidation, pathway analysis of the gene expression data in this study showed that the GO term "fatty acid metabolism" was significantly depressed by KO, with no effect of FO on this pathway. This effect is underscored by the decrease in the expression of key genes involved in mitochondria' fatty acid oxidation (see FIG. 36) including the liver isoform of the rate-limiting enzyme carnitine palmitoyl transferase 1 and three enzymes involved in mitochondrial fatty acid beta oxidation (Acads, Acadm, and Acadl). The reason for the discrepancy between this example and previous reports showing that n-3 PUFAs increase fatty acid oxidation is not clear. However, others have shown that expression of the Cpt1a gene is regulated by Ppargc1a, and the data from this study are in agreement with that finding.

Thus, there appears to be strong transcriptional evidence that fatty acid metabolism is decreased in response to krill oil supplementation.

PAGE analysis also revealed that KO significantly suppressed the pathway "cholesterol biosynthesis." Other studies have shown that krill oil has the ability to improve circulating triglycerides as well as cholesterol levels in rats and humans, and the current data provide molecular evidence to support those findings. Specifically, KO resulted in a significant decrease in the expression of two key genes in the pathway of cholesterol metabolism including the gene encoding the rate-limiting enzyme for cholesterol synthesis (Hmgcr) and the Pmvk gene which encodes a protein that catalyzes the fifth condensation reaction in cholesterol synthesis (FIG. 37). Others have suggested that the hyperlipidemic effects of dietary saturated fats are mediated through increased activity of PPARgamma coactivator, 1 beta (Ppargc1b) and sterol regulatory element binding factor 2 (Srebf2). As shown in FIG. 37, we observed a significant downregulation of both of these genes by KO. Thus, previous studies and the current study provide evidence that the liver is sensitive to the saturation of dietary fatty acids, and that Ppargc1b and Srepf2 activity may be the important regulators of cholesterol synthesis in response to dietary fatty acid saturation.

The effect of diet on mitochondrial respiratory activity was also studied, as well as its implications for reduced oxidative damage. PAGE revealed that the KO diet resulted in a significant activation of the GO term "mitochondrial respiratory chain"; this was largely caused by an increased expression of genes encoding subunits of Complex I (NADH dehydrogenase). KO was also associated with a significant decrease in the expression of superoxide dismutase 2 (Sod2, FIG. 34), a critical enzyme involved in the detoxification of reactive oxygen species in mitochondria. Biochemical assays of oxidative damage (lipid peroxidation, nucleic acid oxidation) in banked tissues would reveal if the transcriptional effects are seen at the biochemical level. It seems plausible, therefore, that the increased activity of the mitochondrial respiratory chain in KO mice is related to increased mitochondrial proton leak which would result in decreased oxidative damage.

The effect of diet on inflammatory pathways was also studied, although no striking effects were observed. PAGE analysis revealed that there was a trend for KO modulation of several pathways involved in inflammation, most notably an increase in the activity of "negative regulation of lymphocyte proliferation" (p<0.05), an anti-inflammatory action of KO may be more pronounced in adipose tissue or brain.

As a result of these studies, a proposed mechanism of action for krill oil-regulation of metabolism has been developed. The data above clearly support a role for krill oil-supplementation to have beneficial effects on hepatic glucose and lipid metabolism. Two key regulators of these metabolic pathways in liver are sterol regulatory element binding transcription factor 1 (Srebf1) and the carbohydrate recognition element binding protein (Mlxipl). Expression and activity of the genes encoding these transcriptional cofactors is increased by insulin (Srebf1) and glucose (Mlxipl) which results in a stimulation of glycolysis and hepatic lipogenesis leading to lipid accumulation and insulin resistance in the liver. Conversely, inhibition or deficiency of these proteins ameliorates metabolic abnormalities in mouse models of the metabolic syndrome. The KO diet robustly decreased the expression of these two genes (see FIG. 38), though FO had no effect. Post-translational regulation of these transcriptional cofactors by PUFAs appears to be specific to particularly fatty acids, although the current study suggests that the genes Srebf1 and Mlxipl are also regulated at the transcriptional level by certain PUFAs.

Figure 38:
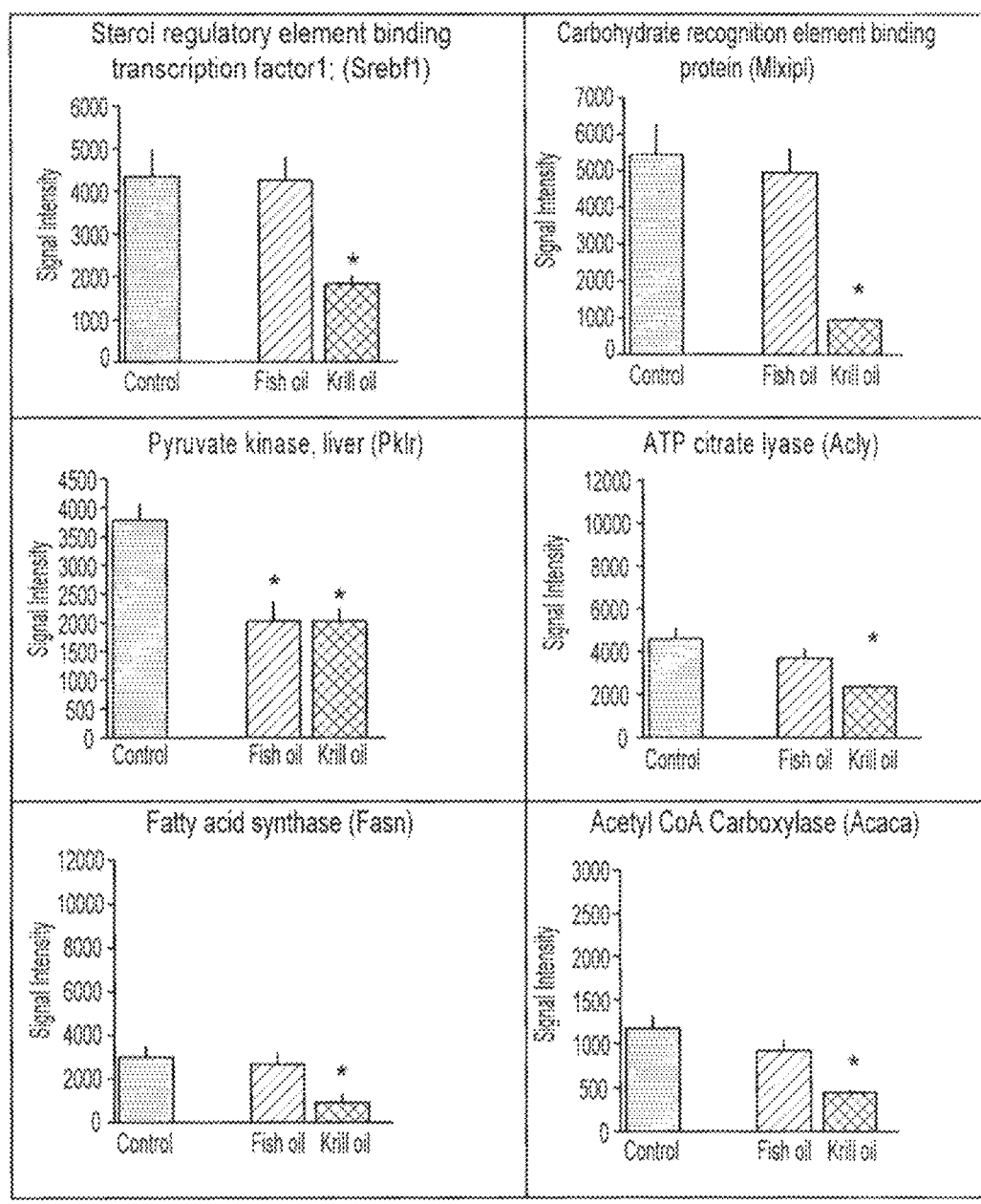

In addition to the decreased expression of these transcriptional cofactors, four genes known to be targets of these regulatory genes were decreased in expression by a krill oil-supplemented diets (see FIG. 38). These genes include: liver pyruvate kinase (Pklr), a regulatory enzyme in hepatic glycolysis; ATP citrate lyase (Acly) which catalyzes the conversion of citrate to acetyl CoA which can be used for synthesis of fatty acids; fatty acid synthase (Fasn) and acetyl CoA carboxylase (Acaca) which catalyze two of the initial steps of fatty acid synthesis. Because PAGE revealed that hepatic glucose and fatty acid metabolism are suppressed by krill oil-supplementation, the data altogether confirm that Srebf1 and Mlxipl are master regulators of hepatic metabolism, and their transcription and activity are modulated by krill oil-supplementation.

Example 13

This example, which was conducted using the study parameters set forth above in Example 12, addresses the effect of fish oil and krill oil on hepatic gene expression in mice. Fish oil was much less potent in changing the gene expression, compared to krill oil. Table 29 sets forth the pathways that are differently affected by krill oil and fish oil.

TABLE 29

| Pathway | GO IL | Genes | FC_CR | FC_FO | FC_KO |
|---|---|---|---|---|---|
| Fatty acid metabolic process | GO: 0006631 | 149 | −6.17 | 1.94 | −3.59 |
| Mono-carboxylic acid metabolic process | GO: 0032787 | 202 | −5.23 | 1.42 | −4.08 |
| Cellular lipid metabolic process | GO: 0044255 | 485 | −5.64 | 1.41 | −5.02 |
| Lipid metabolic process | GO: 0006629 | 568 | −65.49 | 1.50 | −5.18 |
| Peroxisome | GO: 0005777 | 90 | −7.23 | 3.59 | −1.60 |
| Fatty acid oxidation | GO: 0019395 | 20 | −5.49 | 1.95 | −2.16 |
| Fatty acid catabolic process | GO: 0009062 | 18 | −5.41 | 2.34 | −2.52 |

GO ID = The list of genes within a GO pathway can be obtained at the website for the Gene Ontology Consortium.
CR = calorie restriction diet.

The difference between krill oil and fish oil on the regulation of genes within lipid metabolism can be ascribed to their influence on key regulators of those genes. The most important transcription factors regulating these genes include PPAR alpha, PPAR delta, SREBP-1c, SREBP-2, ChREBP/Mlxipl, HNF-4 alpha, PGC-1 alpha, and PGC-1 beta.

Krill oil led to a downregulation of all of these transcription factors, whereas fish oil had no significant effect. Also, the same pattern was seen on the expression of target genes for each of the transcription factors.

Mitochondrial genes are in general down-regulated after treatment with krill oil. However, treatment with krill oil leads to a significant upregulation of certain classes of mitochondrial genes. Those genes appear to be associated with the electron transfer/respiratory chain, mitochondrial ribosomes, protein located at the inner mitochondrial membrane, and ATPases.

The majority of those genes are encoded in the nucleus. However, some genes in the respiratory chain are encoded in the mitochondria. The underlying mechanism behind this effect of krill oil is not known. However, it might indicate that the energy production in the liver is in some way affected. This effect is not seen after treatment with fish oil.

It will, of course, be appreciated that the above description has been given by way of example only and that modifications in detail may be made within the scope of the present invention.

Throughout this application, various patents and publications have been cited. The disclosures of these patents and publications in their entireties are hereby incorporated by reference into this application, for example, in order to more fully describe the state of the art to which this invention pertains.

The invention is capable of considerable modification, alteration, and equivalents in form and function, as will occur to those ordinarily skilled in the pertinent arts having the benefit of this disclosure.

While the present invention has been described for what are presently considered the preferred embodiments, the invention is not so limited. To the contrary, the invention is intended to cover various modifications and equivalent arrangements included within the spirit and scope of the detailed description provided above.

What is claimed is:

1. A method of reducing appetite in a human subject in need thereof comprising:
    administering to the human subject an effective amount of a krill oil composition, said krill oil composition comprising from about 40% w/w to about 60% w/w total phospholipids, wherein said total phospholipids comprise from about 3% to about 15% ether phospholipids, and said administering is carried out under conditions to reduce the appetite of the human subject.

2. The method of claim 1, wherein the human subject is obese.

3. The method of claim 1, wherein the krill oil composition further comprises greater than about 100 mg/kg astaxanthin esters.

4. The method of claim 1, wherein the krill oil composition further comprises from about 20% to 35% omega-3 fatty acids as a percentage of total fatty acids in the composition.

* * * * *